(12) United States Patent
Schnorr et al.

(10) Patent No.: US 8,143,047 B2
(45) Date of Patent: Mar. 27, 2012

(54) POLYPEPTIDES OF BOTRYOSPHAERIA RHODINA

(75) Inventors: Kirk Matthew Schnorr, Holte (DK); Lene Lange, Valby (DK); Pernille Uldall Bolvig, Roskilde (DK)

(73) Assignee: Novozymes A/s, Bagsvaerd (DK)

( * ) Notice: Subject to any disclaimer, the term of this patent is extended or adjusted under 35 U.S.C. 154(b) by 7 days.

(21) Appl. No.: 12/631,477

(22) Filed: Dec. 4, 2009

(65) Prior Publication Data

US 2010/0087379 A1    Apr. 8, 2010

Related U.S. Application Data

(62) Division of application No. 11/573,261, filed as application No. PCT/DK2005/000519 on Aug. 6, 2005, now Pat. No. 7,666,649.

(60) Provisional application No. 60/622,984, filed on Oct. 28, 2004.

(30) Foreign Application Priority Data

Aug. 6, 2004  (DK) ............................ PA 2004 01197
Aug. 11, 2004 (DK) ............................ PA 2004 01215

(51) Int. Cl.
C12N 9/24      (2006.01)
C12N 9/30      (2006.01)
C12P 21/06     (2006.01)
C12N 15/00     (2006.01)
C12P 19/34     (2006.01)
C12N 1/20      (2006.01)
C12N 1/00      (2006.01)
C07H 21/04     (2006.01)

(52) U.S. Cl. .... 435/200; 435/203; 435/69.1; 435/320.1; 435/91.1; 435/252.3; 435/254.11; 536/23.2; 536/23.74

(58) Field of Classification Search .................. 435/200, 435/203, 69.1, 320.1, 91.1, 252.3, 254.11; 536/23.2, 23.74
See application file for complete search history.

(56) References Cited

FOREIGN PATENT DOCUMENTS

| | | |
|---|---|---|
| CH | 654567 A | 2/1986 |
| EP | 1118672 A | 7/2001 |
| FR | 2786784 | 6/2000 |
| WO | WO 94/21785 A1 | 9/1994 |
| WO | WO 98/38288 | 9/1998 |
| WO | WO 01/49878 A | 7/2001 |
| WO | WO 01/77315 | 10/2001 |
| WO | WO 01/79507 A2 | 10/2001 |
| WO | WO 03/000941 A2 | 1/2003 |

OTHER PUBLICATIONS

Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Scott-Craig et al., Abstract AY622513 submitted to the EMBL/Genbank//DDBJ databases, 2004.
Ruiz-Roldan et al., Mol Gen Genet, 1999, vol. 261, pp. 530-536.
Kulkarni, et al., FEMS Microbiol Lett, 1999, vol. 23, No. 4, pp. 411-456.
Biely, et al., J Biotechnol, 1997, vol. 57, pp. 151-116.
Fleischmann, et al., Nature, 1995, vol. 269, pp. 496-512.
Dekker, et al., Biotechnology Lett, 2001, vol. 23, pp. 1987-1993.
Selbmann et al., Kluwer Academic Publishers, vol. 84, pp. 135-145 (2003).
Kisselev, Lev et al., Structure, vol. 10, pp. 8-9 (2002).
Wishart Matthew J. et al., Journal of Biological Chemistry, vol. 270, No. 45, pp. 26782-26785 (1995).
Witkowski Andrzej et al., Biochemistry, vol. 38, pp. 11643-11650 (1999).

* cited by examiner

*Primary Examiner* — Ganapathirama Raghu
(74) *Attorney, Agent, or Firm* — Elias Lambiris

(57) ABSTRACT

The invention relates to functional polypeptides secreted from *Botryospaeria rhodina* CBS 274.96.

15 Claims, No Drawings

SEQUENCE LISTING

<160> NUMBER OF SEQ ID NOS: 48

<210> SEQ ID NO 1
<211> LENGTH: 930
<212> TYPE: DNA
<213> ORGANISM: Botryosphaeria rhodina
<220> FEATURE:
<221> NAME/KEY: CDS
<222> LOCATION: (1)..(927)
<220> FEATURE:
<221> NAME/KEY: sig_peptide
<222> LOCATION: (1)..(54)
<220> FEATURE:
<221> NAME/KEY: mat_peptide
<222> LOCATION: (55)..(927)
<220> FEATURE:
<221> NAME/KEY: misc_feature
<222> LOCATION: (55)..(162)
<223> OTHER INFORMATION: Domain CBM1

<400> SEQUENCE: 1

```
atg cat cag aat tcc gcc ttg ttg ctg ctg gca gcc atc cca gcg acg        48
Met His Gln Asn Ser Ala Leu Leu Leu Leu Ala Ala Ile Pro Ala Thr
        -15                 -10                 -5 tat gcc gcc gtc cct gcc tgg ggt cag tgc ggc ggt tcg ggc tat agt        96
Tyr Ala Ala Val Pro Ala Trp Gly Gln Cys Gly Gly Ser Gly Tyr Ser
     -1   1               5                  10 ggc gaa acc act tgt gta tct ggt tat acc tgc gtg act gta aac caa       144
Gly Glu Thr Thr Cys Val Ser Gly Tyr Thr Cys Val Thr Val Asn Gln
 15                  20                  25                  30 tgg tac tcc caa tgc cag caa gga tcc gca ggt ccc acc acg acg ctc       192
Trp Tyr Ser Gln Cys Gln Gln Gly Ser Ala Gly Pro Thr Thr Thr Leu
                 35                  40                  45 gcc aca gtc aca acc acg ggc agc ggc acc acg ccg agc tcg acc tct       240
Ala Thr Val Thr Thr Thr Gly Ser Gly Thr Thr Pro Ser Ser Thr Ser
                 50                  55                  60 ggc agc atc gat gcc aag ttc aag gcc aag gga aag aag tac ttt ggc       288
Gly Ser Ile Asp Ala Lys Phe Lys Ala Lys Gly Lys Lys Tyr Phe Gly
 65                  70                  75 gtg gcg acg gac cag ggc cga ctc acg agc ggg cag aac gcg gcc atc       336
Val Ala Thr Asp Gln Gly Arg Leu Thr Ser Gly Gln Asn Ala Ala Ile
 80                  85                  90 atc aaa gcc gac ttt ggc cag gtc acg ccg gag aac agc atg aag tgg       384
Ile Lys Ala Asp Phe Gly Gln Val Thr Pro Glu Asn Ser Met Lys Trp
 95                 100                 105                 110 gac gcc acc gag cct tca cgc aac acg ttc acc ttc acg acg gcc gac       432
Asp Ala Thr Glu Pro Ser Arg Asn Thr Phe Thr Phe Thr Thr Ala Asp
                115                 120                 125 tac ctg gtt gat tgg gcg acg acc aac gac aag ctg atc cgt ggc cac       480
Tyr Leu Val Asp Trp Ala Thr Thr Asn Asp Lys Leu Ile Arg Gly His
                130                 135                 140
```

```
acg acc gtc tgg cac tcg cag ctg ccc acc tgg gtc tca agc atc acc        528
Thr Thr Val Trp His Ser Gln Leu Pro Thr Trp Val Ser Ser Ile Thr
        145                 150                 155 gat aag gcc act ttg acg acc gtc atg cag aac cac atc gcc acc gaa        576
Asp Lys Ala Thr Leu Thr Thr Val Met Gln Asn His Ile Ala Thr Glu
160                 165                 170 atg ggt cgc tgg aag ggc aag atc tac gct tgg gat gtc gtc aac gag        624
Met Gly Arg Trp Lys Gly Lys Ile Tyr Ala Trp Asp Val Val Asn Glu
175                 180                 185                 190 atc ttc aac gag gac ggc tca ttc agg tcc tcg gtc ttc tac aac gtc        672
Ile Phe Asn Glu Asp Gly Ser Phe Arg Ser Ser Val Phe Tyr Asn Val
                    195                 200                 205 ctc ggc gag gac ttt gtc cgc ctc gcc ttc gag gct gcg cgc gcc gcc        720
Leu Gly Glu Asp Phe Val Arg Leu Ala Phe Glu Ala Ala Arg Ala Ala
                210                 215                 220 gac ccc aac gcc aag ctg tac atc aac gac tac aac ctc gac tcc gcc        768
Asp Pro Asn Ala Lys Leu Tyr Ile Asn Asp Tyr Asn Leu Asp Ser Ala
            225                 230                 235 acc tac gcc aaa acc acc ggc ctg gac gtc acc aac tgc gtc ggc atc        816
Thr Tyr Ala Lys Thr Thr Gly Leu Asp Val Thr Asn Cys Val Gly Ile
240                 245                 250 acc gtt tgg ggc ctg cgc gac ccg gat agc tgg agg gcg agc agc acg        864
Thr Val Trp Gly Leu Arg Asp Pro Asp Ser Trp Arg Ala Ser Ser Thr
255                 260                 265                 270 ccg ttg ctg ttt gat gcc gac ttc cag ccg aag gcc gcg tat acc gcc        912
Pro Leu Leu Phe Asp Ala Asp Phe Gln Pro Lys Ala Ala Tyr Thr Ala
                275                 280                 285 att ttg aac agt ttg tag                                                930
Ile Leu Asn Ser Leu
            290

<210> SEQ ID NO 2
<211> LENGTH: 309
<212> TYPE: PRT
<213> ORGANISM: Botryosphaeria rhodina

<400> SEQUENCE: 2

Met His Gln Asn Ser Ala Leu Leu Leu Ala Ala Ile Pro Ala Thr
            -15                 -10                 -5

Tyr Ala Ala Val Pro Ala Trp Gly Gln Cys Gly Gly Ser Gly Tyr Ser
    -1  1               5                   10

Gly Glu Thr Thr Cys Val Ser Gly Tyr Thr Cys Val Thr Val Asn Gln
15                  20                  25                  30

Trp Tyr Ser Gln Cys Gln Gln Gly Ser Ala Gly Pro Thr Thr Thr Leu
                35                  40                  45

Ala Thr Val Thr Thr Thr Gly Ser Gly Thr Thr Pro Ser Ser Thr Ser
            50                  55                  60

Gly Ser Ile Asp Ala Lys Phe Lys Ala Lys Gly Lys Lys Tyr Phe Gly
        65                  70                  75

Val Ala Thr Asp Gln Gly Arg Leu Thr Ser Gly Gln Asn Ala Ala Ile
    80                  85                  90

Ile Lys Ala Asp Phe Gly Gln Val Thr Pro Glu Asn Ser Met Lys Trp
95                  100                 105                 110

Asp Ala Thr Glu Pro Ser Arg Asn Thr Phe Thr Phe Thr Thr Ala Asp
                115                 120                 125

Tyr Leu Val Asp Trp Ala Thr Thr Asn Asp Lys Leu Ile Arg Gly His
            130                 135                 140

Thr Thr Val Trp His Ser Gln Leu Pro Thr Trp Val Ser Ser Ile Thr
        145                 150                 155
```

```
Asp Lys Ala Thr Leu Thr Thr Val Met Gln Asn His Ile Ala Thr Glu
    160                 165                 170

Met Gly Arg Trp Lys Gly Lys Ile Tyr Ala Trp Asp Val Val Asn Glu
175                 180                 185                 190

Ile Phe Asn Glu Asp Gly Ser Phe Arg Ser Val Phe Tyr Asn Val
                195                 200                 205

Leu Gly Glu Asp Phe Val Arg Leu Ala Phe Glu Ala Ala Arg Ala Ala
            210                 215                 220

Asp Pro Asn Ala Lys Leu Tyr Ile Asn Asp Tyr Asn Leu Asp Ser Ala
            225                 230                 235

Thr Tyr Ala Lys Thr Thr Gly Leu Asp Val Thr Asn Cys Val Gly Ile
240                 245                 250

Thr Val Trp Gly Leu Arg Asp Pro Asp Ser Trp Arg Ala Ser Ser Thr
255                 260                 265                 270

Pro Leu Leu Phe Asp Ala Asp Phe Gln Pro Lys Ala Ala Tyr Thr Ala
                275                 280                 285

Ile Leu Asn Ser Leu
            290

<210> SEQ ID NO 3
<211> LENGTH: 663
<212> TYPE: DNA
<213> ORGANISM: Botryosphaeria rhodina
<220> FEATURE:
<221> NAME/KEY: CDS
<222> LOCATION: (1)..(663)
<220> FEATURE:
<221> NAME/KEY: sig_peptide
<222> LOCATION: (1)..(57)
<220> FEATURE:
<221> NAME/KEY: mat_peptide
<222> LOCATION: (58)..(663)

<400> SEQUENCE: 3 atg gtc tcc ttc aag tcg att ctt ctc act ctc acc gcc gct gcc agc      48
Met Val Ser Phe Lys Ser Ile Leu Leu Thr Leu Thr Ala Ala Ala Ser
                -15                 -10                 -5 gtc ttc tcc gcc ccg acc cct gag gcg ggc gag ctg atc gcg agg cag      96
Val Phe Ser Ala Pro Thr Pro Glu Ala Gly Glu Leu Ile Ala Arg Gln
        -1  1               5                   10 aac acg cca agc ggc acc ggc acg cac aac ggc tac ttc tat tcc ttc     144
Asn Thr Pro Ser Gly Thr Gly Thr His Asn Gly Tyr Phe Tyr Ser Phe
 15                  20                  25 tgg acc gac ggt gct ggc cag gtg acc tac acc aac ggc gct ggt ggt     192
Trp Thr Asp Gly Ala Gly Gln Val Thr Tyr Thr Asn Gly Ala Gly Gly
 30              35                  40                  45 tcg tac agc gtg acg tgg tcc ggc aac gcc ggc aac tgg gtt ggc ggc     240
Ser Tyr Ser Val Thr Trp Ser Gly Asn Ala Gly Asn Trp Val Gly Gly
             50                  55                  60 aag gga tgg cag acg ggc agc gcc agg acg atc aac tac tcg ggc acc     288
Lys Gly Trp Gln Thr Gly Ser Ala Arg Thr Ile Asn Tyr Ser Gly Thr
         65                  70                  75 tac aac ccc aac ggc aac tcg tac ctc gcc gtg tac ggc tgg tcg cgc     336
Tyr Asn Pro Asn Gly Asn Ser Tyr Leu Ala Val Tyr Gly Trp Ser Arg
     80                  85                  90 aac ccg ctg gtg gag tac tac atc gtc gag tcg tac ggc acg tac aac     384
Asn Pro Leu Val Glu Tyr Tyr Ile Val Glu Ser Tyr Gly Thr Tyr Asn
 95                 100                 105 ccg ggc tcg ggc ggc acc aag aag ggc acg gtc acg tcg gac ggc ggc     432
Pro Gly Ser Gly Gly Thr Lys Lys Gly Thr Val Thr Ser Asp Gly Gly
110                 115                 120                 125
```

```
acc tac gac atc tac gtg agc acc cgc acc aac gcg ccc agc atc gac     480
Thr Tyr Asp Ile Tyr Val Ser Thr Arg Thr Asn Ala Pro Ser Ile Asp
            130                 135                 140 ggc acc cag acc ttc cag cag tac tgg tcc gtg cgc cag tcc aag cgc     528
Gly Thr Gln Thr Phe Gln Gln Tyr Trp Ser Val Arg Gln Ser Lys Arg
        145                 150                 155 gtc ggc ggc acc gtg acg acc aag aac cac ttc gat gcc tgg gcc gcc     576
Val Gly Gly Thr Val Thr Thr Lys Asn His Phe Asp Ala Trp Ala Ala
    160                 165                 170 gtt ggc ctt aac ctg ggc act ttc gac tac cag atc gtc gct acc gag     624
Val Gly Leu Asn Leu Gly Thr Phe Asp Tyr Gln Ile Val Ala Thr Glu
175                 180                 185 ggc tac cag agc agc ggg tcg gct acg att acc gtg cag                 663
Gly Tyr Gln Ser Ser Gly Ser Ala Thr Ile Thr Val Gln
190                 195                 200

<210> SEQ ID NO 4
<211> LENGTH: 221
<212> TYPE: PRT
<213> ORGANISM: Botryosphaeria rhodina

<400> SEQUENCE: 4

Met Val Ser Phe Lys Ser Ile Leu Leu Thr Leu Thr Ala Ala Ala Ser
                -15                 -10                  -5

Val Phe Ser Ala Pro Thr Pro Glu Ala Gly Glu Leu Ile Ala Arg Gln
         -1  1               5                  10

Asn Thr Pro Ser Gly Thr Gly Thr His Asn Gly Tyr Phe Tyr Ser Phe
         15                  20                  25

Trp Thr Asp Gly Ala Gly Gln Val Thr Tyr Thr Asn Gly Ala Gly Gly
 30                  35                  40                  45

Ser Tyr Ser Val Thr Trp Ser Gly Asn Ala Gly Asn Trp Val Gly Gly
                 50                  55                  60

Lys Gly Trp Gln Thr Gly Ser Ala Arg Thr Ile Asn Tyr Ser Gly Thr
             65                  70                  75

Tyr Asn Pro Asn Gly Asn Ser Tyr Leu Ala Val Tyr Gly Trp Ser Arg
         80                  85                  90

Asn Pro Leu Val Glu Tyr Tyr Ile Val Glu Ser Tyr Gly Thr Tyr Asn
     95                 100                 105

Pro Gly Ser Gly Gly Thr Lys Lys Gly Thr Val Thr Ser Asp Gly Gly
110                 115                 120                 125

Thr Tyr Asp Ile Tyr Val Ser Thr Arg Thr Asn Ala Pro Ser Ile Asp
            130                 135                 140

Gly Thr Gln Thr Phe Gln Gln Tyr Trp Ser Val Arg Gln Ser Lys Arg
        145                 150                 155

Val Gly Gly Thr Val Thr Thr Lys Asn His Phe Asp Ala Trp Ala Ala
    160                 165                 170

Val Gly Leu Asn Leu Gly Thr Phe Asp Tyr Gln Ile Val Ala Thr Glu
175                 180                 185

Gly Tyr Gln Ser Ser Gly Ser Ala Thr Ile Thr Val Gln
190                 195                 200

<210> SEQ ID NO 5
<211> LENGTH: 1113
<212> TYPE: DNA
<213> ORGANISM: Botryosphaeria rhodina
<220> FEATURE:
<221> NAME/KEY: CDS
<222> LOCATION: (1)..(1110)
<220> FEATURE:
```

```
<221> NAME/KEY: misc_feature
<222> LOCATION: (1)..(1110)
<223> OTHER INFORMATION: Propeptide
<220> FEATURE:
<221> NAME/KEY: transit_peptide
<222> LOCATION: (1)..(54)
<220> FEATURE:
<221> NAME/KEY: mat_peptide
<222> LOCATION: (55)..(1110)

<400> SEQUENCE: 5
```

| | | | | | | | | | | | | | | | | |
|---|---|---|---|---|---|---|---|---|---|---|---|---|---|---|---|---|
| atg | gtc | gct | atc | aac | tac | ctc | gca | acc | ctg | gcc | ctg | gcg | gcc | tca | gca | 48 |
| Met | Val | Ala | Ile | Asn | Tyr | Leu | Ala | Thr | Leu | Ala | Leu | Ala | Ala | Ser | Ala | |
| | | | -15 | | | | -10 | | | | -5 | | | | | |
| agc | gcc | atc | ccc | atg | gac | tcc | cgc | ctg | gaa | gcg | cgc | caa | agc | ttc | tcc | 96 |
| Ser | Ala | Ile | Pro | Met | Asp | Ser | Arg | Leu | Glu | Ala | Arg | Gln | Ser | Phe | Ser | |
| | -1 | 1 | | | 5 | | | | | 10 | | | | | | |
| atc | ccc | ggc | atc | ggc | gga | cag | acc | gcc | aac | gac | gtg | cag | tcc | ggt | acc | 144 |
| Ile | Pro | Gly | Ile | Gly | Gly | Gln | Thr | Ala | Asn | Asp | Val | Gln | Ser | Gly | Thr | |
| 15 | | | | | 20 | | | | | 25 | | | | | 30 | |
| tgc | aag | gac | gtg | acg | tac | atc | ttc | gcg | cgg | ggc | acg | acg | gag | cag | ggc | 192 |
| Cys | Lys | Asp | Val | Thr | Tyr | Ile | Phe | Ala | Arg | Gly | Thr | Thr | Glu | Gln | Gly | |
| | | | | 35 | | | | | 40 | | | | | 45 | | |
| aac | atg | ggc | agc | acg | gtc | ggg | ccg | gcg | ctg | aag | acg | aag | ctg | gag | gcg | 240 |
| Asn | Met | Gly | Ser | Thr | Val | Gly | Pro | Ala | Leu | Lys | Thr | Lys | Leu | Glu | Ala | |
| | | | 50 | | | | | 55 | | | | | 60 | | | |
| gcc | atc | ggc | gcc | gac | aag | ctc | gcg | acg | cag | ggc | gtc | aac | tac | ccg | gcc | 288 |
| Ala | Ile | Gly | Ala | Asp | Lys | Leu | Ala | Thr | Gln | Gly | Val | Asn | Tyr | Pro | Ala | |
| | | 65 | | | | | 70 | | | | | 75 | | | | |
| gac | gtg | gcg | ggc | acc | gtc | gtc | ggc | agc | atg | tca | ccc | ggc | cag | gcc | gag | 336 |
| Asp | Val | Ala | Gly | Thr | Val | Val | Gly | Ser | Met | Ser | Pro | Gly | Gln | Ala | Glu | |
| | 80 | | | | | 85 | | | | | 90 | | | | | |
| ggc | agc | aag | aac | tgc | gcg | cag | ctg | gtc | aaa | cag | gct | ttg | tcc | aac | tgc | 384 |
| Gly | Ser | Lys | Asn | Cys | Ala | Gln | Leu | Val | Lys | Gln | Ala | Leu | Ser | Asn | Cys | |
| 95 | | | | | 100 | | | | | 105 | | | | | 110 | |
| ccg | cag | acc | aag | atc | gtg | ctg | gcc | ggc | tac | tcg | cag | ggc | gcg | cag | cag | 432 |
| Pro | Gln | Thr | Lys | Ile | Val | Leu | Ala | Gly | Tyr | Ser | Gln | Gly | Ala | Gln | Gln | |
| | | | | 115 | | | | | 120 | | | | | 125 | | |
| gtc | cac | ggc | tgc | ctc | atc | gat | ttg | agc | gcc | gat | gag | gcg | cag | aag | gtc | 480 |
| Val | His | Gly | Cys | Leu | Ile | Asp | Leu | Ser | Ala | Asp | Glu | Ala | Gln | Lys | Val | |
| | | | 130 | | | | | 135 | | | | | 140 | | | |
| gcg | gcc | gcc | gtc | acc | ttc | ggc | gac | ccc | ctg | cgg | gcg | cag | cag | ttc | aag | 528 |
| Ala | Ala | Ala | Val | Thr | Phe | Gly | Asp | Pro | Leu | Arg | Ala | Gln | Gln | Phe | Lys | |
| | | 145 | | | | | 150 | | | | | 155 | | | | |
| aac | atc | gac | cag | tcg | cgc | acc | aag | atc | ttc | tgc | gcc | acc | ggc | gac | ctc | 576 |
| Asn | Ile | Asp | Gln | Ser | Arg | Thr | Lys | Ile | Phe | Cys | Ala | Thr | Gly | Asp | Leu | |
| | 160 | | | | | 165 | | | | | 170 | | | | | |
| gtc | tgc | acc | aac | cag | ttc | atc | atc | acg | gcc | gcc | cac | ctc | tcc | tat | gcc | 624 |
| Val | Cys | Thr | Asn | Gln | Phe | Ile | Ile | Thr | Ala | Ala | His | Leu | Ser | Tyr | Ala | |
| 175 | | | | | 180 | | | | | 185 | | | | | 190 | |
| tcc | gag | tcc | acc | ggc | ccg | gcc | gcc | gag | ttc | atc | cag | cag | cag | ctg | ggc | 672 |
| Ser | Glu | Ser | Thr | Gly | Pro | Ala | Ala | Glu | Phe | Ile | Gln | Gln | Gln | Leu | Gly | |
| | | | | 195 | | | | | 200 | | | | | 205 | | |
| act | ctc | gac | tcc | tct | tct | tcc | tcg | tcc | aac | agc | tcg | tcg | tcg | acg | acg | 720 |
| Thr | Leu | Asp | Ser | Ser | Ser | Ser | Ser | Ser | Asn | Ser | Ser | Ser | Ser | Thr | Thr | |
| | | | 210 | | | | | 215 | | | | | 220 | | | |
| acg | gcg | tca | act | tcc | gct | gac | agc | agc | gcc | acc | agt | acc | ggc | tcg | tcc | 768 |
| Thr | Ala | Ser | Thr | Ser | Ala | Asp | Ser | Ser | Ala | Thr | Ser | Thr | Gly | Ser | Ser | |
| | | 225 | | | | | 230 | | | | | 235 | | | | |
| gac | agc | agc | gtt | gcc | tcg | tct | ggc | cta | ggc | tcc | ggg | ctt | ctc | ggt | ggc | 816 |
| Asp | Ser | Ser | Val | Ala | Ser | Ser | Gly | Leu | Gly | Ser | Gly | Leu | Leu | Gly | Gly | |
| | 240 | | | | | 245 | | | | | 250 | | | | | |

| | | | | | | | | | | | | | | | | |
|---|---|---|---|---|---|---|---|---|---|---|---|---|---|---|---|---|
| ggc | ttg | agt | ggc | ttg | acc | ggt | ggc | ggt | tcc | agc | ggt | ggt | tcg | agt | ctg | 864 |
| Gly | Leu | Ser | Gly | Leu | Thr | Gly | Gly | Gly | Ser | Ser | Gly | Gly | Ser | Ser | Leu | |
| 255 | | | | 260 | | | | | 265 | | | | | 270 | | |
| ctc | agc | ggc | ttg | agc | ggt | ctg | agt | gga | agt | gat | tcc | agc | agc | agt | ggc | 912 |
| Leu | Ser | Gly | Leu | Ser | Gly | Leu | Ser | Gly | Ser | Asp | Ser | Ser | Ser | Ser | Gly | |
| | | 275 | | | | | 280 | | | | | 285 | | | | |
| ggt | tcg | agc | ctc | ctg | agt | gga | ttg | agc | gga | ttg | agc | ggg | agc | agc | ggt | 960 |
| Gly | Ser | Ser | Leu | Leu | Ser | Gly | Leu | Ser | Gly | Leu | Ser | Gly | Ser | Ser | Gly | |
| | | 290 | | | | | 295 | | | | | 300 | | | | |
| tcc | agc | gac | agc | ggt | tcg | agc | atg | ctt | ggc | ggg | ctc | agc | ggt | ctc | agt | 1008 |
| Ser | Ser | Asp | Ser | Gly | Ser | Ser | Met | Leu | Gly | Gly | Leu | Ser | Gly | Leu | Ser | |
| | | 305 | | | | | 310 | | | | | 315 | | | | |
| ggg | ctt | agc | ggg | ctg | gga | gga | tcg | tcg | agc | ggc | gga | tcg | ggc | ctc | atg | 1056 |
| Gly | Leu | Ser | Gly | Leu | Gly | Gly | Ser | Ser | Ser | Gly | Gly | Ser | Gly | Leu | Met | |
| | | 320 | | | | | 325 | | | | | 330 | | | | |
| agc | ggt | ttg | agc | ggt | ctg | agt | ggc | ctg | agc | ggc | ctt | ggg | ggc | tcg | aag | 1104 |
| Ser | Gly | Leu | Ser | Gly | Leu | Ser | Gly | Leu | Ser | Gly | Leu | Gly | Gly | Ser | Lys | |
| 335 | | | | 340 | | | | | 345 | | | | | 350 | | |
| aag | aac | tga | | | | | | | | | | | | | | 1113 |
| Lys | Asn | | | | | | | | | | | | | | | |

<210> SEQ ID NO 6
<211> LENGTH: 370
<212> TYPE: PRT
<213> ORGANISM: Botryosphaeria rhodina

<400> SEQUENCE: 6

```
Met Val Ala Ile Asn Tyr Leu Ala Thr Leu Ala Leu Ala Ala Ser Ala
            -15                 -10                  -5

Ser Ala Ile Pro Met Asp Ser Arg Leu Glu Ala Arg Gln Ser Phe Ser
 -1   1               5                  10

Ile Pro Gly Ile Gly Gly Gln Thr Ala Asn Asp Val Gln Ser Gly Thr
15                  20                  25                  30

Cys Lys Asp Val Thr Tyr Ile Phe Ala Arg Gly Thr Thr Glu Gln Gly
                35                  40                  45

Asn Met Gly Ser Thr Val Gly Pro Ala Leu Lys Thr Lys Leu Glu Ala
            50                  55                  60

Ala Ile Gly Ala Asp Lys Leu Ala Thr Gln Gly Val Asn Tyr Pro Ala
65                  70                  75

Asp Val Ala Gly Thr Val Val Gly Ser Met Ser Pro Gly Gln Ala Glu
            80                  85                  90

Gly Ser Lys Asn Cys Ala Gln Leu Val Lys Gln Ala Leu Ser Asn Cys
95                  100                 105                 110

Pro Gln Thr Lys Ile Val Leu Ala Gly Tyr Ser Gln Gly Ala Gln Gln
                115                 120                 125

Val His Gly Cys Leu Ile Asp Leu Ser Ala Asp Glu Ala Gln Lys Val
            130                 135                 140

Ala Ala Ala Val Thr Phe Gly Asp Pro Leu Arg Ala Gln Gln Phe Lys
            145                 150                 155

Asn Ile Asp Gln Ser Arg Thr Lys Ile Phe Cys Ala Thr Gly Asp Leu
160                 165                 170

Val Cys Thr Asn Gln Phe Ile Ile Thr Ala Ala His Leu Ser Tyr Ala
175                 180                 185                 190

Ser Glu Ser Thr Gly Pro Ala Ala Glu Phe Ile Gln Gln Leu Gly
                195                 200                 205

Thr Leu Asp Ser Ser Ser Ser Ser Asn Ser Ser Ser Thr Thr
            210                 215                 220
```

```
Thr Ala Ser Thr Ser Ala Asp Ser Ser Ala Thr Ser Thr Gly Ser Ser
            225                 230                 235

Asp Ser Ser Val Ala Ser Ser Gly Leu Gly Ser Gly Leu Leu Gly Gly
    240                 245                 250

Gly Leu Ser Gly Leu Thr Gly Gly Gly Ser Ser Gly Gly Ser Ser Leu
255                 260                 265                 270

Leu Ser Gly Leu Ser Gly Leu Ser Gly Asp Ser Ser Ser Ser Gly
                275                 280                 285

Gly Ser Ser Leu Leu Ser Gly Leu Ser Gly Leu Ser Gly Ser Ser Gly
                290                 295                 300

Ser Ser Asp Ser Gly Ser Ser Met Leu Gly Gly Leu Ser Gly Leu Ser
            305                 310                 315

Gly Leu Ser Gly Leu Gly Gly Ser Ser Ser Gly Gly Ser Gly Leu Met
                320                 325                 330

Ser Gly Leu Ser Gly Leu Ser Gly Leu Ser Gly Leu Gly Gly Ser Lys
335                 340                 345                 350

Lys Asn

<210> SEQ ID NO 7
<211> LENGTH: 1350
<212> TYPE: DNA
<213> ORGANISM: Botryosphaeria rhodina
<220> FEATURE:
<221> NAME/KEY: CDS
<222> LOCATION: (1)..(1347)
<220> FEATURE:
<221> NAME/KEY: misc_feature
<222> LOCATION: (1)..(1347)
<223> OTHER INFORMATION: Propeptide
<220> FEATURE:
<221> NAME/KEY: transit_peptide
<222> LOCATION: (1)..(54)
<220> FEATURE:
<221> NAME/KEY: mat_peptide
<222> LOCATION: (55)..(1347)

<400> SEQUENCE: 7 atg cat ttg tcc agt gtt tgt ctc gtc ctc agt ggg ctt ctc ctt acc      48
Met His Leu Ser Ser Val Cys Leu Val Leu Ser Gly Leu Leu Leu Thr
        -15                 -10                  -5 aac gct gcc cca gcc cct gtc cct gaa aat ggg ctc gag aag agg cag      96
Asn Ala Ala Pro Ala Pro Val Pro Glu Asn Gly Leu Glu Lys Arg Gln
 -1   1               5                  10 tcc ctg agc agc gtc ctg agc gcc ctc agt ggc ctg acc gaa cct acg     144
Ser Leu Ser Ser Val Leu Ser Ala Leu Ser Gly Leu Thr Glu Pro Thr
 15                  20                  25                  30 gcc atc ttg tct cag ctc gag gcg gtt gaa gcg aca tcg acg ccc acc     192
Ala Ile Leu Ser Gln Leu Glu Ala Val Glu Ala Thr Ser Thr Pro Thr
                 35                  40                  45 agc gtc gag cag gcg cag gag cag ctc gag gcc atc tac ggg acg aca     240
Ser Val Glu Gln Ala Gln Glu Gln Leu Glu Ala Ile Tyr Gly Thr Thr
             50                  55                  60 cca acc aac atc ttc gag aac atc gcg cag caa atc gcc gac gga ctg     288
Pro Thr Asn Ile Phe Glu Asn Ile Ala Gln Gln Ile Ala Asp Gly Leu
         65                  70                  75 tcg acg ctg acc atc gtc caa gcc ctc ggc ttc tcc ccc agc ggc gag     336
Ser Thr Leu Thr Ile Val Gln Ala Leu Gly Phe Ser Pro Ser Gly Glu
     80                  85                  90 aac tcg gaa acc aac agc aac acg cgc gaa ccg tcg acg acc atc tac     384
Asn Ser Glu Thr Asn Ser Asn Thr Arg Glu Pro Ser Thr Thr Ile Tyr
 95                 100                 105                 110 ccc aag aag tcg tcc tcg gat gcc ccc tat tcc atc act gag gaa gag     432
```

|     |     |     |     |     |     |     |     |     |     |     |     |     |     |     |      |
| --- | --- | --- | --- | --- | --- | --- | --- | --- | --- | --- | --- | --- | --- | --- | ---- |
|     |     | Pro | Lys | Lys | Ser | Ser | Ser | Asp | Ala | Pro | Tyr | Ser | Ile | Thr | Glu | Glu |
|     |     |     |     |     | 115 |     |     |     |     | 120 |     |     |     |     | 125 |

```
ctc cgc caa gcc atc tac atc ccc tcc gac ttc acg tac ggc gac aag      480
Leu Arg Gln Ala Ile Tyr Ile Pro Ser Asp Phe Thr Tyr Gly Asp Lys
        130                 135                 140 ccg ccg gtc atc ttc gtg ccg gga acg ggc tcg tac ggc ggc atc agc      528
Pro Pro Val Ile Phe Val Pro Gly Thr Gly Ser Tyr Gly Gly Ile Ser
        145                 150                 155 ttc gga tcg aac ctg cgc aag ctg ctg acg ggc gtg tcg tac gcg gac      576
Phe Gly Ser Asn Leu Arg Lys Leu Leu Thr Gly Val Ser Tyr Ala Asp
        160                 165                 170 ccg gtc tgg ctc aac gtg ccg gac gcg ctg ctg cgc gac gcg cag acg      624
Pro Val Trp Leu Asn Val Pro Asp Ala Leu Leu Arg Asp Ala Gln Thr
175             180                 185                 190 aac ggc gag ttc gtg gcg tac gcc atc aac tac atc tcg ggc ata tcc      672
Asn Gly Glu Phe Val Ala Tyr Ala Ile Asn Tyr Ile Ser Gly Ile Ser
                195                 200                 205 ggc gac gcc aac gtg tcg gtc gtc tcg tgg tcg cag ggc ggg ctg gac      720
Gly Asp Ala Asn Val Ser Val Val Ser Trp Ser Gln Gly Gly Leu Asp
                210                 215                 220 acg cag tgg gct ttt act tat tgg ccg tcg acg cgc gcc ctg gtc tct      768
Thr Gln Trp Ala Phe Thr Tyr Trp Pro Ser Thr Arg Ala Leu Val Ser
            225                 230                 235 gac ttc gtg ccc gtc agc ccg gac ttc cac ggc acc gtc ctg gcc aac      816
Asp Phe Val Pro Val Ser Pro Asp Phe His Gly Thr Val Leu Ala Asn
240                 245                 250 gtc atc tgc ctc aac ccg ggc gcc ggc ggt gtt ggg ttg ggc ccc tgc      864
Val Ile Cys Leu Asn Pro Gly Ala Gly Gly Val Gly Leu Gly Pro Cys
255                 260                 265                 270 gcg ccg gcg gtg ctg cag cag gag tac aac agc aac ttc gtc acg gcc      912
Ala Pro Ala Val Leu Gln Gln Glu Tyr Asn Ser Asn Phe Val Thr Ala
                275                 280                 285 ctg cgc gcg gcg ggc ggt gcg gac gct tac gtg ccg acg acg tct gtt      960
Leu Arg Ala Ala Gly Gly Ala Asp Ala Tyr Val Pro Thr Thr Ser Val
                290                 295                 300 ttc tct ggc ttc ctc gat gag att gtc cag ccg cag tcc ggc acc ggc     1008
Phe Ser Gly Phe Leu Asp Glu Ile Val Gln Pro Gln Ser Gly Thr Gly
305                 310                 315 gcg tcc gcg tac atc aat gat gct agg ggt gtg ggc acg acc aat gcg     1056
Ala Ser Ala Tyr Ile Asn Asp Ala Arg Gly Val Gly Thr Thr Asn Ala
        320                 325                 330 gag gtg cag gtc gtg tgc aag ggc aag ggt ccc gct ggc ggt ttt tac     1104
Glu Val Gln Val Val Cys Lys Gly Lys Gly Pro Ala Gly Gly Phe Tyr
335                 340                 345                 350 acg cac gag agc ttg ctg gtc aac ccg ctg acc tat gct ctc ctc gtc     1152
Thr His Glu Ser Leu Leu Val Asn Pro Leu Thr Tyr Ala Leu Leu Val
                355                 360                 365 gat gcc ttg acc cat gat ggc ccg ggt agt gtg gac agg ctg gat ctg     1200
Asp Ala Leu Thr His Asp Gly Pro Gly Ser Val Asp Arg Leu Asp Leu
        370                 375                 380 gat acc gtg tgc tcg acc gtc gtg gcg ccc ggc ctg ggg ctg gat gcg     1248
Asp Thr Val Cys Ser Thr Val Val Ala Pro Gly Leu Gly Leu Asp Ala
            385                 390                 395 ttg ttg gag att gag ggc gtg aat gtt ctg gcc gct gtc aat ctg ttg     1296
Leu Leu Glu Ile Glu Gly Val Asn Val Leu Ala Ala Val Asn Leu Leu
400                 405                 410 acc tac tcg gac agg agg ttg gcc gag ccg gcg ctg atg tct tat gcg     1344
Thr Tyr Ser Asp Arg Arg Leu Ala Glu Pro Ala Leu Met Ser Tyr Ala
415                 420                 425                 430 gct taa                                                             1350
```

Ala

<210> SEQ ID NO 8
<211> LENGTH: 449
<212> TYPE: PRT
<213> ORGANISM: Botryosphaeria rhodina

<400> SEQUENCE: 8

```
Met His Leu Ser Ser Val Cys Leu Val Leu Ser Gly Leu Leu Leu Thr
            -15                 -10                  -5

Asn Ala Ala Pro Ala Pro Val Pro Glu Asn Gly Leu Glu Lys Arg Gln
     -1   1               5                  10

Ser Leu Ser Ser Val Leu Ser Ala Leu Ser Gly Leu Thr Glu Pro Thr
 15              20                  25                  30

Ala Ile Leu Ser Gln Leu Glu Ala Val Glu Ala Thr Ser Thr Pro Thr
                 35                  40                  45

Ser Val Glu Gln Ala Gln Glu Gln Leu Glu Ala Ile Tyr Gly Thr Thr
                 50                  55                  60

Pro Thr Asn Ile Phe Glu Asn Ile Ala Gln Gln Ile Ala Asp Gly Leu
             65                  70                  75

Ser Thr Leu Thr Ile Val Gln Ala Leu Gly Phe Ser Pro Ser Gly Glu
 80                  85                  90

Asn Ser Glu Thr Asn Ser Asn Thr Arg Glu Pro Ser Thr Thr Ile Tyr
 95                 100                 105                 110

Pro Lys Lys Ser Ser Asp Ala Pro Tyr Ser Ile Thr Glu Glu Glu
                115                 120                 125

Leu Arg Gln Ala Ile Tyr Ile Pro Ser Asp Phe Thr Tyr Gly Asp Lys
                130                 135                 140

Pro Pro Val Ile Phe Val Pro Gly Thr Gly Ser Tyr Gly Gly Ile Ser
                145                 150                 155

Phe Gly Ser Asn Leu Arg Lys Leu Leu Thr Gly Val Ser Tyr Ala Asp
160                 165                 170

Pro Val Trp Leu Asn Val Pro Asp Ala Leu Leu Arg Asp Ala Gln Thr
175                 180                 185                 190

Asn Gly Glu Phe Val Ala Tyr Ala Ile Asn Tyr Ile Ser Gly Ile Ser
                195                 200                 205

Gly Asp Ala Asn Val Ser Val Ser Trp Ser Gln Gly Gly Leu Asp
                210                 215                 220

Thr Gln Trp Ala Phe Thr Tyr Trp Pro Ser Thr Arg Ala Leu Val Ser
                225                 230                 235

Asp Phe Val Pro Val Ser Pro Asp Phe His Gly Thr Val Leu Ala Asn
240                 245                 250

Val Ile Cys Leu Asn Pro Gly Ala Gly Val Gly Leu Gly Pro Cys
255                 260                 265                 270

Ala Pro Ala Val Leu Gln Gln Glu Tyr Asn Ser Asn Phe Val Thr Ala
                275                 280                 285

Leu Arg Ala Ala Gly Gly Ala Asp Ala Tyr Val Pro Thr Thr Ser Val
                290                 295                 300

Phe Ser Gly Phe Leu Asp Glu Ile Val Gln Pro Gln Ser Gly Thr Gly
                305                 310                 315

Ala Ser Ala Tyr Ile Asn Asp Ala Arg Gly Val Gly Thr Thr Asn Ala
                320                 325                 330

Glu Val Gln Val Val Cys Lys Gly Lys Gly Pro Ala Gly Gly Phe Tyr
335                 340                 345                 350

Thr His Glu Ser Leu Leu Val Asn Pro Leu Thr Tyr Ala Leu Leu Val
```

|  |  |  | 355 |  |  |  | 360 |  |  |  | 365 |  |
|--|--|--|--|--|--|--|--|--|--|--|--|--|

Asp Ala Leu Thr His Asp Gly Pro Gly Ser Val Asp Arg Leu Asp Leu
          370                      375                      380

Asp Thr Val Cys Ser Thr Val Ala Pro Gly Leu Gly Leu Asp Ala
          385                      390                      395

Leu Leu Glu Ile Glu Gly Val Asn Val Leu Ala Ala Val Asn Leu Leu
      400                      405                    410

Thr Tyr Ser Asp Arg Arg Leu Ala Glu Pro Ala Leu Met Ser Tyr Ala
415                      420                    425                    430

Ala

<210> SEQ ID NO 9
<211> LENGTH: 555
<212> TYPE: DNA
<213> ORGANISM: Botryosphaeria rhodina
<220> FEATURE:
<221> NAME/KEY: CDS
<222> LOCATION: (1)..(555)

<400> SEQUENCE: 9

| atg cgc ttc gcc acc gcc gcc acc gcc ctc gcc ctc acc ggc ttc tgc | 48 |
|---|---|
| Met Arg Phe Ala Thr Ala Ala Thr Ala Leu Ala Leu Thr Gly Phe Cys | |
| 1               5                   10                  15 | |

| agc gcc gcc gtc ctg ccg cgc gcc acc gag cac aag gtc tac gtc gac | 96 |
|---|---|
| Ser Ala Ala Val Leu Pro Arg Ala Thr Glu His Lys Val Tyr Val Asp | |
|         20                  25                  30 | |

| act tcc aag tgc gcc gac aac ggc cgc acc ctg ccg cag atc tac ggc | 144 |
|---|---|
| Thr Ser Lys Cys Ala Asp Asn Gly Arg Thr Leu Pro Gln Ile Tyr Gly | |
|     35                  40                  45 | |

| atc tcc aac tcg acc tcg cag gac ttc acc gac ccg cag cgc ttc gac | 192 |
|---|---|
| Ile Ser Asn Ser Thr Ser Gln Asp Phe Thr Asp Pro Gln Arg Phe Asp | |
| 50                  55                  60 | |

| ggg ccc acc ttc acc ttc acc gtg ccc gcc tac tac cag ggc cac ctc | 240 |
|---|---|
| Gly Pro Thr Phe Thr Phe Thr Val Pro Ala Tyr Tyr Gln Gly His Leu | |
| 65                  70                  75                  80 | |

| tgg ctg tac aac agc gac gac cag gcc gcc tcg agc ggt gac aac acc | 288 |
|---|---|
| Trp Leu Tyr Asn Ser Asp Asp Gln Ala Ala Ser Ser Gly Asp Asn Thr | |
|             85                  90                  95 | |

| ccc ctg aac gtc cag ggc gtc gac ttc tac ttc tac gac cag ccc acc | 336 |
|---|---|
| Pro Leu Asn Val Gln Gly Val Asp Phe Tyr Phe Tyr Asp Gln Pro Thr | |
|             100                 105                 110 | |

| gac gtc gag cgc aac cag gcc acc gtg ccc gct gag ggc gac gcc aac | 384 |
|---|---|
| Asp Val Glu Arg Asn Gln Ala Thr Val Pro Ala Glu Gly Asp Ala Asn | |
|         115                 120                 125 | |

| cag gac ggc cag gtg tac agc gtt ccc gac ccc atc act gcc gtc cgc | 432 |
|---|---|
| Gln Asp Gly Gln Val Tyr Ser Val Pro Asp Pro Ile Thr Ala Val Arg | |
| 130                 135                 140 | |

| ttc gcc agc acc cct agc agc acc ttc atc gag ggc aag agc ggc ggg | 480 |
|---|---|
| Phe Ala Ser Thr Pro Ser Ser Thr Phe Ile Glu Gly Lys Ser Gly Gly | |
| 145                 150                 155                 160 | |

| cac tct gta cag cac cca gga ggg cga cgc tct gta cgt cta cta ctg | 528 |
|---|---|
| His Ser Val Gln His Pro Gly Gly Arg Arg Ser Val Arg Leu Leu Leu | |
|             165                 170                 175 | |

| cga gga gtg gcc cgt cca gaa cta gag | 555 |
|---|---|
| Arg Gly Val Ala Arg Pro Glu Leu Glu | |
|             180                 185 | |

<210> SEQ ID NO 10
<211> LENGTH: 185
<212> TYPE: PRT
<213> ORGANISM: Botryosphaeria rhodina

<400> SEQUENCE: 10

```
Met Arg Phe Ala Thr Ala Ala Thr Ala Leu Ala Leu Thr Gly Phe Cys
1               5                   10                  15

Ser Ala Ala Val Leu Pro Arg Ala Thr Glu His Lys Val Tyr Val Asp
            20                  25                  30

Thr Ser Lys Cys Ala Asp Asn Gly Arg Thr Leu Pro Gln Ile Tyr Gly
        35                  40                  45

Ile Ser Asn Ser Thr Ser Gln Asp Phe Thr Asp Pro Gln Arg Phe Asp
50                  55                  60

Gly Pro Thr Phe Thr Phe Thr Val Pro Ala Tyr Tyr Gln Gly His Leu
65                  70                  75                  80

Trp Leu Tyr Asn Ser Asp Asp Gln Ala Ala Ser Ser Gly Asp Asn Thr
                85                  90                  95

Pro Leu Asn Val Gln Gly Val Asp Phe Tyr Phe Tyr Asp Gln Pro Thr
            100                 105                 110

Asp Val Glu Arg Asn Gln Ala Thr Val Pro Ala Glu Gly Asp Ala Asn
        115                 120                 125

Gln Asp Gly Gln Val Tyr Ser Val Pro Asp Pro Ile Thr Ala Val Arg
130                 135                 140

Phe Ala Ser Thr Pro Ser Ser Thr Phe Ile Glu Gly Lys Ser Gly Gly
145                 150                 155                 160

His Ser Val Gln His Pro Gly Gly Arg Arg Ser Val Arg Leu Leu Leu
                165                 170                 175

Arg Gly Val Ala Arg Pro Glu Leu Glu
            180                 185
```

<210> SEQ ID NO 11
<211> LENGTH: 702
<212> TYPE: DNA
<213> ORGANISM: Botryosphaeria rhodina
<220> FEATURE:
<221> NAME/KEY: CDS
<222> LOCATION: (1)..(702)
<220> FEATURE:
<221> NAME/KEY: transit_peptide
<222> LOCATION: (1)..(48)
<220> FEATURE:
<221> NAME/KEY: misc_feature
<222> LOCATION: (1)..(702)
<223> OTHER INFORMATION: propeptide
<220> FEATURE:
<221> NAME/KEY: mat_peptide
<222> LOCATION: (49)..(702)

<400> SEQUENCE: 11

```
atg aag ggt ctc ttc gct att ctt gcc acg gct tcg gtc gtc tct gcc    48
Met Lys Gly Leu Phe Ala Ile Leu Ala Thr Ala Ser Val Val Ser Ala
    -15                 -10                 -5                  -1 cac gcc acc tgg cag gag ctc tgg gtt ggt act gag gac aag gag gga    96
His Ala Thr Trp Gln Glu Leu Trp Val Gly Thr Glu Asp Lys Glu Gly
 1               5                   10                  15 act tgc atc cgc ctt cct cag agc aac agc ccc gtc acc gat gtc acc   144
Thr Cys Ile Arg Leu Pro Gln Ser Asn Ser Pro Val Thr Asp Val Thr
            20                  25                  30 tcc aac gac atc cgc tgc aac gcc agc ccc agc gct gcc tcg acc act   192
Ser Asn Asp Ile Arg Cys Asn Ala Ser Pro Ser Ala Ala Ser Thr Thr
        35                  40                  45 tgc tcc gtt gcc gcc ggc ggt tca ctg acg gtt gag atg cac cag cag   240
Cys Ser Val Ala Ala Gly Gly Ser Leu Thr Val Glu Met His Gln Gln
50                  55                  60
```

```
ccc aac gac cgc agc tgc gac aac gag gcc atc ggt ggc aac cac ttc    288
Pro Asn Asp Arg Ser Cys Asp Asn Glu Ala Ile Gly Gly Asn His Phe
 65              70                  75                  80 ggc cca gtc atg atc tac atg tcc aag gtc gac gac gcc gcc act gcc    336
Gly Pro Val Met Ile Tyr Met Ser Lys Val Asp Asp Ala Ala Thr Ala
                 85                  90                  95 gat ggc tct ggc gac tgg ttc aag gtc gct cag gac acc tac aac ggc    384
Asp Gly Ser Gly Asp Trp Phe Lys Val Ala Gln Asp Thr Tyr Asn Gly
            100                 105                 110 act gag gct agc tgg ggt acc gag atc ctc aac gcc aac tgc ggc aag    432
Thr Glu Ala Ser Trp Gly Thr Glu Ile Leu Asn Ala Asn Cys Gly Lys
        115                 120                 125 cgc gcc ttc acc gtc ccc aag tct ctc ccg tcg ggc gac tac ctc gtc    480
Arg Ala Phe Thr Val Pro Lys Ser Leu Pro Ser Gly Asp Tyr Leu Val
130                 135                 140 cgc gcc gag gcg ctg gcc ctg cac agc gca ggt agc gag ggc ggt gct    528
Arg Ala Glu Ala Leu Ala Leu His Ser Ala Gly Ser Glu Gly Gly Ala
145                 150                 155                 160 cag ttc tac atg agc tgc tac cag gtc acc gtc acc ggc ggc ggc agc    576
Gln Phe Tyr Met Ser Cys Tyr Gln Val Thr Val Thr Gly Gly Gly Ser
                165                 170                 175 gcc acc ccg tcc ccg acc gtc aag ttc cct ggc gcc tac agc gcc gac    624
Ala Thr Pro Ser Pro Thr Val Lys Phe Pro Gly Ala Tyr Ser Ala Asp
            180                 185                 190 gat gct ggt atc ctc atc aac atc tac cag acc ccg ctg acg tac gag    672
Asp Ala Gly Ile Leu Ile Asn Ile Tyr Gln Thr Pro Leu Thr Tyr Glu
        195                 200                 205 gcc cct ggc ccg gct gtc tgg agc ggt aac                            702
Ala Pro Gly Pro Ala Val Trp Ser Gly Asn
    210                 215
```

<210> SEQ ID NO 12
<211> LENGTH: 234
<212> TYPE: PRT
<213> ORGANISM: Botryosphaeria rhodina

<400> SEQUENCE: 12

```
Met Lys Gly Leu Phe Ala Ile Leu Ala Thr Ala Ser Val Val Ser Ala
    -15                 -10                  -5                  -1

His Ala Thr Trp Gln Glu Leu Trp Val Gly Thr Glu Asp Lys Glu Gly
 1               5                  10                  15

Thr Cys Ile Arg Leu Pro Gln Ser Asn Ser Pro Val Thr Asp Val Thr
                20                  25                  30

Ser Asn Asp Ile Arg Cys Asn Ala Ser Pro Ser Ala Ala Ser Thr Thr
            35                  40                  45

Cys Ser Val Ala Ala Gly Gly Ser Leu Thr Val Glu Met His Gln Gln
 50                  55                  60

Pro Asn Asp Arg Ser Cys Asp Asn Glu Ala Ile Gly Gly Asn His Phe
 65              70                  75                  80

Gly Pro Val Met Ile Tyr Met Ser Lys Val Asp Asp Ala Ala Thr Ala
                 85                  90                  95

Asp Gly Ser Gly Asp Trp Phe Lys Val Ala Gln Asp Thr Tyr Asn Gly
            100                 105                 110

Thr Glu Ala Ser Trp Gly Thr Glu Ile Leu Asn Ala Asn Cys Gly Lys
        115                 120                 125

Arg Ala Phe Thr Val Pro Lys Ser Leu Pro Ser Gly Asp Tyr Leu Val
130                 135                 140

Arg Ala Glu Ala Leu Ala Leu His Ser Ala Gly Ser Glu Gly Gly Ala
145                 150                 155                 160
```

```
Gln Phe Tyr Met Ser Cys Tyr Gln Val Thr Val Thr Gly Gly Ser
            165                 170                 175

Ala Thr Pro Ser Pro Thr Val Lys Phe Pro Gly Ala Tyr Ser Ala Asp
        180                 185                 190

Asp Ala Gly Ile Leu Ile Asn Ile Tyr Gln Thr Pro Leu Thr Tyr Glu
            195                 200                 205

Ala Pro Gly Pro Ala Val Trp Ser Gly Asn
        210                 215
```

<210> SEQ ID NO 13
<211> LENGTH: 786
<212> TYPE: DNA
<213> ORGANISM: Botryosphaeria rhodina
<220> FEATURE:
<221> NAME/KEY: CDS
<222> LOCATION: (1)..(786)
<220> FEATURE:
<221> NAME/KEY: transit_peptide
<222> LOCATION: (1)..(39)
<220> FEATURE:
<221> NAME/KEY: misc_feature
<222> LOCATION: (1)..(786)
<223> OTHER INFORMATION: propeptide
<220> FEATURE:
<221> NAME/KEY: mat_peptide
<222> LOCATION: (40)..(786)

<400> SEQUENCE: 13

```
atg ttc ttc tcc caa aag ctc atc gcg gcc gtc gcc gcc ctc ccc gac        48
Met Phe Phe Ser Gln Lys Leu Ile Ala Ala Val Ala Ala Leu Pro Asp
            -10                 -5                  -1   1 cat gac ttc ggc cca cta ctt ctg tcc gca act cat cgt caa cgg cga        96
His Asp Phe Gly Pro Leu Leu Leu Ser Ala Thr His Arg Gln Arg Arg
        5                   10                  15 acc tcc gag caa tgg gaa tac gtc cgc gaa acc tct cag ggc tac gag       144
Thr Ser Glu Gln Trp Glu Tyr Val Arg Glu Thr Ser Gln Gly Tyr Glu
20                  25                  30                  35 ccg caa tac act ccg gac atc ctc acc tcc aac gac ctg cgc tgc aac       192
Pro Gln Tyr Thr Pro Asp Ile Leu Thr Ser Asn Asp Leu Arg Cys Asn
                40                  45                  50 acg gac agc ctc gcc gcc gct gcc aac acc aag gtc gcg tcc gtc gcg       240
Thr Asp Ser Leu Ala Ala Ala Ala Asn Thr Lys Val Ala Ser Val Ala
            55                  60                  65 gcc ggc gac acc gtc tcc ttc gtc acc gac tac ggc gcc aag gtg cag       288
Ala Gly Asp Thr Val Ser Phe Val Thr Asp Tyr Gly Ala Lys Val Gln
        70                  75                  80 cac ccg ggc ccg ctg acg ttc tgg atg tcg cag gcg ccg ggc ggg gat       336
His Pro Gly Pro Leu Thr Phe Trp Met Ser Gln Ala Pro Gly Gly Asp
    85                  90                  95 gta acc aca tac gat ggc tca ggc gat tgg ttc aag atc ggc gtc gtg       384
Val Thr Thr Tyr Asp Gly Ser Gly Asp Trp Phe Lys Ile Gly Val Val
100                 105                 110                 115 ggc tac gac acg ccg ttc gac tcg acg gga acg aac tgg cgc gcc tac       432
Gly Tyr Asp Thr Pro Phe Asp Ser Thr Gly Thr Asn Trp Arg Ala Tyr
                120                 125                 130 gat gag ggc acg ttc aac gtg tcc atc ccg aca acg gtg ccg aat ggc       480
Asp Glu Gly Thr Phe Asn Val Ser Ile Pro Thr Thr Val Pro Asn Gly
            135                 140                 145 caa tac ttg ctg cgc atc gag cat atc ggc ctg cac cgc ccg tcg acg       528
Gln Tyr Leu Leu Arg Ile Glu His Ile Gly Leu His Arg Pro Ser Thr
        150                 155                 160 cgc gag atg ttc ttc aac tgc gcg cag gtt gag gtg acg ggg tcg tcc       576
Arg Glu Met Phe Phe Asn Cys Ala Gln Val Glu Val Thr Gly Ser Ser
```

```
                165                 170                 175
gcc aca gcg gtg ccg agt gag acg gcg aag att cct gcg gga tct ata    624
Ala Thr Ala Val Pro Ser Glu Thr Ala Lys Ile Pro Ala Gly Ser Ile
180                 185                 190                 195 gtg aga gcg atg agt ggg tgt cca agt gga gca tgt ata gta gcc cga    672
Val Arg Ala Met Ser Gly Cys Pro Ser Gly Ala Cys Ile Val Ala Arg
                200                 205                 210 gca gct tcc cgt act ctg gcc cag cta ctg ttg atg gtg gtg ttt ttg    720
Ala Ala Ser Arg Thr Leu Ala Gln Leu Leu Leu Met Val Val Phe Leu
            215                 220                 225 att ctc agg gct ctg att ctg ctt aaa tgg gcg gga ttt tcc ctt tcc    768
Ile Leu Arg Ala Leu Ile Leu Leu Lys Trp Ala Gly Phe Ser Leu Ser
        230                 235                 240 ata tgt tct att gtt gta                                            786
Ile Cys Ser Ile Val Val
        245

<210> SEQ ID NO 14
<211> LENGTH: 262
<212> TYPE: PRT
<213> ORGANISM: Botryosphaeria rhodina

<400> SEQUENCE: 14

Met Phe Phe Ser Gln Lys Leu Ile Ala Ala Val Ala Ala Leu Pro Asp
                -10                  -5                  -1   1

His Asp Phe Gly Pro Leu Leu Leu Ser Ala Thr His Arg Gln Arg Arg
             5                  10                  15

Thr Ser Glu Gln Trp Glu Tyr Val Arg Glu Thr Ser Gln Gly Tyr Glu
 20                  25                  30                  35

Pro Gln Tyr Thr P

<210> SEQ ID NO 15
<211> LENGTH: 819
<212> TYPE: DNA
<213> ORGANISM: Botryosphaeria rhodina
<220> FEATURE:
<221> NAME/KEY: CDS
<222> LOCATION: (1)..(819)
<220> FEATURE:
<221> NAME/KEY: transit_peptide
<222> LOCATION: (1)..(54)
<220> FEATURE:
<221> NAME/KEY: misc_feature
<222> LOCATION: (1)..(819)
<223> OTHER INFORMATION: propeptide
<220> FEATURE:
<221> NAME/KEY: mat_peptide
<222> LOCATION: (55)..(819)

<400> SEQUENCE: 15

| | | | | | | | | | | | | | | | | |
|---|---|---|---|---|---|---|---|---|---|---|---|---|---|---|---|---|
| atg | tct | ttc | aag | tct | ctt | gct | gtt | att | gcc | gct | ggt | gcg | gcc | acc | gcc | 48 |
| Met | Ser | Phe | Lys | Ser | Leu | Ala | Val | Ile | Ala | Ala | Gly | Ala | Ala | Thr | Ala | |
| | | | -15 | | | | -10 | | | | | -5 | | | | |

| aac | gcc | cac | ggt | gtc | atc | ctg | gac | atc | gtg | tct | ggc | ggc | aag | acc | tac | 96 |
|---|---|---|---|---|---|---|---|---|---|---|---|---|---|---|---|---|
| Asn | Ala | His | Gly | Val | Ile | Leu | Asp | Ile | Val | Ser | Gly | Gly | Lys | Thr | Tyr | |
| -1 | 1 | | | | 5 | | | | | 10 | | | | | | |

| ggt | ggc | tgg | gac | gcc | agc | tac | gtc | tac | tac | aac | ccc | gtc | ccc | gag | gtt | 144 |
|---|---|---|---|---|---|---|---|---|---|---|---|---|---|---|---|---|
| Gly | Gly | Trp | Asp | Ala | Ser | Tyr | Val | Tyr | Tyr | Asn | Pro | Val | Pro | Glu | Val | |
| 15 | | | | | 20 | | | | | 25 | | | | | 30 | |

| gct | gcc | tgg | cag | tct | ggt | ggc | ttc | ggc | cac | ggc | ccc | atc | gtc | ggc | acc | 192 |
|---|---|---|---|---|---|---|---|---|---|---|---|---|---|---|---|---|
| Ala | Ala | Trp | Gln | Ser | Gly | Gly | Phe | Gly | His | Gly | Pro | Ile | Val | Gly | Thr | |
| | | | | 35 | | | | | 40 | | | | | 45 | | |

| cag | tac | tcg | acc | gct | tcc | atc | aac | tgc | cac | gac | gac | gct | att | gcc | gct | 240 |
|---|---|---|---|---|---|---|---|---|---|---|---|---|---|---|---|---|
| Gln | Tyr | Ser | Thr | Ala | Ser | Ile | Asn | Cys | His | Asp | Asp | Ala | Ile | Ala | Ala | |
| | | 50 | | | | | 55 | | | | | 60 | | | | |

| ccc | atc | tac | atg | gag | gcc | gcc | gcc | ggt | gac | gag | atc | gcc | atc | tcc | tgg | 288 |
|---|---|---|---|---|---|---|---|---|---|---|---|---|---|---|---|---|
| Pro | Ile | Tyr | Met | Glu | Ala | Ala | Ala | Gly | Asp | Glu | Ile | Ala | Ile | Ser | Trp | |
| | | 65 | | | | | 70 | | | | | 75 | | | | |

| ggt | acc | cct | ggc | aac | ccc | ccc | agc | gcc | tgg | ccc | acg | agc | cac | cac | ggc | 336 |
|---|---|---|---|---|---|---|---|---|---|---|---|---|---|---|---|---|
| Gly | Thr | Pro | Gly | Asn | Pro | Pro | Ser | Ala | Trp | Pro | Thr | Ser | His | His | Gly | |
| 80 | | | | | 85 | | | | | 90 | | | | | | |

| ccc | atc | att | acc | tac | atg | gct | cct | tgc | ggt | ggt | gct | gat | gct | act | ggc | 384 |
|---|---|---|---|---|---|---|---|---|---|---|---|---|---|---|---|---|
| Pro | Ile | Ile | Thr | Tyr | Met | Ala | Pro | Cys | Gly | Gly | Ala | Asp | Ala | Thr | Gly | |
| 95 | | | | | 100 | | | | | 105 | | | | | 110 | |

| gac | tgc | acc | tcc | ctg | aac | gtc | acc | gac | ctc | gct | tgg | acc | aag | gtc | tac | 432 |
|---|---|---|---|---|---|---|---|---|---|---|---|---|---|---|---|---|
| Asp | Cys | Thr | Ser | Leu | Asn | Val | Thr | Asp | Leu | Ala | Trp | Thr | Lys | Val | Tyr | |
| | | | | 115 | | | | | 120 | | | | | 125 | | |

| cag | aag | ggt | ctc | atc | acc | ggc | ggt | gat | gtt | gac | agc | cag | gtc | tgg | gcc | 480 |
|---|---|---|---|---|---|---|---|---|---|---|---|---|---|---|---|---|
| Gln | Lys | Gly | Leu | Ile | Thr | Gly | Gly | Asp | Val | Asp | Ser | Gln | Val | Trp | Ala | |
| | | | 130 | | | | | 135 | | | | | 140 | | | |

| acc | gac | gag | ctc | atc | tcg | aac | aac | aag | acc | atg | gtc | acc | atc | ccc | tcc | 528 |
|---|---|---|---|---|---|---|---|---|---|---|---|---|---|---|---|---|
| Thr | Asp | Glu | Leu | Ile | Ser | Asn | Asn | Lys | Thr | Met | Val | Thr | Ile | Pro | Ser | |
| | | | 145 | | | | | 150 | | | | | 155 | | | |

| tcg | ctc | gcc | ccg | ggc | aac | tac | gtc | ctc | cgc | aac | gag | atc | atc | gcc | ctt | 576 |
|---|---|---|---|---|---|---|---|---|---|---|---|---|---|---|---|---|
| Ser | Leu | Ala | Pro | Gly | Asn | Tyr | Val | Leu | Arg | Asn | Glu | Ile | Ile | Ala | Leu | |
| | | 160 | | | | | 165 | | | | | 170 | | | | |

| cac | gcc | ggc | ggt | gag | gtc | aac | ggc | ccc | cag | aac | tac | ccc | cag | tgc | tac | 624 |
|---|---|---|---|---|---|---|---|---|---|---|---|---|---|---|---|---|
| His | Ala | Gly | Gly | Glu | Val | Asn | Gly | Pro | Gln | Asn | Tyr | Pro | Gln | Cys | Tyr | |
| 175 | | | | | 180 | | | | | 185 | | | | | 190 | |

| aac | gtc | aag | atc | acc | ggc | tct | ggc | tcc | gga | aag | ctt | acc | gac | ggc | gtc | 672 |
|---|---|---|---|---|---|---|---|---|---|---|---|---|---|---|---|---|
| Asn | Val | Lys | Ile | Thr | Gly | Ser | Gly | Ser | Gly | Lys | Leu | Thr | Asp | Gly | Val | |
| | | | | 195 | | | | | 200 | | | | | 205 | | |

| aag | ggc | acc | gag | ctc | tac | acc | ccc | gag | gac | acc | gtc | ttc | aac | atc | tac | 720 |
|---|---|---|---|---|---|---|---|---|---|---|---|---|---|---|---|---|
| Lys | Gly | Thr | Glu | Leu | Tyr | Thr | Pro | Glu | Asp | Thr | Val | Phe | Asn | Ile | Tyr | |

```
                        210                 215                 220
gcc aac att gac agc tac ccc ttc ccc ggc ccc gag ctc tgg agc ggc         768
Ala Asn Ile Asp Ser Tyr Pro Phe Pro Gly Pro Glu Leu Trp Ser Gly
        225                 230                 235 gct tcc tct acc tcc aac gcc acc aag cgc tct ttc cgt acc ttc aag         816
Ala Ser Ser Thr Ser Asn Ala Thr Lys Arg Ser Phe Arg Thr Phe Lys
240                 245                 250 gca                                                                     819
Ala
255

<210> SEQ ID NO 16
<211> LENGTH: 273
<212> TYPE: PRT
<213> ORGANISM: Botryosphaeria rhodina

<400> SEQUENCE: 16

Met Ser Phe Lys Ser Leu Ala Val Ile Ala Ala Gly Ala Ala Thr Ala
            -15                 -10                  -5

Asn Ala His Gly Val Ile Leu Asp Ile Val Ser Gly Gly Lys Thr Tyr
 -1  1               5                  10

Gly Gly Trp Asp Ala Ser Tyr Val Tyr Tyr Asn Pro Val Pro Glu Val
 15                  20                  25                  30

Ala Ala Trp Gln Ser Gly Gly Phe Gly His Gly Pro Ile Val Gly Thr
                 35                  40                  45

Gln Tyr Ser Thr Ala Ser Ile Asn Cys His Asp Asp Ala Ile Ala Ala
             50                  55                  60

Pro Ile Tyr Met Glu Ala Ala Gly Asp Glu Ile Ala Ile Ser Trp
 65                  70                  75

Gly Thr Pro Gly Asn Pro Pro Ser Ala Trp Pro Thr Ser His His Gly
 80                  85                  90

Pro Ile Ile Thr Tyr Met Ala Pro Cys Gly Gly Ala Asp Ala Thr Gly
 95                 100                 105                 110

Asp Cys Thr Ser Leu Asn Val Thr Asp Leu Ala Trp Thr Lys Val Tyr
                115                 120                 125

Gln Lys Gly Leu Ile Thr Gly Gly Asp Val Asp Ser Gln Val Trp Ala
            130                 135                 140

Thr Asp Glu Leu Ile Ser Asn Asn Lys Thr Met Val Thr Ile Pro Ser
            145                 150                 155

Ser Leu Ala Pro Gly Asn Tyr Val Leu Arg Asn Glu Ile Ile Ala Leu
160                 165                 170

His Ala Gly Gly Glu Val Asn Gly Pro Gln Asn Tyr Pro Gln Cys Tyr
175                 180                 185                 190

Asn Val Lys Ile Thr Gly Ser Gly Ser Gly Lys Leu Thr Asp Gly Val
                195                 200                 205

Lys Gly Thr Glu Leu Tyr Thr Pro Glu Asp Thr Val Phe Asn Ile Tyr
            210                 215                 220

Ala Asn Ile Asp Ser Tyr Pro Phe Pro Gly Pro Glu Leu Trp Ser Gly
            225                 230                 235

Ala Ser Ser Thr Ser Asn Ala Thr Lys Arg Ser Phe Arg Thr Phe Lys
240                 245                 250

Ala
255

<210> SEQ ID NO 17
<211> LENGTH: 675
<212> TYPE: DNA
```

<213> ORGANISM: Botryosphaeria rhodina
<220> FEATURE:
<221> NAME/KEY: CDS
<222> LOCATION: (1)..(675)
<220> FEATURE:
<221> NAME/KEY: sig_peptide
<222> LOCATION: (1)..(60)
<220> FEATURE:
<221> NAME/KEY: misc_feature
<222> LOCATION: (1)..(675)
<223> OTHER INFORMATION: propeptide
<220> FEATURE:
<221> NAME/KEY: mat_peptide
<222> LOCATION: (61)..(675)

<400> SEQUENCE: 17

| atg | aag | act | ttc | act | act | ttc | gca | ttc | gct | gcc | tct | gtg | ctg | gca | cag | 48 |
| Met | Lys | Thr | Phe | Thr | Thr | Phe | Ala | Phe | Ala | Ala | Ser | Val | Leu | Ala | Gln | |
| -20 | | | | -15 | | | | -10 | | | | | -5 | | | |

| gct | gtc | aac | gga | cac | tac | atc | ttc | caa | tac | ctc | act | gcc | aac | ggc | gtg | 96 |
| Ala | Val | Asn | Gly | His | Tyr | Ile | Phe | Gln | Tyr | Leu | Thr | Ala | Asn | Gly | Val | |
| | | -1 | 1 | | | | 5 | | | | | 10 | | | | |

| aag | ggt | ggt | atc | tat | cag | aac | att | agg | gag | aac | acg | aac | aac | aac | tcg | 144 |
| Lys | Gly | Gly | Ile | Tyr | Gln | Asn | Ile | Arg | Glu | Asn | Thr | Asn | Asn | Asn | Ser | |
| | | 15 | | | | | 20 | | | | | 25 | | | | |

| ccc | gtg | act | gat | ctc | gag | tcc | aac | gac | ctc | cgc | tgc | aat | gtt | ggt | ggt | 192 |
| Pro | Val | Thr | Asp | Leu | Glu | Ser | Asn | Asp | Leu | Arg | Cys | Asn | Val | Gly | Gly | |
| 30 | | | | | 35 | | | | | 40 | | | | | | |

| gag | gat | ggc | agc | aag | act | agc | acg | gtc | tcc | gtc | gct | gct | ggc | agc | acc | 240 |
| Glu | Asp | Gly | Ser | Lys | Thr | Ser | Thr | Val | Ser | Val | Ala | Ala | Gly | Ser | Thr | |
| 45 | | | | | 50 | | | | | 55 | | | | | 60 | |

| gtc | gct | ttc | act | gcc | gac | atc | gcc | gtg | tac | cac | cag | ggc | ccc | gtc | tct | 288 |
| Val | Ala | Phe | Thr | Ala | Asp | Ile | Ala | Val | Tyr | His | Gln | Gly | Pro | Val | Ser | |
| | | | | 65 | | | | | 70 | | | | | 75 | | |

| ttc | tac | atg | aca | aag | gtc | gac | gac | gcg | gcg | gcg | gcg | gac | ggc | agc | acg | 336 |
| Phe | Tyr | Met | Thr | Lys | Val | Asp | Asp | Ala | Ala | Ala | Ala | Asp | Gly | Ser | Thr | |
| | | | 80 | | | | | 85 | | | | | 90 | | | |

| ccg | tgg | ttt | aag | atc | aag | gac | atc | gga | ccc | act | ttc | tcc | aac | ggc | cag | 384 |
| Pro | Trp | Phe | Lys | Ile | Lys | Asp | Ile | Gly | Pro | Thr | Phe | Ser | Asn | Gly | Gln | |
| | | | 95 | | | | | 100 | | | | | 105 | | | |

| gcg | act | tgg | gac | ctc | gag | acg | acg | tac | aac | gtg | acc | atc | ccc | aac | tgc | 432 |
| Ala | Thr | Trp | Asp | Leu | Glu | Thr | Thr | Tyr | Asn | Val | Thr | Ile | Pro | Asn | Cys | |
| | | 110 | | | | | 115 | | | | | 120 | | | | |

| ctt | ccc | gcc | ggc | gag | tac | ctg | ctg | cgc | atc | cag | cag | ctt | ggc | atc | cac | 480 |
| Leu | Pro | Ala | Gly | Glu | Tyr | Leu | Leu | Arg | Ile | Gln | Gln | Leu | Gly | Ile | His | |
| 125 | | | | | 130 | | | | | 135 | | | | | 140 | |

| aac | ccg | tgg | ccg | gcc | ggc | atc | ccg | caa | ttc | tac | atc | tcg | tgc | gcc | cag | 528 |
| Asn | Pro | Trp | Pro | Ala | Gly | Ile | Pro | Gln | Phe | Tyr | Ile | Ser | Cys | Ala | Gln | |
| | | | | 145 | | | | | 150 | | | | | 155 | | |

| gtc | aag | gtc | acg | ggc | agc | ggc | tcg | ggc | tcg | ccc | agc | ccg | act | gtt | tcc | 576 |
| Val | Lys | Val | Thr | Gly | Ser | Gly | Ser | Gly | Ser | Pro | Ser | Pro | Thr | Val | Ser | |
| | | | 160 | | | | | 165 | | | | | 170 | | | |

| atc | ccc | ggc | gcg | ttc | aag | gag | acg | gac | ccc | ggc | tat | acc | gtc | aac | att | 624 |
| Ile | Pro | Gly | Ala | Phe | Lys | Glu | Thr | Asp | Pro | Gly | Tyr | Thr | Val | Asn | Ile | |
| | | 175 | | | | | 180 | | | | | 185 | | | | |

| tac | aac | gac | ttc | acc | aac | tat | act | gtc | ccc | ggc | ccg | gag | gtg | tgg | acg | 672 |
| Tyr | Asn | Asp | Phe | Thr | Asn | Tyr | Thr | Val | Pro | Gly | Pro | Glu | Val | Trp | Thr | |
| | 190 | | | | | 195 | | | | | 200 | | | | | |

| tgc | | | | | | | | | | | | | | | | 675 |
| Cys | | | | | | | | | | | | | | | | |
| 205 | | | | | | | | | | | | | | | | |

<210> SEQ ID NO 18
<211> LENGTH: 225

<212> TYPE: PRT
<213> ORGANISM: Botryosphaeria rhodina

<400> SEQUENCE: 18

```
Met Lys Thr Phe Thr Thr Phe Ala Phe Ala Ala Ser Val Leu Ala Gln
-20             -15                 -10                  -5

Ala Val Asn Gly His Tyr Ile Phe Gln Tyr Leu Thr Ala Asn Gly Val
             -1  1              5                  10

Lys Gly Gly Ile Tyr Gln Asn Ile Arg Glu Asn Thr Asn Asn Ser
         15              20                  25

Pro Val Thr Asp Leu Glu Ser Asn Asp Leu Arg Cys Asn Val Gly Gly
         30              35                  40

Glu Asp Gly Ser Lys Thr Ser Thr Val Ser Val Ala Ala Gly Ser Thr
45              50                  55                  60

Val Ala Phe Thr Ala Asp Ile Ala Val Tyr His Gln Gly Pro Val Ser
                 65                  70                  75

Phe Tyr Met Thr Lys Val Asp Asp Ala Ala Ala Asp Gly Ser Thr
             80                  85                  90

Pro Trp Phe Lys Ile Lys Asp Ile Gly Pro Thr Phe Ser Asn Gly Gln
             95                  100                 105

Ala Thr Trp Asp Leu Glu Thr Thr Tyr Asn Val Thr Ile Pro Asn Cys
     110                 115                 120

Leu Pro Ala Gly Glu Tyr Leu Leu Arg Ile Gln Gln Leu Gly Ile His
125                 130                 135                 140

Asn Pro Trp Pro Ala Gly Ile Pro Gln Phe Tyr Ile Ser Cys Ala Gln
                 145                 150                 155

Val Lys Val Thr Gly Ser Gly Ser Gly Ser Pro Ser Pro Thr Val Ser
                 160                 165                 170

Ile Pro Gly Ala Phe Lys Glu Thr Asp Pro Gly Tyr Thr Val Asn Ile
             175                 180                 185

Tyr Asn Asp Phe Thr Asn Tyr Thr Val Pro Gly Pro Glu Val Trp Thr
     190                 195                 200

Cys
205
```

<210> SEQ ID NO 19
<211> LENGTH: 729
<212> TYPE: DNA
<213> ORGANISM: Botryosphaeria rhodina
<220> FEATURE:
<221> NAME/KEY: CDS
<222> LOCATION: (1)..(729)

<400> SEQUENCE: 19

```
atg gag tcg gcg tcc aag acg ctg aag cgc gtg acg ctt gag ctg ggt    48
Met Glu Ser Ala Ser Lys Thr Leu Lys Arg Val Thr Leu Glu Leu Gly
1               5                   10                  15 ggc aag gac ccg gcc atc gtg tgc tcg gac gtg gac atc gcg gcg acg    96
Gly Lys Asp Pro Ala Ile Val Cys Ser Asp Val Asp Ile Ala Ala Thr
            20                  25                  30 gcc ccc aag gtt gcc acc ctg gcc ttc ctc aac tcg ggt cag atc tgc   144
Ala Pro Lys Val Ala Thr Leu Ala Phe Leu Asn Ser Gly Gln Ile Cys
        35                  40                  45 ctg gcc atc aag cgt atc tac gtt cac gag aag atc tac gac gag ttc   192
Leu Ala Ile Lys Arg Ile Tyr Val His Glu Lys Ile Tyr Asp Glu Phe
    50                  55                  60 ctc aag gcg tgc gtc gag cac acc aag acg ctc gtg ctc ggc aac ggc   240
Leu Lys Ala Cys Val Glu His Thr Lys Thr Leu Val Leu Gly Asn Gly
65                  70                  75                  80
```

```
acc gag ccc aac acc ttc ctc ggc ccc gtg cag aac gcc atg cag tac      288
Thr Glu Pro Asn Thr Phe Leu Gly Pro Val Gln Asn Ala Met Gln Tyr
                85                  90                  95 gag cgc gtc aag ggc ttc ttc cag gac gtg cac gag cac aag atg aag      336
Glu Arg Val Lys Gly Phe Phe Gln Asp Val His Glu His Lys Met Lys
            100                 105                 110 gtg gcc gtc ggc ggc gtc aac gac aag acg ggc ggc tac tac atc acc      384
Val Ala Val Gly Gly Val Asn Asp Lys Thr Gly Gly Tyr Tyr Ile Thr
        115                 120                 125 ccg acc atc atc gac aac ccg gcc gag acg agc aag atc gtg acc gag      432
Pro Thr Ile Ile Asp Asn Pro Ala Glu Thr Ser Lys Ile Val Thr Glu
    130                 135                 140 gag ccc ttc ggc ccc atc gtg ccg ctg ctc aag tgg agc gac gag agc      480
Glu Pro Phe Gly Pro Ile Val Pro Leu Leu Lys Trp Ser Asp Glu Ser
145                 150                 155                 160 gag gtc gtc cac cgc gcc aac gac acc aag atg ggt ctc ggc gcc tcc      528
Glu Val Val His Arg Ala Asn Asp Thr Lys Met Gly Leu Gly Ala Ser
                165                 170                 175 gtg tgg agc aac gac ctc gcc cag gcc gag cgc atc gcc cgc cag ctc      576
Val Trp Ser Asn Asp Leu Ala Gln Ala Glu Arg Ile Ala Arg Gln Leu
            180                 185                 190 gac gcc ggc agc gtc tgg atc aac act cac ctc gag ctc gac ccc aac      624
Asp Ala Gly Ser Val Trp Ile Asn Thr His Leu Glu Leu Asp Pro Asn
        195                 200                 205 gct ccc ttc ggc ggc cac aag gag agc ggt gtt ggc tac gag tgg ggt      672
Ala Pro Phe Gly Gly His Lys Glu Ser Gly Val Gly Tyr Glu Trp Gly
    210                 215                 220 ctt ggt ggc atg aag gcc tac tgc aac gtc cag acc ctg ttc ttg aag      720
Leu Gly Gly Met Lys Ala Tyr Cys Asn Val Gln Thr Leu Phe Leu Lys
225                 230                 235                 240 aag aag gtc                                                          729
Lys Lys Val <210> SEQ ID NO 20
<211> LENGTH: 243
<212> TYPE: PRT
<213> ORGANISM: Botryosphaeria rhodina

<400> SEQUENCE: 20

Met Glu Ser Ala Ser Lys Thr Leu Lys Arg Val Thr Leu Glu Leu Gly
1               5                   10                  15

Gly Lys Asp Pro Ala Ile Val Cys Ser Asp Val Asp Ile Ala Ala Thr
            20                  25                  30

Ala Pro Lys Val Ala Thr Leu Ala Phe Leu Asn Ser Gly Gln Ile Cys
        35                  40                  45

Leu Ala Ile Lys Arg Ile Tyr Val His Glu Lys Ile Tyr Asp Glu Phe
    50                  55                  60

Leu Lys Ala Cys Val Glu His Thr Lys Thr Leu Val Leu Gly Asn Gly
65                  70                  75                  80

Thr Glu Pro Asn Thr Phe Leu Gly Pro Val Gln Asn Ala Met Gln Tyr
                85                  90                  95

Glu Arg Val Lys Gly Phe Phe Gln Asp Val His Glu His Lys Met Lys
            100                 105                 110

Val Ala Val Gly Gly Val Asn Asp Lys Thr Gly Gly Tyr Tyr Ile Thr
        115                 120                 125

Pro Thr Ile Ile Asp Asn Pro Ala Glu Thr Ser Lys Ile Val Thr Glu
    130                 135                 140

Glu Pro Phe Gly Pro Ile Val Pro Leu Leu Lys Trp Ser Asp Glu Ser
```

```
                145                 150                 155                 160
Glu Val Val His Arg Ala Asn Asp Thr Lys Met Gly Leu Gly Ala Ser
                    165                 170                 175

Val Trp Ser Asn Asp Leu Ala Gln Ala Glu Arg Ile Ala Arg Gln Leu
                180                 185                 190

Asp Ala Gly Ser Val Trp Ile Asn Thr His Leu Glu Leu Asp Pro Asn
            195                 200                 205

Ala Pro Phe Gly Gly His Lys Glu Ser Gly Val Gly Tyr Glu Trp Gly
        210                 215                 220

Leu Gly Gly Met Lys Ala Tyr Cys Asn Val Gln Thr Leu Phe Leu Lys
225                 230                 235                 240

Lys Lys Val

<210> SEQ ID NO 21
<211> LENGTH: 1300
<212> TYPE: DNA
<213> ORGANISM: Botryosphaeria rhodina
<220> FEATURE:
<221> NAME/KEY: CDS
<222> LOCATION: (1)..(1299)
<220> FEATURE:
<221> NAME/KEY: sig_peptide
<222> LOCATION: (1)..(54)
<220> FEATURE:
<221> NAME/KEY: mat_peptide
<222> LOCATION: (55)..(1299)
<220> FEATURE:
<221> NAME/KEY: misc_feature
<222> LOCATION: (55)..(456)
<223> OTHER INFORMATION: Unknown domain
<220> FEATURE:
<221> NAME/KEY: misc_feature
<222> LOCATION: (460)..(579)
<223> OTHER INFORMATION: Chitin binding domain
<220> FEATURE:
<221> NAME/KEY: misc_feature
<222> LOCATION: (580)..(1299)
<223> OTHER INFORMATION: threonin-serine rich domain

<400> SEQUENCE: 21 atg aag ttg gcg gcg tcg ctt ttg ctt gtc gca gcc gcg ctt gcg ggg      48
Met Lys Leu Ala Ala Ser Leu Leu Leu Val Ala Ala Leu Ala Gly
                -15                 -10                 -5 gcc ttt gac aac cgc caa tcg cat gca agg gcc ccc gtt ccg cga gac      96
Ala Phe Asp Asn Arg Gln Ser His Ala Arg Ala Pro Val Pro Arg Asp
    -1   1               5                   10 gcc ttc gac aat gct tgc gag acc gtc tac atc acg agt tat gtc tgc     144
Ala Phe Asp Asn Ala Cys Glu Thr Val Tyr Ile Thr Ser Tyr Val Cys
15                  20                  25                  30 acc acc ttc gtc gtc cct tcg ctt agc tac acc agc cat gag ttt agc     192
Thr Thr Phe Val Val Pro Ser Leu Ser Tyr Thr Ser His Glu Phe Ser
                35                  40                  45 tgc acc act cac ttg acc aac acc acg cgt atc aca tct tcc gga tcc     240
Cys Thr Thr His Leu Thr Asn Thr Thr Arg Ile Thr Ser Ser Gly Ser
            50                  55                  60 acg acc gca gaa act tta act tca ggt cac acg agc tca gag agc cgc     288
Thr Thr Ala Glu Thr Leu Thr Ser Gly His Thr Ser Ser Glu Ser Arg
        65                  70                  75 gct att agc ccg aca caa aac tca tcc agc gtt tac ccg agc gac agc     336
Ala Ile Ser Pro Thr Gln Asn Ser Ser Ser Val Tyr Pro Ser Asp Ser
    80                  85                  90 cct tca cgt tct gtg tct tca tcc aca ctg tcg cag tct tcc aga acc     384
Pro Ser Arg Ser Val Ser Ser Ser Thr Leu Ser Gln Ser Ser Arg Thr
95                  100                 105                 110
```

```
gaa aca agc aat aga gac acg agc aat acg tct cac agc gac agc cct    432
Glu Thr Ser Asn Arg Asp Thr Ser Asn Thr Ser His Ser Asp Ser Pro
            115                 120                 125 act ccc ggc ccc agc gag gag ccc tgt tgc ggc ccg caa ggc ggt aac    480
Thr Pro Gly Pro Ser Glu Glu Pro Cys Cys Gly Pro Gln Gly Gly Asn
        130                 135                 140 cgt cgt tgt ccc cat gga aca tgc tgt tcc aaa aat gga cac tgt ggt    528
Arg Arg Cys Pro His Gly Thr Cys Cys Ser Lys Asn Gly His Cys Gly
            145                 150                 155 tcg ggg cca gat ttc tgt ggt gat ggg tgc caa tct tcg tgg gga aac    576
Ser Gly Pro Asp Phe Cys Gly Asp Gly Cys Gln Ser Ser Trp Gly Asn
        160                 165                 170 tgt acc aac gac aac agc gat gag ata tct ccc tcg agc agt ccc tca    624
Cys Thr Asn Asp Asn Ser Asp Glu Ile Ser Pro Ser Ser Ser Pro Ser
175                 180                 185                 190 aac tac tcg gcg cca gct gca tgg gct cga gtg aaa aga gat gag ttt    672
Asn Tyr Ser Ala Pro Ala Ala Trp Ala Arg Val Lys Arg Asp Glu Phe
            195                 200                 205 gac gca ggt gca ttt gaa ctc ttg aca agt ctc aag tac atc gtt gaa    720
Asp Ala Gly Ala Phe Glu Leu Leu Thr Ser Leu Lys Tyr Ile Val Glu
        210                 215                 220 ggc acc atg gtg aga acc agc act tgc act tac act cac tgg cac acc    768
Gly Thr Met Val Arg Thr Ser Thr Cys Thr Tyr Thr His Trp His Thr
            225                 230                 235 atc tcg act aca tca aag cga acg agt acc atc acc gtc tac att tcg    816
Ile Ser Thr Thr Ser Lys Arg Thr Ser Thr Ile Thr Val Tyr Ile Ser
        240                 245                 250 acg tgt cta tca tca aat cca cca gtc acc agc agc agc aca cag tcc    864
Thr Cys Leu Ser Ser Asn Pro Pro Val Thr Ser Ser Ser Thr Gln Ser
255                 260                 265                 270 atc tcc tct ctc atc aca tct cct acg ttg gtg tca act tcg agt gtc    912
Ile Ser Ser Leu Ile Thr Ser Pro Thr Leu Val Ser Thr Ser Ser Val
            275                 280                 285 att acg aca tcc agc aca tcc caa tac tca agc agt acc tca tgc acc    960
Ile Thr Thr Ser Ser Thr Ser Gln Tyr Ser Ser Ser Thr Ser Cys Thr
        290                 295                 300 tat aca aaa agt tca aac act aca ata ccg tgg tca cca ccc aca agc   1008
Tyr Thr Lys Ser Ser Asn Thr Thr Ile Pro Trp Ser Pro Pro Thr Ser
            305                 310                 315 atg tcg ata acc agc tct tca tgc act cgc tca tcg gac tgg aca acc   1056
Met Ser Ile Thr Ser Ser Ser Cys Thr Arg Ser Ser Asp Trp Thr Thr
        320                 325                 330 cca aag ccg cca ccc tcg acc tca aca acc ata caa acg aca caa acc   1104
Pro Lys Pro Pro Pro Ser Thr Ser Thr Thr Ile Gln Thr Thr Gln Thr
335                 340                 345                 350 ccg gat act ata acg aaa tcg aat act ccc act acg acc aag acc aca   1152
Pro Asp Thr Ile Thr Lys Ser Asn Thr Pro Thr Thr Thr Lys Thr Thr
            355                 360                 365 act aag atc tcg att tca att tcc act cca tgg aat act aca tgt acc   1200
Thr Lys Ile Ser Ile Ser Ile Ser Thr Pro Trp Asn Thr Thr Cys Thr
        370                 375                 380 tca tca acg aac agc acc aca tcc aca ccc caa acc aca cat aca gcg   1248
Ser Ser Thr Asn Ser Thr Thr Ser Thr Pro Gln Thr Thr His Thr Ala
            385                 390                 395 aca gaa cca ccc act tcc agc atc ata gca ata tca agc tcc tct aac   1296
Thr Glu Pro Pro Thr Ser Ser Ile Ile Ala Ile Ser Ser Ser Ser Asn
        400                 405                 410 ccg c                                                              1300
Pro
415
```

<210> SEQ ID NO 22
<211> LENGTH: 433
<212> TYPE: PRT
<213> ORGANISM: Botryosphaeria rhodina

<400> SEQUENCE: 22

```
Met Lys Leu Ala Ala Ser Leu Leu Val Ala Ala Leu Ala Gly
            -15                 -10                  -5

Ala Phe Asp Asn Arg Gln Ser His Ala Arg Ala Pro Val Pro Arg Asp
    -1   1                   5                  10

Ala Phe Asp Asn Ala Cys Glu Thr Val Tyr Ile Thr Ser Tyr Val Cys
 15              20                  25                      30

Thr Thr Phe Val Val Pro Ser Leu Ser Tyr Thr Ser His Glu Phe Ser
                 35                  40                  45

Cys Thr Thr His Leu Thr Asn Thr Thr Arg Ile Thr Ser Ser Gly Ser
                 50                  55                  60

Thr Thr Ala Glu Thr Leu Thr Ser Gly His Thr Ser Ser Glu Ser Arg
             65                  70                  75

Ala Ile Ser Pro Thr Gln Asn Ser Ser Ser Val Tyr Pro Ser Asp Ser
 80                  85                  90

Pro Ser Arg Ser Val Ser Ser Ser Thr Leu Ser Gln Ser Ser Arg Thr
 95                 100                 105                 110

Glu Thr Ser Asn Arg Asp Thr Ser Asn Thr Ser His Ser Asp Ser Pro
                115                 120                 125

Thr Pro Gly Pro Ser Glu Glu Pro Cys Cys Gly Pro Gln Gly Gly Asn
            130                 135                 140

Arg Arg Cys Pro His Gly Thr Cys Cys Ser Lys Asn Gly His Cys Gly
            145                 150                 155

Ser Gly Pro Asp Phe Cys Gly Asp Gly Cys Gln Ser Ser Trp Gly Asn
            160                 165                 170

Cys Thr Asn Asp Asn Ser Asp Glu Ile Ser Pro Ser Ser Ser Pro Ser
175                 180                 185                 190

Asn Tyr Ser Ala Pro Ala Ala Trp Ala Arg Val Lys Arg Asp Glu Phe
                195                 200                 205

Asp Ala Gly Ala Phe Glu Leu Leu Thr Ser Leu Lys Tyr Ile Val Glu
            210                 215                 220

Gly Thr Met Val Arg Thr Ser Thr Cys Thr Tyr Thr His Trp His Thr
            225                 230                 235

Ile Ser Thr Thr Ser Lys Arg Thr Ser Thr Ile Thr Val Tyr Ile Ser
    240                 245                 250

Thr Cys Leu Ser Ser Asn Pro Pro Val Thr Ser Ser Ser Thr Gln Ser
255                 260                 265                 270

Ile Ser Ser Leu Ile Thr Ser Pro Thr Leu Val Ser Thr Ser Ser Val
                275                 280                 285

Ile Thr Thr Ser Ser Thr Ser Gln Tyr Ser Ser Ser Thr Ser Cys Thr
            290                 295                 300

Tyr Thr Lys Ser Ser Asn Thr Thr Ile Pro Trp Ser Pro Pro Thr Ser
            305                 310                 315

Met Ser Ile Thr Ser Ser Ser Cys Thr Arg Ser Ser Asp Trp Thr Thr
            320                 325                 330

Pro Lys Pro Pro Pro Ser Thr Ser Thr Thr Ile Gln Thr Thr Gln Thr
335                 340                 345                 350

Pro Asp Thr Ile Thr Lys Ser Asn Thr Pro Thr Thr Lys Thr Thr
                355                 360                 365
```

```
Thr Lys Ile Ser Ile Ser Ile Ser Thr Pro Trp Asn Thr Thr Cys Thr
            370                 375                 380

Ser Ser Thr Asn Ser Thr Thr Ser Thr Pro Gln Thr Thr His Thr Ala
        385                 390                 395

Thr Glu Pro Pro Thr Ser Ser Ile Ile Ala Ile Ser Ser Ser Ser Asn
400                 405                 410

Pro
415

<210> SEQ ID NO 23
<211> LENGTH: 1179
<212> TYPE: DNA
<213> ORGANISM: Botryosphaeria rhodina
<220> FEATURE:
<221> NAME/KEY: CDS
<222> LOCATION: (1)..(1179)
<220> FEATURE:
<221> NAME/KEY: sig_peptide
<222> LOCATION: (1)..(48)
<220> FEATURE:
<221> NAME/KEY: mat_peptide
<222> LOCATION: (49)..(1179)

<400> SEQUENCE: 23 atg ctt aag cac atc acc ctt gcg gca ttg gcc tcg atg gcc ttt gcc      48
Met Leu Lys His Ile Thr Leu Ala Ala Leu Ala Ser Met Ala Phe Ala
 -15                 -10                  -5                  -1 cag aca caa gac ctc aat gcc aca ctc agc ggc att ccc gag ctg tcc      96
Gln Thr Gln Asp Leu Asn Ala Thr Leu Ser Gly Ile Pro Glu Leu Ser
 1                    5                  10                  15 aat cta acg tca tac tac atc tcg ctc cct gac tcc ctg agc gcg ttg     144
Asn Leu Thr Ser Tyr Tyr Ile Ser Leu Pro Asp Ser Leu Ser Ala Leu
                 20                  25                  30 tcg gct gcc agg aac atc acc atc ctg gcg cct agt aac aat gcc ttc     192
Ser Ala Ala Arg Asn Ile Thr Ile Leu Ala Pro Ser Asn Asn Ala Phe
             35                  40                  45 gag cag ctg ttg agc agc ccc ctc ggc gcg gcg ctg acc aac gac ccg     240
Glu Gln Leu Leu Ser Ser Pro Leu Gly Ala Ala Leu Thr Asn Asp Pro
         50                  55                  60 gat ctc gtc caa gcc atg ctt acc tac cac gtg ctc aac ggc agc tac     288
Asp Leu Val Gln Ala Met Leu Thr Tyr His Val Leu Asn Gly Ser Tyr
65                  70                  75                  80 agc tcg agc cag atc act gag gac agt caa ttc atc ccc act ctc ctg     336
Ser Ser Ser Gln Ile Thr Glu Asp Ser Gln Phe Ile Pro Thr Leu Leu
                 85                  90                  95 acc gac cct agg tat acc aat gtt acc ggc ggt cag cgg gtt gag gtg     384
Thr Asp Pro Arg Tyr Thr Asn Val Thr Gly Gly Gln Arg Val Glu Val
                100                 105                 110 gag aaa gag gat ggt aac gac gtc ttt tac tcg ggg ctg cgg cag aat     432
Glu Lys Glu Asp Gly Asn Asp Val Phe Tyr Ser Gly Leu Arg Gln Asn
            115                 120                 125 ctg act ttg gga cga agt gac atc aac ttc acc ggc ggt tac atc cac     480
Leu Thr Leu Gly Arg Ser Asp Ile Asn Phe Thr Gly Gly Tyr Ile His
        130                 135                 140 atc att gac acc gtc ctc acg ctg cca cca aac gtc agc tcg acg gcc     528
Ile Ile Asp Thr Val Leu Thr Leu Pro Pro Asn Val Ser Ser Thr Ala
145                 150                 155                 160 gtg gcc acg aac ctg acg gcg ctc gtc ggg gcg ctg acc aac gcc agc     576
Val Ala Thr Asn Leu Thr Ala Leu Val Gly Ala Leu Thr Asn Ala Ser
                165                 170                 175 ctg gtc ggg gcg gtc gac acg acg ccg gac gtg acc atc ttc gcg ccg     624
Leu Val Gly Ala Val Asp Thr Thr Pro Asp Val Thr Ile Phe Ala Pro
                180                 185                 190
```

```
gcc aac gac gca ttc gct gcc atc ggc tca gtg ctc gac ggc acg tca    672
Ala Asn Asp Ala Phe Ala Ala Ile Gly Ser Val Leu Asp Gly Thr Ser
        195                 200                 205 tcg gac gac ctg tcg aac ctg ctc agc tac cac gtc gtc aac ggc acc    720
Ser Asp Asp Leu Ser Asn Leu Leu Ser Tyr His Val Val Asn Gly Thr
    210                 215                 220 gtc gcg tac tcg tcg gac ctc cag ggc aac cag acg gtc acg gcg ctc    768
Val Ala Tyr Ser Ser Asp Leu Gln Gly Asn Gln Thr Val Thr Ala Leu
225                 230                 235                 240 aac ggc ggc gac ctg acg atc cgc gtg ctg gac gac ggc gac gtc ttc    816
Asn Gly Gly Asp Leu Thr Ile Arg Val Leu Asp Asp Gly Asp Val Phe
                245                 250                 255 gtc aac ggc gcg cgc gtg atc att ccg gac atc ctg gtg gcg aac ggt    864
Val Asn Gly Ala Arg Val Ile Ile Pro Asp Ile Leu Val Ala Asn Gly
        260                 265                 270 gtg gtg cat gtc atc gac aac gtc ctc aac ccc tcc aat tcc acg tcc    912
Val Val His Val Ile Asp Asn Val Leu Asn Pro Ser Asn Ser Thr Ser
    275                 280                 285 ggc ccc agc gac gag aac gac gac agc gga gac gtc cag tac acc ggc    960
Gly Pro Ser Asp Glu Asn Asp Asp Ser Gly Asp Val Gln Tyr Thr Gly
290                 295                 300 gcc acg tcc gcg acc aac gtg ccc ttc act tcc ggc gtg gcc acg gca   1008
Ala Thr Ser Ala Thr Asn Val Pro Phe Thr Ser Gly Val Ala Thr Ala
305                 310                 315                 320 acg gcg acc gtc ggc gtc acc ggc acc ggc ggt ggt ggt gcg acg       1056
Thr Ala Thr Val Gly Val Thr Gly Thr Gly Gly Gly Gly Ala Thr
                325                 330                 335 ggc acg gcg acg ggc act ggt ggt gcc gcg agc gcg agc gcc tcg ggt   1104
Gly Thr Ala Thr Gly Thr Gly Gly Ala Ala Ser Ala Ser Ala Ser Gly
        340                 345                 350 gct gcc gct ggt gtt ggg ctg agt ggt ggg ttg atg ggt gtg gcc ctc   1152
Ala Ala Ala Gly Val Gly Leu Ser Gly Gly Leu Met Gly Val Ala Leu
    355                 360                 365 gcg ttg ggt gca gtc ctg tcg ccg ttg                               1179
Ala Leu Gly Ala Val Leu Ser Pro Leu
370                 375

<210> SEQ ID NO 24
<211> LENGTH: 393
<212> TYPE: PRT
<213> ORGANISM: Botryosphaeria rhodina

<400> SEQUENCE: 24

Met Leu Lys His Ile Thr Leu Ala Ala Leu Ala Ser Met Ala Phe Ala
        -15                 -10                 -5              -1

Gln Thr Gln Asp Leu Asn Ala Thr Leu Ser Gly Ile Pro Glu Leu Ser
1               5                   10                  15

Asn Leu Thr Ser Tyr Tyr Ile Ser Leu Pro Asp Ser Leu Ser Ala Leu
            20                  25                  30

Ser Ala Ala Arg Asn Ile Thr Ile Leu Ala Pro Ser Asn Asn Ala Phe
        35                  40                  45

Glu Gln Leu Leu Ser Ser Pro Leu Gly Ala Ala Leu Thr Asn Asp Pro
    50                  55                  60

Asp Leu Val Gln Ala Met Leu Thr Tyr His Val Leu Asn Gly Ser Tyr
65                  70                  75                  80

Ser Ser Ser Gln Ile Thr Glu Asp Ser Gln Phe Ile Pro Thr Leu Leu
                85                  90                  95

Thr Asp Pro Arg Tyr Thr Asn Val Thr Gly Gly Gln Arg Val Glu Val
            100                 105                 110
```

```
Glu Lys Glu Asp Gly Asn Asp Val Phe Tyr Ser Gly Leu Arg Gln Asn
        115                 120                 125

Leu Thr Leu Gly Arg Ser Asp Ile Asn Phe Thr Gly Tyr Ile His
        130                 135                 140

Ile Ile Asp Thr Val Leu Thr Leu Pro Pro Asn Val Ser Ser Thr Ala
145                 150                 155                 160

Val Ala Thr Asn Leu Thr Ala Leu Val Gly Ala Leu Thr Asn Ala Ser
                165                 170                 175

Leu Val Gly Ala Val Asp Thr Thr Pro Asp Val Thr Ile Phe Ala Pro
            180                 185                 190

Ala Asn Asp Ala Phe Ala Ala Ile Gly Ser Val Leu Asp Gly Thr Ser
        195                 200                 205

Ser Asp Asp Leu Ser Asn Leu Leu Ser Tyr His Val Val Asn Gly Thr
        210                 215                 220

Val Ala Tyr Ser Ser Asp Leu Gln Gly Asn Gln Thr Val Thr Ala Leu
225                 230                 235                 240

Asn Gly Gly Asp Leu Thr Ile Arg Val Leu Asp Asp Gly Asp Val Phe
                245                 250                 255

Val Asn Gly Ala Arg Val Ile Ile Pro Asp Ile Leu Val Ala Asn Gly
            260                 265                 270

Val Val His Val Ile Asp Asn Val Leu Asn Pro Ser Asn Ser Thr Ser
        275                 280                 285

Gly Pro Ser Asp Glu Asn Asp Asp Ser Gly Asp Val Gln Tyr Thr Gly
        290                 295                 300

Ala Thr Ser Ala Thr Asn Val Pro Phe Thr Ser Gly Val Ala Thr Ala
305                 310                 315                 320

Thr Ala Thr Val Gly Val Thr Gly Thr Gly Gly Gly Gly Ala Thr
                325                 330                 335

Gly Thr Ala Thr Gly Thr Gly Gly Ala Ala Ser Ala Ser Ala Ser Gly
            340                 345                 350

Ala Ala Ala Gly Val Gly Leu Ser Gly Gly Leu Met Gly Val Ala Leu
        355                 360                 365

Ala Leu Gly Ala Val Leu Ser Pro Leu
        370                 375

<210> SEQ ID NO 25
<211> LENGTH: 846
<212> TYPE: DNA
<213> ORGANISM: Botryosphaeria rhodina
<220> FEATURE:
<221> NAME/KEY: CDS
<222> LOCATION: (1)..(846)
<220> FEATURE:
<221> NAME/KEY: sig_peptide
<222> LOCATION: (1)..(69)
<220> FEATURE:
<221> NAME/KEY: mat_peptide
<222> LOCATION: (70)..(846)

<400> SEQUENCE: 25 atg cgt ttc aca aag acc act cct ctc ctc ctt atc gcc acc acc ttt     48
Met Arg Phe Thr Lys Thr Thr Pro Leu Leu Leu Ile Ala Thr Thr Phe
        -20                 -15                 -10 tcc ctc acc tac gcc gcc gct ctc ccg cct gat gac caa cga ctc cct     96
Ser Leu Thr Tyr Ala Ala Ala Leu Pro Pro Asp Asp Gln Arg Leu Pro
            -5                  -1  1               5 cag cct gtg act gac aac aag gac gcc gcc cca ttc aac ttt aac acc    144
Gln Pro Val Thr Asp Asn Lys Asp Ala Ala Pro Phe Asn Phe Asn Thr
10                  15                  20                  25
```

```
gac ggc aac ggc aaa ttc tat tac aat ggg ggc ggc gac gac gac aat      192
Asp Gly Asn Gly Lys Phe Tyr Tyr Asn Gly Gly Gly Asp Asp Asp Asn
             30                  35                  40 gac gac gac gac gac gat gat gat gac gat gac gac cag ttc gag gcc      240
Asp Asp Asp Asp Asp Asp Asp Asp Asp Asp Asp Asp Gln Phe Glu Ala
             45                  50                  55 cca gac tgc gac gac gca gaa gat gtg ttg gag gga gag tgc ggc aat      288
Pro Asp Cys Asp Asp Ala Glu Asp Val Leu Glu Gly Glu Cys Gly Asn
         60                  65                  70 ctc ctc aac ggt gaa ggc cgt ccc gtg ctg gag ggt gac ggc agt gta      336
Leu Leu Asn Gly Glu Gly Arg Pro Val Leu Glu Gly Asp Gly Ser Val
     75                  80                  85 gcg cag aag ggg gct ccg ccc cgc aag gag cgc atc aag gtg cgc agg      384
Ala Gln Lys Gly Ala Pro Pro Arg Lys Glu Arg Ile Lys Val Arg Arg
 90                  95                 100                 105 agc ctg aag ctt cat cgt ctt cgt cgt cgc aat gcc atc aag gac gat      432
Ser Leu Lys Leu His Arg Leu Arg Arg Arg Asn Ala Ile Lys Asp Asp
                    110                 115                 120 gat cat gat cac gac gac aaa gac gac cac gac cat gac cat gat gac      480
Asp His Asp His Asp Asp Lys Asp Asp His Asp His Asp His Asp Asp
                125                 130                 135 gac acg ccg gcg gag aag gct cgc gag aag gag gaa gac cgt ctc gaa      528
Asp Thr Pro Ala Glu Lys Ala Arg Glu Lys Glu Glu Asp Arg Leu Glu
            140                 145                 150 gac ctg cgg gat gcc gag gag gag gct ttg gag aag ttg aag aag ggc      576
Asp Leu Arg Asp Ala Glu Glu Glu Ala Leu Glu Lys Leu Lys Lys Gly
        155                 160                 165 ccg aat cat cgc cgc gat gaa gac gac tcc cca gcg gag cgg gct cgt      624
Pro Asn His Arg Arg Asp Glu Asp Asp Ser Pro Ala Glu Arg Ala Arg
170                 175                 180                 185 gag aag gaa gag gac aag aag gaa gat ttg cgg gat gcg gag gag gac      672
Glu Lys Glu Glu Asp Lys Lys Glu Asp Leu Arg Asp Ala Glu Glu Asp
                    190                 195                 200 cgc ttg gag cgt gag cgc aag aag cag ggt aag ggg cat cca cac gac      720
Arg Leu Glu Arg Glu Arg Lys Lys Gln Gly Lys Gly His Pro His Asp
                205                 210                 215 gat gac gac gac gat gat gat act cct gag gag aaa gcc cgc gaa cgc      768
Asp Asp Asp Asp Asp Asp Asp Thr Pro Glu Glu Lys Ala Arg Glu Arg
            220                 225                 230 gaa gaa gat cgg ctc gag gac ctg cgt gat gcg gag gac ccg tta gtg      816
Glu Glu Asp Arg Leu Glu Asp Leu Arg Asp Ala Glu Asp Pro Leu Val
        235                 240                 245 cga atg caa agg cgg cgc caa cca tct tgc                              846
Arg Met Gln Arg Arg Arg Gln Pro Ser Cys
250                 255
```

<210> SEQ ID NO 26
<211> LENGTH: 282
<212> TYPE: PRT
<213> ORGANISM: Botryosphaeria rhodina

<400> SEQUENCE: 26

```
Met Arg Phe Thr Lys Thr Thr Pro Leu Leu Leu Ile Ala Thr Thr Phe
            -20                 -15                 -10

Ser Leu Thr Tyr Ala Ala Ala Leu Pro Pro Asp Asp Gln Arg Leu Pro
         -5         -1   1               5

Gln Pro Val Thr Asp Asn Lys Asp Ala Ala Pro Phe Asn Phe Asn Thr
 10                  15                  20                  25

Asp Gly Asn Gly Lys Phe Tyr Tyr Asn Gly Gly Gly Asp Asp Asp Asn
             30                  35                  40
```

```
Asp Asp Asp Asp Asp Asp Asp Asp Asp Asp Gln Phe Glu Ala
            45                  50                  55

Pro Asp Cys Asp Asp Ala Glu Asp Val Leu Glu Gly Glu Cys Gly Asn
        60                  65                  70

Leu Leu Asn Gly Glu Gly Arg Pro Val Leu Glu Gly Asp Gly Ser Val
    75                  80                  85

Ala Gln Lys Gly Ala Pro Pro Arg Lys Glu Arg Ile Lys Val Arg Arg
90                  95                 100                 105

Ser Leu Lys Leu His Arg Leu Arg Arg Asn Ala Ile Lys Asp Asp
                110                 115                 120

Asp His Asp His Asp Asp Lys Asp Asp His Asp His Asp His Asp Asp
                125                 130                 135

Asp Thr Pro Ala Glu Lys Ala Arg Glu Lys Glu Glu Asp Arg Leu Glu
                140                 145                 150

Asp Leu Arg Asp Ala Glu Glu Ala Leu Glu Lys Leu Lys Lys Gly
                155                 160                 165

Pro Asn His Arg Arg Asp Glu Asp Asp Ser Pro Ala Glu Arg Ala Arg
170                 175                 180                 185

Glu Lys Glu Glu Asp Lys Lys Glu Asp Leu Arg Asp Ala Glu Glu Asp
                190                 195                 200

Arg Leu Glu Arg Glu Arg Lys Lys Gln Gly Lys Gly His Pro His Asp
                205                 210                 215

Asp Asp Asp Asp Asp Asp Thr Pro Glu Glu Lys Ala Arg Glu Arg
                220                 225                 230

Glu Glu Asp Arg Leu Glu Asp Leu Arg Asp Ala Glu Asp Pro Leu Val
    235                 240                 245

Arg Met Gln Arg Arg Arg Gln Pro Ser Cys
250                 255

<210> SEQ ID NO 27
<211> LENGTH: 801
<212> TYPE: DNA
<213> ORGANISM: Botryosphaeria rhodina
<220> FEATURE:
<221> NAME/KEY: CDS
<222> LOCATION: (1)..(801)
<220> FEATURE:
<221> NAME/KEY: sig_peptide
<222> LOCATION: (1)..(57)
<220> FEATURE:
<221> NAME/KEY: misc_feature
<222> LOCATION: (1)..(801)
<223> OTHER INFORMATION: propeptide
<220> FEATURE:
<221> NAME/KEY: mat_peptide
<222> LOCATION: (58)..(801)
<220> FEATURE:
<221> NAME/KEY: misc_feature
<222> LOCATION: (729)..(798)
<223> OTHER INFORMATION: transmembrane peptide

<400> SEQUENCE: 27 atg cgc ttc ttc tcc acc atc gtc ggc gct gcc gcc ctc att tcg agc      48
Met Arg Phe Phe Ser Thr Ile Val Gly Ala Ala Ala Leu Ile Ser Ser
            -15                 -10                  -5 gtc gtt gct cag gac ctc ggc atc acc aag gct ccc tcc tct gtc cag      96
Val Val Ala Gln Asp Leu Gly Ile Thr Lys Ala Pro Ser Ser Val Gln
        -1  1               5                  10 gcc ggc caa acc tac acc att gag tac act gcg ccg gct ggc gcc gct     144
Ala Gly Gln Thr Tyr Thr Ile Glu Tyr Thr Ala Pro Ala Gly Ala Ala
    15                  20                  25
```

```
gtg tct ctc atc ctg cgc aag ggt gac ccc aac aac ctg gac act ctc        192
Val Ser Leu Ile Leu Arg Lys Gly Asp Pro Asn Asn Leu Asp Thr Leu
 30              35                  40                  45 act acc ctg acc tcc aat gcc gaa ggc ggt tct tac gag tgg act gtg        240
Thr Thr Leu Thr Ser Asn Ala Glu Gly Gly Ser Tyr Glu Trp Thr Val
                 50                  55                  60 gcc agc agc cta gag agc gac gac gac tac gcc atc gag att aag cag        288
Ala Ser Ser Leu Glu Ser Asp Asp Asp Tyr Ala Ile Glu Ile Lys Gln
             65                  70                  75 ggc gac gac aac aac tac ttc ggc ccc ttc agc ctc acc ggt ggt tcc        336
Gly Asp Asp Asn Asn Tyr Phe Gly Pro Phe Ser Leu Thr Gly Gly Ser
         80                  85                  90 gcc tcg gcc tct tcg gca tct tcc agc tcc tct gct tct gct tct gcc        384
Ala Ser Ala Ser Ser Ala Ser Ser Ser Ser Ser Ala Ser Ala Ser Ala
     95                 100                 105 tct tct tcg gcc tct gcc tct gcc tct gcg tcc gcg tct gct tcg gcc        432
Ser Ser Ser Ala Ser Ala Ser Ala Ser Ala Ser Ala Ser Ala Ser Ala
110                 115                 120                 125 tct gcc tcg gct tct ggc tcc gcc agc tcg acc gag agc tcc acc atc        480
Ser Ala Ser Ala Ser Gly Ser Ala Ser Ser Thr Glu Ser Ser Thr Ile
                130                 135                 140 act gcc agc gcc tcg ctc tcc tcg gct gcc tcc tcg ctg tcc tcg ctg        528
Thr Ala Ser Ala Ser Leu Ser Ser Ala Ala Ser Ser Leu Ser Ser Leu
            145                 150                 155 atc tcg gcc gcc aac tcg acc ctg gcc tcc atc acc agc tcg aac gcg        576
Ile Ser Ala Ala Asn Ser Thr Leu Ala Ser Ile Thr Ser Ser Asn Ala
        160                 165                 170 act gcc acc agc agc aag ccg tcc aac ggc act atc agc agc acc ctg        624
Thr Ala Thr Ser Ser Lys Pro Ser Asn Gly Thr Ile Ser Ser Thr Leu
    175                 180                 185 cac agc tcg act gcc acc tcc acc tcg tcg tcg tct gag ggc tcg            672
His Ser Ser Thr Ala Thr Ser Thr Ser Ser Ser Ser Glu Gly Ser
190                 195                 200                 205 agc tcc tcc ggc gcg tcc gag act gcc agc tcg act ggc ggc gcc cct        720
Ser Ser Ser Gly Ala Ser Glu Thr Ala Ser Ser Thr Gly Gly Ala Pro
                210                 215                 220 acc tcc ggt gcc gcc atg ccc agc atg gtc agc ccc atc gcg ctc gtc        768
Thr Ser Gly Ala Ala Met Pro Ser Met Val Ser Pro Ile Ala Leu Val
            225                 230                 235 ctc ggc gcc gtt gct gcc atg atc ttc ctc aac                            801
Leu Gly Ala Val Ala Ala Met Ile Phe Leu Asn
                240                 245
```

<210> SEQ ID NO 28
<211> LENGTH: 267
<212> TYPE: PRT
<213> ORGANISM: Botryosphaeria rhodina

<400> SEQUENCE: 28

```
Met Arg Phe Phe Ser Thr Ile Val Gly Ala Ala Ala Leu Ile Ser Ser
                -15                 -10                  -5

Val Val Ala Gln Asp Leu Gly Ile Thr Lys Ala Pro Ser Ser Val Gln
         -1   1              5                  10

Ala Gly Gln Thr Tyr Thr Ile Glu T

-continued

```
                         65                  70                  75
Gly Asp Asp Asn Asn Tyr Phe Gly Pro Phe Ser Leu Thr Gly Gly Ser
                 80                  85                  90

Ala Ser Ala Ser Ser Ala Ser Ser Ser Ser Ala Ser Ala Ser Ala
         95                 100                 105

Ser Ser Ser Ala Ser Ala Ser Ala Ser Ala Ser Ala Ser Ala
110                 115                 120                 125

Ser Ala Ser Ala Ser Gly Ser Ala Ser Ser Thr Glu Ser Thr Ile
                130                 135                 140

Thr Ala Ser Ala Ser Leu Ser Ser Ala Ala Ser Ser Leu Ser Ser Leu
                145                 150                 155

Ile Ser Ala Ala Asn Ser Thr Leu Ala Ser Ile Thr Ser Ser Asn Ala
                160                 165                 170

Thr Ala Thr Ser Ser Lys Pro Ser Asn Gly Thr Ile Ser Ser Thr Leu
                175                 180                 185

His Ser Ser Thr Ala Thr Ser Thr Ser Ser Ser Ser Glu Gly Ser
190                 195                 200                 205

Ser Ser Ser Gly Ala Ser Glu Thr Ala Ser Ser Thr Gly Gly Ala Pro
                210                 215                 220

Thr Ser Gly Ala Ala Met Pro Ser Met Val Ser Pro Ile Ala Leu Val
                225                 230                 235

Leu Gly Ala Val Ala Ala Met Ile Phe Leu Asn
                240                 245

<210> SEQ ID NO 29
<211> LENGTH: 1065
<212> TYPE: DNA
<213> ORGANISM: Botryosphaeria rhodina
<220> FEATURE:
<221> NAME/KEY: misc_feature
<222> LOCATION: (1)..(1065)
<223> OTHER INFORMATION: cDNA
<220> FEATURE:
<221> NAME/KEY: CDS
<222> LOCATION: (109)..(603)
<220> FEATURE:
<221> NAME/KEY: transit_peptide
<222> LOCATION: (109)..(156)
<220> FEATURE:
<221> NAME/KEY: misc_feature
<222> LOCATION: (109)..(603)
<223> OTHER INFORMATION: propeptide
<220> FEATURE:
<221> NAME/KEY: mat_peptide
<222> LOCATION: (157)..(603)

<400> SEQUENCE: 29
ggcacgaggc accataatca ctatcagaac ccaaaccagt cgtttctgat atcaaaccct      60
catctaaacc tcatctcaaa ccaaccgaaa aggaccaata aaaccaac atg atg caa     117
                                                    Met Met Gln
                                                        -15 ttc ctc act gtc gcc gcc ctc ttc acc acc gcc gcc ttc gcc tct ccc     165
Phe Leu Thr Val Ala Ala Leu Phe Thr Thr Ala Ala Phe Ala Ser Pro
            -10                 -5                  -1  1 atc gca cag gct ccc aac acc cca cct gcc ggc act ccc gtc tac act     213
Ile Ala Gln Ala Pro Asn Thr Pro Pro Ala Gly Thr Pro Val Tyr Thr
        5                  10                  15 ccg gcc agc acc ccg atc tac tac ccc ctc aac act ccg gtc aac acg     261
Pro Ala Ser Thr Pro Ile Tyr Tyr Pro Leu Asn Thr Pro Val Asn Thr
 20                  25                  30                  35 cca gtc gcc act ccc ggc agc ggc agc ggc ccc ggc ttc atc ggc ggc     309
Pro Val Ala Thr Pro Gly Ser Gly Ser Gly Pro Gly Phe Ile Gly Gly
```

```
                    40              45              50
ggc tac aac agc ctc ccc gtc tgc ggc ccg cac gcc tac gac ccg cgc      357
Gly Tyr Asn Ser Leu Pro Val Cys Gly Pro His Ala Tyr Asp Pro Arg
             55              60              65 gcc ttc cac tgc tac gac agc agc gtc ggc tac ggc ggc cag acg tac      405
Ala Phe His Cys Tyr Asp Ser Ser Val Gly Tyr Gly Gly Gln Thr Tyr
         70              75              80 acc aac atc ctg tgc ccg ctg cag aac ggc gag ccg ctg gcc gcc tgc      453
Thr Asn Ile Leu Cys Pro Leu Gln Asn Gly Glu Pro Leu Ala Ala Cys
     85              90              95 ggc ccg agc tgc tac gac ccg gag atc ttc acc tgc ggc gcc gac ggc      501
Gly Pro Ser Cys Tyr Asp Pro Glu Ile Phe Thr Cys Gly Ala Asp Gly
100             105             110             115 atc ctg tct gtc gcc ggc cag tac gcc acc ccc gcc gcc gct acc ccg      549
Ile Leu Ser Val Ala Gly Gln Tyr Ala Thr Pro Ala Ala Ala Thr Pro
                120             125             130 atg act ccg gcc ggc gtc ttc cct ccg gcc ggc gcg acg ccg acg ggg      597
Met Thr Pro Ala Gly Val Phe Pro Pro Ala Gly Ala Thr Pro Thr Gly
            135             140             145 ggc ctc taagcgggat cgtccggaat gacgatcagc tcaagcatgt gtgagcgaga       653
Gly Leu gagacagagc atagctactg cgtattaaaa gctgtgaaga ggtgacacgg caatgcacgt    713
tcgtcttggg catttctttt ggggtttcat ggcgtaggat gctgggcgct tcttgggtgg    773
tcttatgagc atttaacgtt ccttctacgc ttagagtggc tgcaacgttg atgaatgagg    833
ggggtgatgg tcgatcagtt gaccgttccg tgtgaaccgt gtcaaacacg tcacacgtcg    893
ccatgagtcg accacgtcgt tgatgtgcaa agaacatcg aggatgcaac aaggaaatga     953
ttaatggaca tcatgtttta agtacataaa gggagatcat gggtagacta aacgaaaagc   1013
cccctctaat gttaatattt ctcatcttaa aaaaaaaga ttcatttgtc tc            1065

<210> SEQ ID NO 30
<211> LENGTH: 165
<212> TYPE: PRT
<213> ORGANISM: Botryosphaeria rhodina

<400> SEQUENCE: 30

Met Met Gln Phe Leu Thr Val Ala Ala Leu Phe Thr Thr Ala Ala Phe
    -15             -10              -5              -1

Ala Ser Pro Ile Ala Gln Ala Pro Asn Thr Pro Pro Ala Gly Thr Pro
1               5               10              15

Val Tyr Thr Pro Ala Ser Thr Pro Ile Tyr Tyr Pro Leu Asn Thr Pro
            20              25              30

Val Asn Thr Pro Val Ala Thr Pro Gly Ser Gly Ser Gly Pro Gly Phe
        35              40              45

Ile Gly Gly Gly Tyr Asn Ser Leu Pro Val Cys Gly Pro His Ala Tyr
    50              55              60

Asp Pro Arg Ala Phe His Cys Tyr Asp Ser Ser Val Gly Tyr Gly Gly
65              70              75              80

Gln Thr Tyr Thr Asn Ile Leu Cys Pro Leu Gln Asn Gly Glu Pro Leu
                85              90              95

Ala Ala Cys Gly Pro Ser Cys Tyr Asp Pro Glu Ile Phe Thr Cys Gly
            100             105             110

Ala Asp Gly Ile Leu Ser Val Ala Gly Gln Tyr Ala Thr Pro Ala Ala
        115             120             125

Ala Thr Pro Met Thr Pro Ala Gly Val Phe Pro Pro Ala Gly Ala Thr
    130             135             140
```

Pro Thr Gly Gly Leu
145

```
<210> SEQ ID NO 31
<211> LENGTH: 660
<212> TYPE: DNA
<213> ORGANISM: Botryosphaeria rhodina
<220> FEATURE:
<221> NAME/KEY: CDS
<222> LOCATION: (1)..(660)
<220> FEATURE:
<221> NAME/KEY: transit_peptide
<222> LOCATION: (1)..(54)
<220> FEATURE:
<221> NAME/KEY: misc_feature
<222> LOCATION: (1)..(660)
<223> OTHER INFORMATION: propeptide
<220> FEATURE:
<221> NAME/KEY: mat_peptide
<222> LOCATION: (55)..(660)
```

<400> SEQUENCE: 31

| | | | | | | | | | | | | | | | | |
|---|---|---|---|---|---|---|---|---|---|---|---|---|---|---|---|---|
| atg | aag | act | ttc | gca | ttc | gcc | acc | gtg | gct | gcg | ctc | agc | gct | gtt | gct | 48 |
| Met | Lys | Thr | Phe | Ala | Phe | Ala | Thr | Val | Ala | Ala | Leu | Ser | Ala | Val | Ala | |
| | | -15 | | | | | -10 | | | | | -5 | | | | |

| | | | | | | | | | | | | | | | | |
|---|---|---|---|---|---|---|---|---|---|---|---|---|---|---|---|---|
| acc | gcc | caa | gac | ttg | ggg | ctg | ttg | ctc | tca | tcc | tgc | gcc | tcc | gat | caa | 96 |
| Thr | Ala | Gln | Asp | Leu | Gly | Leu | Leu | Leu | Ser | Ser | Cys | Ala | Ser | Asp | Gln | |
| | -1 | 1 | | | 5 | | | | | 10 | | | | | | |

| | | | | | | | | | | | | | | | | |
|---|---|---|---|---|---|---|---|---|---|---|---|---|---|---|---|---|
| ttt | cag | gaa | ctt | gga | ttg | acc | gga | gtc | gac | ggt | gat | ccg | tgc | aag | agc | 144 |
| Phe | Gln | Glu | Leu | Gly | Leu | Thr | Gly | Val | Asp | Gly | Asp | Pro | Cys | Lys | Ser | |
| 15 | | | | | 20 | | | | | 25 | | | | | 30 | |

| | | | | | | | | | | | | | | | | |
|---|---|---|---|---|---|---|---|---|---|---|---|---|---|---|---|---|
| gat | gcg | ggc | aaa | tct | tcg | tac | tat | gag | tgc | tcc | tgc | acc | aag | ggt | cag | 192 |
| Asp | Ala | Gly | Lys | Ser | Ser | Tyr | Tyr | Glu | Cys | Ser | Cys | Thr | Lys | Gly | Gln | |
| | | | | 35 | | | | | 40 | | | | | 45 | | |

| | | | | | | | | | | | | | | | | |
|---|---|---|---|---|---|---|---|---|---|---|---|---|---|---|---|---|
| gag | ttt | gtc | gtc | gat | tac | ctc | tgc | aaa | aac | cct | gga | tcc | tgc | agc | ccc | 240 |
| Glu | Phe | Val | Val | Asp | Tyr | Leu | Cys | Lys | Asn | Pro | Gly | Ser | Cys | Ser | Pro | |
| | | | 50 | | | | | 55 | | | | | 60 | | | |

| | | | | | | | | | | | | | | | | |
|---|---|---|---|---|---|---|---|---|---|---|---|---|---|---|---|---|
| agc | gac | atc | cct | ggc | ttg | acg | gat | act | ctc | gtc | agc | ttc | tgc | aaa | tcg | 288 |
| Ser | Asp | Ile | Pro | Gly | Leu | Thr | Asp | Thr | Leu | Val | Ser | Phe | Cys | Lys | Ser | |
| | | 65 | | | | | 70 | | | | | 75 | | | | |

| | | | | | | | | | | | | | | | | |
|---|---|---|---|---|---|---|---|---|---|---|---|---|---|---|---|---|
| gtc | ggt | gtc | acc | gtc | aca | gct | ccc | tcg | aac | ccg | tgc | ggt | ctc | tcc | ggc | 336 |
| Val | Gly | Val | Thr | Val | Thr | Ala | Pro | Ser | Asn | Pro | Cys | Gly | Leu | Ser | Gly | |
| | 80 | | | | | 85 | | | | | 90 | | | | | |

| | | | | | | | | | | | | | | | | |
|---|---|---|---|---|---|---|---|---|---|---|---|---|---|---|---|---|
| ggt | agt | agc | tct | tct | gct | cct | gcg | tcc | tct | gcc | aca | tcc | gct | ccc | gcc | 384 |
| Gly | Ser | Ser | Ser | Ser | Ala | Pro | Ala | Ser | Ser | Ala | Thr | Ser | Ala | Pro | Ala | |
| 95 | | | | | 100 | | | | | 105 | | | | | 110 | |

| | | | | | | | | | | | | | | | | |
|---|---|---|---|---|---|---|---|---|---|---|---|---|---|---|---|---|
| acg | tcc | gcc | cct | agt | tct | tca | cct | gca | tcg | tcg | cca | gcc | tcc | tcg | gcg | 432 |
| Thr | Ser | Ala | Pro | Ser | Ser | Ser | Pro | Ala | Ser | Ser | Pro | Ala | Ser | Ser | Ala | |
| | | | | 115 | | | | | 120 | | | | | 125 | | |

| | | | | | | | | | | | | | | | | |
|---|---|---|---|---|---|---|---|---|---|---|---|---|---|---|---|---|
| gct | tcc | tcc | gca | gcg | agc | tct | gcc | ccg | agc | tat | gcc | ccc | agc | tcc | gct | 480 |
| Ala | Ser | Ser | Ala | Ala | Ser | Ser | Ala | Pro | Ser | Tyr | Ala | Pro | Ser | Ser | Ala | |
| | | 130 | | | | | 135 | | | | | 140 | | | | |

| | | | | | | | | | | | | | | | | |
|---|---|---|---|---|---|---|---|---|---|---|---|---|---|---|---|---|
| gca | tca | tct | cct | ccg | gcc | aca | act | ccc | gcc | ggt | aca | ccc | act | acc | ccg | 528 |
| Ala | Ser | Ser | Pro | Pro | Ala | Thr | Thr | Pro | Ala | Gly | Thr | Pro | Thr | Thr | Pro | |
| | | 145 | | | | | 150 | | | | | 155 | | | | |

| | | | | | | | | | | | | | | | | |
|---|---|---|---|---|---|---|---|---|---|---|---|---|---|---|---|---|
| gct | gga | acc | cct | tat | ggt | act | cca | gtc | ggc | acc | ccg | gcc | agc | act | ccg | 576 |
| Ala | Gly | Thr | Pro | Tyr | Gly | Thr | Pro | Val | Gly | Thr | Pro | Ala | Ser | Thr | Pro | |
| | 160 | | | | | 165 | | | | | 170 | | | | | |

| | | | | | | | | | | | | | | | | |
|---|---|---|---|---|---|---|---|---|---|---|---|---|---|---|---|---|
| gct | gcc | tac | act | ggt | gca | gct | gca | gtt | aaa | aac | gtg | gct | ggt | ggt | ctc | 624 |
| Ala | Ala | Tyr | Thr | Gly | Ala | Ala | Ala | Val | Lys | Asn | Val | Ala | Gly | Gly | Leu | |
| 175 | | | | | 180 | | | | | 185 | | | | | 190 | |

| | | | | | | | | | | |
|---|---|---|---|---|---|---|---|---|---|---|
| gtc | ggt | gtg | gct | ggt | ttt | gct | ggc | ctc | ttc | ttc ctc | 660 |
| Val | Gly | Val | Ala | Gly | Phe | Ala | Gly | Leu | Phe | Phe Leu | |
| | | | | 195 | | | | | 200 | | |

<210> SEQ ID NO 32
<211> LENGTH: 220
<212> TYPE: PRT
<213> ORGANISM: Botryosphaeria rhodina

<400> SEQUENCE: 32

```
Met Lys Thr Phe Ala Phe Ala Thr Val Ala Ala Leu Ser Ala Val Ala
            -15                 -10                  -5

Thr Ala Gln Asp Leu Gly Leu Leu Ser Ser Cys Ala Ser Asp Gln
 -1   1               5                  10

Phe Gln Glu Leu Gly Leu Thr Gly Val Asp Gly Asp Pro Cys Lys Ser
 15                  20                  25                  30

Asp Ala Gly Lys Ser Ser Tyr Tyr Glu Cys Ser Cys Thr Lys Gly Gln
                 35                  40                  45

Glu Phe Val Val Asp Tyr Leu Cys Lys Asn Pro Gly Ser Cys Ser Pro
                 50                  55                  60

Ser Asp Ile Pro Gly Leu Thr Asp Thr Leu Val Ser Phe Cys Lys Ser
                 65                  70                  75

Val Gly Val Thr Val Thr Ala Pro Ser Asn Pro Cys Gly Leu Ser Gly
 80                  85                  90

Gly Ser Ser Ser Ala Pro Ala Ser Ser Ala Thr Ser Ala Pro Ala
 95                  100                 105                 110

Thr Ser Ala Pro Ser Ser Ser Pro Ala Ser Ser Pro Ala Ser Ser Ala
                 115                 120                 125

Ala Ser Ser Ala Ala Ser Ser Ala Pro Ser Tyr Ala Pro Ser Ser Ala
                 130                 135                 140

Ala Ser Ser Pro Pro Ala Thr Thr Pro Ala Gly Thr Pro Thr Thr Pro
                 145                 150                 155

Ala Gly Thr Pro Tyr Gly Thr Pro Val Gly Thr Pro Ala Ser Thr Pro
                 160                 165                 170

Ala Ala Tyr Thr Gly Ala Ala Ala Val Lys Asn Val Ala Gly Gly Leu
175                 180                 185                 190

Val Gly Val Ala Gly Phe Ala Gly Leu Phe Phe Leu
                 195                 200
```

<210> SEQ ID NO 33
<211> LENGTH: 1854
<212> TYPE: DNA
<213> ORGANISM: Botryosphaeria rhodina
<220> FEATURE:
<221> NAME/KEY: CDS
<222> LOCATION: (1)..(1854)
<220> FEATURE:
<221> NAME/KEY: sig_peptide
<222> LOCATION: (1)..(45)
<220> FEATURE:
<221> NAME/KEY: mat_peptide
<222> LOCATION: (46)..(1854)

<400> SEQUENCE: 33

```
atg tct ttg ctt ttg ctg ctc agc agc ggc gct att gcg ctc gca caa    48
Met Ser Leu Leu Leu Leu Leu Ser Ser Gly Ala Ile Ala Leu Ala Gln
-15                 -10                  -5                  -1  1 cag gtc tat gtg tct gct gat gga cct gct caa tgc acc gca agc cag    96
Gln Val Tyr Val Ser Ala Asp Gly Pro Ala Gln Cys Thr Ala Ser Gln
                 5                   10                  15 act tat tct gcg act tac gct tct ccg acc tat gcc ttc agc aac ttt   144
Thr Tyr Ser Ala Thr Tyr Ala Ser Pro Thr Tyr Ala Phe Ser Asn Phe
            20                  25                  30
```

| | | |
|---|---|---|
| tcg ttc acg caa acg gag acg gtc cgg act gct acc tca gtc aag tct<br>Ser Phe Thr Gln Thr Glu Thr Val Arg Thr Ala Thr Ser Val Lys Ser<br>35　　　　　　　　40　　　　　　　　　　45 | | 192 |
| gcg cca gtc aca act tac gcc ccg cca tac gca tcc ctc agc cac ctg<br>Ala Pro Val Thr Thr Tyr Ala Pro Pro Tyr Ala Ser Leu Ser His Leu<br>50　　　　　　　　　　55　　　　　　　　　　60　　　　　　　　65 | | 240 |
| gtt cca gat ctg agc aca acg tgg gga aac tgg gat ccc aat gcc<br>Val Pro Asp Leu Ser Thr Thr Trp Gly Asn Trp Asp Pro Asn Ala<br>　　　　　　　　70　　　　　　　　　75　　　　　　　　　　80 | | 288 |
| acg gca act gcc acc gat acc gcc gac ccc tac gga cag gct gcg tgg<br>Thr Ala Thr Ala Thr Asp Thr Ala Asp Pro Tyr Gly Gln Ala Ala Trp<br>　　　　　　　85　　　　　　　　　　90　　　　　　　　　　95 | | 336 |
| tct gct ttg tgg gaa cat gcc agt ctc gcc aac ttt acc ttc agg ggt<br>Ser Ala Leu Trp Glu His Ala Ser Leu Ala Asn Phe Thr Phe Arg Gly<br>100　　　　　　　　　105　　　　　　　　　110 | | 384 |
| ctt tac tca aca acc gtc tcc cca act ccg gtg cct act agt gaa ctt<br>Leu Tyr Ser Thr Thr Val Ser Pro Thr Pro Val Pro Thr Ser Glu Leu<br>115　　　　　　　　　120　　　　　　　　　125 | | 432 |
| gtt ctg ccg cct cca gaa tat ttc act ccc cag gac tgc tct tac ttc<br>Val Leu Pro Pro Pro Glu Tyr Phe Thr Pro Gln Asp Cys Ser Tyr Phe<br>130　　　　　　　　　135　　　　　　　　　140　　　　　　　　145 | | 480 |
| cca gac gac ttc atg ttc gga gtt gca ggc tct gct tcc cag atc gaa<br>Pro Asp Asp Phe Met Phe Gly Val Ala Gly Ser Ala Ser Gln Ile Glu<br>　　　　　　　　　150　　　　　　　　　155　　　　　　　　　160 | | 528 |
| ggg gcc atc gca gac gaa ggg aga aca ccc tct ctc atg gaa att ttg<br>Gly Ala Ile Ala Asp Glu Gly Arg Thr Pro Ser Leu Met Glu Ile Leu<br>　　　　　　　165　　　　　　　　　170　　　　　　　　　175 | | 576 |
| atc tct cct tcg acc gga aaa ccc acc aac tac gtc aca aac gag aac<br>Ile Ser Pro Ser Thr Gly Lys Pro Thr Asn Tyr Val Thr Asn Glu Asn<br>180　　　　　　　　　185　　　　　　　　　190 | | 624 |
| tac tac ctg tac aag cag gat atc gag cgt ctg gct gct atg gga gtc<br>Tyr Tyr Leu Tyr Lys Gln Asp Ile Glu Arg Leu Ala Ala Met Gly Val<br>195　　　　　　　　　200　　　　　　　　　205 | | 672 |
| aag tac tat tct ttt act att ccg tgg tct cga atc ttg cca ttc gtg<br>Lys Tyr Tyr Ser Phe Thr Ile Pro Trp Ser Arg Ile Leu Pro Phe Val<br>210　　　　　　　　　215　　　　　　　　　220　　　　　　　　225 | | 720 |
| ctt gaa ggc acc ccc ctc aac cag caa ggc ctc gac cac tac gac gat<br>Leu Glu Gly Thr Pro Leu Asn Gln Gln Gly Leu Asp His Tyr Asp Asp<br>　　　　　　　　　230　　　　　　　　　235　　　　　　　　　240 | | 768 |
| ctc att aat ttt gtc ctt gag aag gga atg cag ccg act gtc acc ctg<br>Leu Ile Asn Phe Val Leu Glu Lys Gly Met Gln Pro Thr Val Thr Leu<br>　　　　　　　245　　　　　　　　　250　　　　　　　　　255 | | 816 |
| atc cac ttc gac acg cct ctg cag ttc tac gga aac aac tta agc act<br>Ile His Phe Asp Thr Pro Leu Gln Phe Tyr Gly Asn Asn Leu Ser Thr<br>260　　　　　　　　　265　　　　　　　　　270 | | 864 |
| gct gcg gac cct cct ctt att ggt tac acc aac gga gct tat cag aat<br>Ala Ala Asp Pro Pro Leu Ile Gly Tyr Thr Asn Gly Ala Tyr Gln Asn<br>275　　　　　　　　　280　　　　　　　　　285 | | 912 |
| gag acg ttc gag gat gct ttc gtg aac tat ggc aag atc gtc atg act<br>Glu Thr Phe Glu Asp Ala Phe Val Asn Tyr Gly Lys Ile Val Met Thr<br>290　　　　　　　　　295　　　　　　　　　300　　　　　　　　305 | | 960 |
| cac ttt gct gac cgt gtt cct gtc tgg ttc act ttc aat gaa ccc tta<br>His Phe Ala Asp Arg Val Pro Val Trp Phe Thr Phe Asn Glu Pro Leu<br>　　　　　　　　　310　　　　　　　　　315　　　　　　　　　320 | | 1008 |
| ctc tat tgt gac aat ggc aag agt gta aac acg gtt gtc aaa gcc cat<br>Leu Tyr Cys Asp Asn Gly Lys Ser Val Asn Thr Val Val Lys Ala His<br>　　　　　　　325　　　　　　　　　330　　　　　　　　　335 | | 1056 |
| gcc aga ctc tat cat ttc tat cac gag gag atc aac ggc acc ggc aag<br>Ala Arg Leu Tyr His Phe Tyr His Glu Glu Ile Asn Gly Thr Gly Lys<br>340　　　　　　　　　345　　　　　　　　　350 | | 1104 |

```
gtt gga atc aag ttc aac gac aac ttt ggt gta cca cgc gac cct cag    1152
Val Gly Ile Lys Phe Asn Asp Asn Phe Gly Val Pro Arg Asp Pro Gln
        355                 360                 365 gat tcc tcg gat gtg gac gcc gcg aac cat ttc aac gag ttt caa ctg    1200
Asp Ser Ser Asp Val Asp Ala Ala Asn His Phe Asn Glu Phe Gln Leu
370                 375                 380                 385 gca aca ttt gcc aac cct atc ttc ctc ggg aag gat tac cct gag gcc    1248
Ala Thr Phe Ala Asn Pro Ile Phe Leu Gly Lys Asp Tyr Pro Glu Ala
                390                 395                 400 ttc aag atg aca gtc ccc gat tat gtg ccg ctc tca cag gag gat ttg    1296
Phe Lys Met Thr Val Pro Asp Tyr Val Pro Leu Ser Gln Glu Asp Leu
            405                 410                 415 gaa tac atc ggt ggt aca tca gac ttc ctc ggc atc gat ccc tac act    1344
Glu Tyr Ile Gly Gly Thr Ser Asp Phe Leu Gly Ile Asp Pro Tyr Thr
        420                 425                 430 gcg aca gtc gta agc ccg ccg cct gat gga att gcg gtt tgc gca gcc    1392
Ala Thr Val Val Ser Pro Pro Pro Asp Gly Ile Ala Val Cys Ala Ala
    435                 440                 445 aac aca tcc gac ccc ctc ttc ccc tac tgc gtc gag caa tca acc ttg    1440
Asn Thr Ser Asp Pro Leu Phe Pro Tyr Cys Val Glu Gln Ser Thr Leu
450                 455                 460                 465 aca agc acc ggc tgg aac atc ggt tac cgt tcg cag acc tac gtc tac    1488
Thr Ser Thr Gly Trp Asn Ile Gly Tyr Arg Ser Gln Thr Tyr Val Tyr
                470                 475                 480 atc acg ccc aag tac ctg cgc acc tac ctg tcc tat ctg tgg aac acc    1536
Ile Thr Pro Lys Tyr Leu Arg Thr Tyr Leu Ser Tyr Leu Trp Asn Thr
            485                 490                 495 ttc cag cac cct gtc atg atc act gag ttt ggc tac cct gtg ttc ggc    1584
Phe Gln His Pro Val Met Ile Thr Glu Phe Gly Tyr Pro Val Phe Gly
        500                 505                 510 gag gcg gac aag gaa gat ctc tcg gac cag ttg tac gac ctt cct cgc    1632
Glu Ala Asp Lys Glu Asp Leu Ser Asp Gln Leu Tyr Asp Leu Pro Arg
    515                 520                 525 agc tac tac tac ctc tct ttc atg agt gag gtg ctc aag gca atc tgg    1680
Ser Tyr Tyr Tyr Leu Ser Phe Met Ser Glu Val Leu Lys Ala Ile Trp
530                 535                 540                 545 gag gac aac gtc cac gtc ctt ggg gcg ttc gcg tgg agc ttt gcc gat    1728
Glu Asp Asn Val His Val Leu Gly Ala Phe Ala Trp Ser Phe Ala Asp
                550                 555                 560 aac tgg gaa ttc ggt gac tac gcg caa caa ttt ggc att cag gtc gtc    1776
Asn Trp Glu Phe Gly Asp Tyr Ala Gln Gln Phe Gly Ile Gln Val Val
            565                 570                 575 aac cgt acg acg caa gag agg tat tat aag aag agt ttc ttc gat ctg    1824
Asn Arg Thr Thr Gln Glu Arg Tyr Tyr Lys Lys Ser Phe Phe Asp Leu
        580                 585                 590 gtg gac ttc gtg gcg gcg agg aca aag tct                            1854
Val Asp Phe Val Ala Ala Arg Thr Lys Ser
    595                 600

<210> SEQ ID NO 34
<211> LENGTH: 618
<212> TYPE: PRT
<213> ORGANISM: Botryosphaeria rhodina

<400> SEQUENCE: 34

Met Ser Leu Leu Leu Leu Leu Ser Ser Gly Ala Ile Ala

```
Ser Phe Thr Gln Thr Glu Thr Val Arg Thr Ala Thr Ser Val Lys Ser
 35                  40                  45

Ala Pro Val Thr Thr Tyr Ala Pro Pro Tyr Ala Ser Leu Ser His Leu
 50                  55                  60                  65

Val Pro Asp Leu Ser Thr Thr Thr Trp Gly Asn Trp Asp Pro Asn Ala
                 70                  75                  80

Thr Ala Thr Ala Thr Asp Thr Ala Asp Pro Tyr Gly Gln Ala Ala Trp
                 85                  90                  95

Ser Ala Leu Trp Glu His Ala Ser Leu Ala Asn Phe Thr Phe Arg Gly
                100                 105                 110

Leu Tyr Ser Thr Thr Val Ser Pro Thr Pro Val Pro Thr Ser Glu Leu
        115                 120                 125

Val Leu Pro Pro Glu Tyr Phe Thr Pro Gln Asp Cys Ser Tyr Phe
130                 135                 140                 145

Pro Asp Asp Phe Met Phe Gly Val Ala Gly Ser Ala Ser Gln Ile Glu
                150                 155                 160

Gly Ala Ile Ala Asp Glu Gly Arg Thr Pro Ser Leu Met Glu Ile Leu
                165                 170                 175

Ile Ser Pro Ser Thr Gly Lys Pro Thr Asn Tyr Val Thr Asn Glu Asn
                180                 185                 190

Tyr Tyr Leu Tyr Lys Gln Asp Ile Glu Arg Leu Ala Ala Met Gly Val
        195                 200                 205

Lys Tyr Tyr Ser Phe Thr Ile Pro Trp Ser Arg Ile Leu Pro Phe Val
210                 215                 220                 225

Leu Glu Gly Thr Pro Leu Asn Gln Gln Gly Leu Asp His Tyr Asp Asp
                230                 235                 240

Leu Ile Asn Phe Val Leu Glu Lys Gly Met Gln Pro Thr Val Thr Leu
                245                 250                 255

Ile His Phe Asp Thr Pro Leu Gln Phe Tyr Gly Asn Asn Leu Ser Thr
                260                 265                 270

Ala Ala Asp Pro Pro Leu Ile Gly Tyr Thr Asn Gly Ala Tyr Gln Asn
        275                 280                 285

Glu Thr Phe Glu Asp Ala Phe Val Asn Tyr Gly Lys Ile Val Met Thr
290                 295                 300                 305

His Phe Ala Asp Arg Val Pro Val Trp Phe Thr Phe Asn Glu Pro Leu
                310                 315                 320

Leu Tyr Cys Asp Asn Gly Lys Ser Val Asn Thr Val Val Lys Ala His
                325                 330                 335

Ala Arg Leu Tyr His Phe Tyr His Glu Glu Ile Asn Gly Thr Gly Lys
        340                 345                 350

Val Gly Ile Lys Phe Asn Asp Asn Phe Gly Val Pro Arg Asp Pro Gln
        355                 360                 365

Asp Ser Ser Asp Val Asp Ala Ala Asn His Phe Asn Glu Phe Gln Leu
370                 375                 380                 385

Ala Thr Phe Ala Asn Pro Ile Phe Leu Gly Lys Asp Tyr Pro Glu Ala
                390                 395                 400

Phe Lys Met Thr Val Pro Asp Tyr Val Pro Leu Ser Gln Glu Asp Leu
                405                 410                 415

Glu Tyr Ile Gly Gly Thr Ser Asp Phe Leu Gly Ile Asp Pro Tyr Thr
        420                 425                 430

Ala Thr Val Val Ser Pro Pro Asp Gly Ile Ala Val Cys Ala Ala
        435                 440                 445

Asn Thr Ser Asp Pro Leu Phe Pro Tyr Cys Val Glu Gln Ser Thr Leu
```

```
                450            455            460            465

Thr Ser Thr Gly Trp Asn Ile Gly Tyr Arg Ser Gln Thr Tyr Val Tyr
                            470            475            480

Ile Thr Pro Lys Tyr Leu Arg Thr Tyr Leu Ser Tyr Leu Trp Asn Thr
                            485            490            495

Phe Gln His Pro Val Met Ile Thr Glu Phe Gly Tyr Pro Val Phe Gly
                            500            505            510

Glu Ala Asp Lys Glu Asp Leu Ser Asp Gln Leu Tyr Asp Leu Pro Arg
                            515            520            525

Ser Tyr Tyr Tyr Leu Ser Phe Met Ser Glu Val Leu Lys Ala Ile Trp
            530            535            540            545

Glu Asp Asn Val His Val Leu Gly Ala Phe Ala Trp Ser Phe Ala Asp
                            550            555            560

Asn Trp Glu Phe Gly Asp Tyr Ala Gln Gln Phe Gly Ile Gln Val Val
                            565            570            575

Asn Arg Thr Thr Gln Glu Arg Tyr Tyr Lys Lys Ser Phe Phe Asp Leu
                            580            585            590

Val Asp Phe Val Ala Ala Arg Thr Lys Ser
                            595            600

<210> SEQ ID NO 35
<211> LENGTH: 966
<212> TYPE: DNA
<213> ORGANISM: Botryosphaeria rhodina
<220> FEATURE:
<221> NAME/KEY: CDS
<222> LOCATION: (1)..(966)
<220> FEATURE:
<221> NAME/KEY: sig_peptide
<222> LOCATION: (1)..(63)
<220> FEATURE:
<221> NAME/KEY: mat_peptide
<222> LOCATION: (64)..(966)

<400> SEQUENCE: 35 atg ttg aat ctg aag atc ctc gcg acc tcg ttc ctc cct ctc ctc ccg      48
Met Leu Asn Leu Lys Ile Leu Ala Thr Ser Phe Leu Pro Leu Leu Pro
    -20            -15                -10 acc ctg gtg agc gga tat gcc aat ccc ggg gcc tgc tca ggg act tgc      96
Thr Leu Val Ser Gly Tyr Ala Asn Pro Gly Ala Cys Ser Gly Thr Cys
-5                -1  1            5                  10 gtg aac acg cac gac ccc tcg atc att cgc cgc tcc gat ggc aca tac     144
Val Asn Thr His Asp Pro Ser Ile Ile Arg Arg Ser Asp Gly Thr Tyr
            15                20            25 ttc cgc ttc tcg acg ggc ggc aag atc gcc atc cac act gcg cca gac     192
Phe Arg Phe Ser Thr Gly Gly Lys Ile Ala Ile His Thr Ala Pro Asp
        30            35            40 atc acg gga cca tgg act tac aag gga gct gct ctg ccc gac ggc tcg     240
Ile Thr Gly Pro Trp Thr Tyr Lys Gly Ala Ala Leu Pro Asp Gly Ser
    45            50            55 agc att gac ctc gct ggc aaa gac gac ctc tgg gca ccc agc gtc cac     288
Ser Ile Asp Leu Ala Gly Lys Asp Asp Leu Trp Ala Pro Ser Val His
60            65            70            75 cag atc gga agc ctg tac tac ctt tac tac tcg gtg agc acg ttt ggg     336
Gln Ile Gly Ser Leu Tyr Tyr Leu Tyr Tyr Ser Val Ser Thr Phe Gly
            80            85            90 tcg cag aac tcg gca att gga ctg gcg cgg tcg tcg acg atg gac gtg     384
Ser Gln Asn Ser Ala Ile Gly Leu Ala Arg Ser Ser Thr Met Asp Val
        95            100            105 ggc agc tgg acg gac gtg gga agc acg ggc atc aag tcg gac tcg tcg     432
Gly Ser Trp Thr Asp Val Gly Ser Thr Gly Ile Lys Ser Asp Ser Ser
```

```
                110                 115                  120
aag ccg tac aac gcg att gat ccg gcg ctg atc aac gcc gac ggc acg        480
Lys Pro Tyr Asn Ala Ile Asp Pro Ala Leu Ile Asn Ala Asp Gly Thr
    125                 130                 135 tac ctc ctc act ttc ggg tcg ttc tgg aag gac ctg tac cag gtg ccg        528
Tyr Leu Leu Thr Phe Gly Ser Phe Trp Lys Asp Leu Tyr Gln Val Pro
140                 145                 150                 155 atg aag acc acg ccg acg gct gca agc ggg tcg gcg tac caa gtg gcg        576
Met Lys Thr Thr Pro Thr Ala Ala Ser Gly Ser Ala Tyr Gln Val Ala
                160                 165                 170 tac gac ccg gtc agc acg gcg gaa gag ggc ccg ttc atc ttc aag tac        624
Tyr Asp Pro Val Ser Thr Ala Glu Glu Gly Pro Phe Ile Phe Lys Tyr
            175                 180                 185 ggc agc tac tac tac ctc ttc tac tcc aag ggc aag tgc tgc ggc tac        672
Gly Ser Tyr Tyr Tyr Leu Phe Tyr Ser Lys Gly Lys Cys Cys Gly Tyr
        190                 195                 200 gac agc tcc agg ccg gcg gcg gga gag gag tac aag atc atg gtc tgc        720
Asp Ser Ser Arg Pro Ala Ala Gly Glu Glu Tyr Lys Ile Met Val Cys
    205                 210                 215 cgg tcg tcc aag gcc acg ggc gga ttt gtc gac aag agc gga aca tcg        768
Arg Ser Ser Lys Ala Thr Gly Gly Phe Val Asp Lys Ser Gly Thr Ser
220                 225                 230                 235 tgc acc aac gga ggc ggg aca gtc gtt ttg gaa tcg cac ggc aac gtt        816
Cys Thr Asn Gly Gly Gly Thr Val Val Leu Glu Ser His Gly Asn Val
                240                 245                 250 tac gga ccc gga ggc caa gga gtc tac gac gat ccc aca tac ggg ccg        864
Tyr Gly Pro Gly Gly Gln Gly Val Tyr Asp Asp Pro Thr Tyr Gly Pro
            255                 260                 265 att ctc tac tat cac tac gtc gtc acg acc atc gga tac gcc gac ggc        912
Ile Leu Tyr Tyr His Tyr Val Val Thr Thr Ile Gly Tyr Ala Asp Gly
        270                 275                 280 cag aag cag ttc ggg tgg aac aag atc aat ttc tcc agc ggt tgg ccg        960
Gln Lys Gln Phe Gly Trp Asn Lys Ile Asn Phe Ser Ser Gly Trp Pro
    285                 290                 295 gtc gtg                                                                 966
Val Val
300

<210> SEQ ID NO 36
<211> LENGTH: 322
<212> TYPE: PRT
<213> ORGANISM: Botryosphaeria rhodina

<400> SEQUENCE: 36

Met Leu Asn Leu Lys Ile Leu Ala Thr Ser Phe Leu Pro Leu Leu Pro
    -20                 -15                 -10

Thr Leu Val Ser Gly Tyr Ala Asn Pro Gly Ala Cys Ser Gly Thr Cys
-5                  -1  1                5                  10

Val Asn Thr His

-continued

```
                 95                 100                 105
Gly Ser Trp Thr Asp Val Gly Ser Thr Gly Ile Lys Ser Asp Ser Ser
            110                 115                 120

Lys Pro Tyr Asn Ala Ile Asp Pro Ala Leu Ile Asn Ala Asp Gly Thr
        125                 130                 135

Tyr Leu Leu Thr Phe Gly Ser Phe Trp Lys Asp Leu Tyr Gln Val Pro
140                 145                 150                 155

Met Lys Thr Thr Pro Thr Ala Ala Ser Gly Ser Ala Tyr Gln Val Ala
                160                 165                 170

Tyr Asp Pro Val Ser Thr Ala Glu Glu Gly Pro Phe Ile Phe Lys Tyr
            175                 180                 185

Gly Ser Tyr Tyr Tyr Leu Phe Tyr Ser Lys Gly Lys Cys Cys Gly Tyr
        190                 195                 200

Asp Ser Ser Arg Pro Ala Ala Gly Glu Glu Tyr Lys Ile Met Val Cys
        205                 210                 215

Arg Ser Ser Lys Ala Thr Gly Gly Phe Val Asp Lys Ser Gly Thr Ser
220                 225                 230                 235

Cys Thr Asn Gly Gly Gly Thr Val Val Leu Glu Ser His Gly Asn Val
                240                 245                 250

Tyr Gly Pro Gly Gly Gln Gly Val Tyr Asp Asp Pro Thr Tyr Gly Pro
            255                 260                 265

Ile Leu Tyr Tyr His Tyr Val Val Thr Thr Ile Gly Tyr Ala Asp Gly
        270                 275                 280

Gln Lys Gln Phe Gly Trp Asn Lys Ile Asn Phe Ser Ser Gly Trp Pro
        285                 290                 295

Val Val
300

<210> SEQ ID NO 37
<211> LENGTH: 1368
<212> TYPE: DNA
<213> ORGANISM: Botryosphaeria rhodina
<220> FEATURE:
<221> NAME/KEY: CDS
<222> LOCATION: (1)..(1368)
<220> FEATURE:
<221> NAME/KEY: sig_peptide
<222> LOCATION: (1)..(54)
<220> FEATURE:
<221> NAME/KEY: mat_peptide
<222> LOCATION: (55)..(1368)

<400> SEQUENCE: 37 atg cat ttc cct tcc att tgg agc ctc gcg ctc ctt tca tca tca gcc      48
Met His Phe Pro Ser Ile Trp Ser Leu Ala Leu Leu Ser Ser Ser Ala
                -15                 -10                 -5 ctc gcg tcg ctg cag atc gtc ccg ggc gcc aca tgg act gcc acc aac      96
Leu Ala Ser Leu Gln Ile Val Pro Gly Ala Thr Trp Thr Ala Thr Asn
    -1  1               5                  10 acc gga cag cac ctt cag gcc cat ggt acc ggc atc atc aag gtt ggc     144
Thr Gly Gln His Leu Gln Ala His Gly Thr Gly Ile Ile Lys Val Gly
15                  20                  25                  30 gac acg tac tac atg atc ggc gag gac aag acg aac ggc acc agt ttc     192
Asp Thr Tyr Tyr Met Ile Gly Glu Asp Lys Thr Asn Gly Thr Ser Phe
                35                  40                  45 cag aac gtc aac tgc tac tcg tcc acg aac ctc gtc gaa tgg aag tac     240
Gln Asn Val Asn Cys Tyr Ser Ser Thr Asn Leu Val Glu Trp Lys Tyr
            50                  55                  60 gaa ggc gcc ctg ctc tcc cag acg gcc tcg ggc gat ctc ggt ccc agc     288
Glu Gly Ala Leu Leu Ser Gln Thr Ala Ser Gly Asp Leu Gly Pro Ser
```

```
                       65                  70                  75
cgc gtg gtt gag cgt ccc aag gtc atc tac aac gac cag acc agc aag        336
Arg Val Val Glu Arg Pro Lys Val Ile Tyr Asn Asp Gln Thr Ser Lys
        80                  85                  90 tac gtg ctc tgg atg cac atc gac tcg tcc gac tac aag gac gcc aag        384
Tyr Val Leu Trp Met His Ile Asp Ser Ser Asp Tyr Lys Asp Ala Lys
 95                 100                 105                 110 aca ggc gtc gcc tcc ggc gat agc gtt tgc ggc tcc tac gag tac cac        432
Thr Gly Val Ala Ser Gly Asp Ser Val Cys Gly Ser Tyr Glu Tyr His
                115                 120                 125 ggc agc ttc cgg ccg ttg ggc ttc cag agc agg gat atg ggc ctg ttc        480
Gly Ser Phe Arg Pro Leu Gly Phe Gln Ser Arg Asp Met Gly Leu Phe
        130                 135                 140 aag gac gat gat ggc aag gcg tac ttg atg acc gaa gac cgt gaa aac        528
Lys Asp Asp Asp Gly Lys Ala Tyr Leu Met Thr Glu Asp Arg Glu Asn
                145                 150                 155 ggc ctc cgc atc aac gcc ttg acc gac gac tac ctg aac gtc acc ggc        576
Gly Leu Arg Ile Asn Ala Leu Thr Asp Asp Tyr Leu Asn Val Thr Gly
        160                 165                 170 gac tcc tct gtc tac cgc ttc gac gag aag tac gaa tcc ccc gcc atg        624
Asp Ser Ser Val Tyr Arg Phe Asp Glu Lys Tyr Glu Ser Pro Ala Met
175                 180                 185                 190 gtc aag gtt gac ggg acc tac tac ctc ttc gcc tcc cag ctt acc ggc        672
Val Lys Val Asp Gly Thr Tyr Tyr Leu Phe Ala Ser Gln Leu Thr Gly
                195                 200                 205 tgg aac ccc aac gac aac tac tac gtc aca gcc tcc tcc ctc tcc ggc        720
Trp Asn Pro Asn Asp Asn Tyr Tyr Val Thr Ala Ser Ser Leu Ser Gly
        210                 215                 220 ccc tgg acc tcc tgg aag acc ttc gcc gac gtc ggc tcc aac acc tac        768
Pro Trp Thr Ser Trp Lys Thr Phe Ala Asp Val Gly Ser Asn Thr Tyr
        225                 230                 235 tcc tcg caa acc tcc ttc atc ctc ccc atc acc ggc agc tcc ggc acg        816
Ser Ser Gln Thr Ser Phe Ile Leu Pro Ile Thr Gly Ser Ser Gly Thr
        240                 245                 250 acg tac atg tac cta ggc gac cgc tgg atc agc tcc gcc ctc ttc cgc        864
Thr Tyr Met Tyr Leu Gly Asp Arg Trp Ile Ser Ser Ala Leu Phe Arg
255                 260                 265                 270 agc acc tac atc tgg ctg ccg ctc acg atc gac tcc gcc gca aag acc        912
Ser Thr Tyr Ile Trp Leu Pro Leu Thr Ile Asp Ser Ala Ala Lys Thr
                275                 280                 285 gca tcc atg aag aac gcc gtc aac tgg gtc ccc gac gtc gcc gcc ggc        960
Ala Ser Met Lys Asn Ala Val Asn Trp Val Pro Asp Val Ala Ala Gly
        290                 295                 300 acc tgg gcc gct ggc ccc agc gag acg cag ccg gag ggc gaa gac gcg       1008
Thr Trp Ala Ala Gly Pro Ser Glu Thr Gln Pro Glu Gly Glu Asp Ala
        305                 310                 315 acg ctc agc ggc ggc gcg agg acg gtg acc tgc agt ggg tgc agc ggc       1056
Thr Leu Ser Gly Gly Ala Arg Thr Val Thr Cys Ser Gly Cys Ser Gly
        320                 325                 330 ggg gag ggg gcc ggg tat ctc ggt ggg acg gac tcg ggc gtc gtg acg       1104
Gly Glu Gly Ala Gly Tyr Leu Gly Gly Thr Asp Ser Gly Val Val Thr
335                 340                 345                 350 ttt gcg ggg gtg acg agc gat gcg gcg acg aag tcg tcg gtt cgg gtc       1152
Phe Ala Gly Val Thr Ser Asp Ala Ala Thr Lys Ser Ser Val Arg Val
                355                 360                 365 aag tat cag aat ttg gat agc acc gcg cgg tat gcg gat gtg agc gtt       1200
Lys Tyr Gln Asn Leu Asp Ser Thr Ala Arg Tyr Ala Asp Val Ser Val
        370                 375                 380 aat ggc ggc gcg aag cag agg atc gcg ttt ttg ccg acg gcg aac ggg       1248
Asn Gly Gly Ala Lys Gln Arg Ile Ala Phe Leu Pro Thr Ala Asn Gly
```

```
                385                 390                 395
acg cct ggg agt agc gtt gtg aat ctg gat ttg aag gcg ggc agt gcg    1296
Thr Pro Gly Ser Ser Val Val Asn Leu Asp Leu Lys Ala Gly Ser Ala
    400                 405                 410 aat gag gtg gtt att gag ggc gcg aat ggt ggg tgg gga cct gat gtg    1344
Asn Glu Val Val Ile Glu Gly Ala Asn Gly Gly Trp Gly Pro Asp Val
415                 420                 425                 430 gat cgg att atg gtg ccg cgg tcg                                    1368
Asp Arg Ile Met Val Pro Arg Ser
                435

<210> SEQ ID NO 38
<211> LENGTH: 456
<212> TYPE: PRT
<213> ORGANISM: Botryosphaeria rhodina

<400> SEQUENCE:

-continued

```
                     290                 295                 300
Thr Trp Ala Ala Gly Pro Ser Glu Thr Gln Pro Glu Gly Glu Asp Ala
            305                 310                 315

Thr Leu Ser Gly Gly Ala Arg Thr Val Thr Cys Ser Gly Cys Ser Gly
        320                 325                 330

Gly Glu Gly Ala Gly Tyr Leu Gly Gly Thr Asp Ser Gly Val Val Thr
335                 340                 345                 350

Phe Ala Gly Val Thr Ser Asp Ala Ala Thr Lys Ser Ser Val Arg Val
                355                 360                 365

Lys Tyr Gln Asn Leu Asp Ser Thr Ala Arg Tyr Ala Asp Val Ser Val
            370                 375                 380

Asn Gly Gly Ala Lys Gln Arg Ile Ala Phe Leu Pro Thr Ala Asn Gly
        385                 390                 395

Thr Pro Gly Ser Ser Val Val Asn Leu Asp Leu Lys Ala Gly Ser Ala
    400                 405                 410

Asn Glu Val Val Ile Glu Gly Ala Asn Gly Gly Trp Gly Pro Asp Val
415                 420                 425                 430

Asp Arg Ile Met Val Pro Arg Ser
                435

<210> SEQ ID NO 39
<211> LENGTH: 1248
<212> TYPE: DNA
<213> ORGANISM: Botryosphaeria rhodina
<220> FEATURE:
<221> NAME/KEY: CDS
<222> LOCATION: (1)..(1248)
<220> FEATURE:
<221> NAME/KEY: sig_peptide
<222> LOCATION: (1)..(60)
<220> FEATURE:
<221> NAME/KEY: mat_peptide
<222> LOCATION: (61)..(1248)

<400> SEQUENCE: 39 atg gca acg cgt gca ctc tct acg ttc gtt ttg gcc aac ttt ctg ggc      48
Met Ala Thr Arg Ala Leu Ser Thr Phe Val Leu Ala Asn Phe Leu Gly
-20                 -15                 -10                 -5 tca tgc ctc tct tta gct gtt cca gtc gtg cgc caa agc ggc aaa gtt      96
Ser Cys Leu Ser Leu Ala Val Pro Val Val Arg Gln Ser Gly Lys Val
        -1  1                   5                   10 ggc gtc ctt gat gtt tcc atc cca ccc aac agg aac gat gac caa tac     144
Gly Val Leu Asp Val Ser Ile Pro Pro Asn Arg Asn Asp Asp Gln Tyr
            15                  20                  25 tac acg gtt gat ctc gat ttc gat ggc caa act gtt ccg gtt ctt ctc     192
Tyr Thr Val Asp Leu Asp Phe Asp Gly Gln Thr Val Pro Val Leu Leu
    30                  35                  40 gat act ggc tct gga gat ctc ttc gtt ggg tca aac caa tgc agc acg     240
Asp Thr Gly Ser Gly Asp Leu Phe Val Gly Ser Asn Gln Cys Ser Thr
45                  50                  55                  60 act gat cca gac agt gga tgc tac aac agc cca ttt tac caa atc acc     288
Thr Asp Pro Asp Ser Gly Cys Tyr Asn Ser Pro Phe Tyr Gln Ile Thr
            65                  70                  75 aat gaa acc gtc atc gtt gcg aac gag acg ttc ggc act gtt gtg gga     336
Asn Glu Thr Val Ile Val Ala Asn Glu Thr Phe Gly Thr Val Val Gly
        80                  85                  90 gtt gcc ggc gtg aat gga aat cag tcc atc atg ccc gtt gat ttt gga     384
Val Ala Gly Val Asn Gly Asn Gln Ser Ile Met Pro Val Asp Phe Gly
    95                  100                 105 ggc gtt acc att cca gat ctc gcc act ccc ctt ctt tat tat gcg ggc     432
Gly Val Thr Ile Pro Asp Leu Ala Thr Pro Leu Leu Tyr Tyr Ala Gly
```

```
            110                 115                 120
aag ggc gag ttc cag aat ggg tct ttt gga ggc att ctt ggt gtc tct    480
Lys Gly Glu Phe Gln Asn Gly Ser Phe Gly Gly Ile Leu Gly Val Ser
125                 130                 135                 140 ccg cgc aac gtt tct cgc aac tat tac ttc ttc gag cgg ctt cct cca    528
Pro Arg Asn Val Ser Arg Asn Tyr Tyr Phe Phe Glu Arg Leu Pro Pro
                145                 150                 155 atc gat gcc atg atc aca gaa ggt ctg ttg gag aag ccc gtc ttc tcg    576
Ile Asp Ala Met Ile Thr Glu Gly Leu Leu Glu Lys Pro Val Phe Ser
        160                 165                 170 ctg acc ctg ccg aga ctg gga gat cct gat tcc ata tcc gga aaa ttg    624
Leu Thr Leu Pro Arg Leu Gly Asp Pro Asp Ser Ile Ser Gly Lys Leu
            175                 180                 185 aca ctt ggc gcc atc gag gac gct ccg atc atc gga gac atc tcc tac    672
Thr Leu Gly Ala Ile Glu Asp Ala Pro Ile Ile Gly Asp Ile Ser Tyr
    190                 195                 200 aac gaa atc atc gac gca ccc aac tac ggc tac gag gat gcc cgt ctc    720
Asn Glu Ile Ile Asp Ala Pro Asn Tyr Gly Tyr Glu Asp Ala Arg Leu
205                 210                 215                 220 gcc ccg atg tcc tgg acc tcc cag ctg gag ggc gtg cgc atg aac gga    768
Ala Pro Met Ser Trp Thr Ser Gln Leu Glu Gly Val Arg Met Asn Gly
                225                 230                 235 gtt gag atc aac atg acg cag agc tca atc gac gcg caa ggc cgc tac    816
Val Glu Ile Asn Met Thr Gln Ser Ser Ile Asp Ala Gln Gly Arg Tyr
        240                 245                 250 ctc tcc ctc ttc gac tcg ggc gcc caa acc atc ctc ctc cgc tac caa    864
Leu Ser Leu Phe Asp Ser Gly Ala Gln Thr Ile Leu Leu Arg Tyr Gln
            255                 260                 265 gaa ttc acc gcc gtc gcc gcg ctc ttc aag ggc aag acg att gtg cag    912
Glu Phe Thr Ala Val Ala Ala Leu Phe Lys Gly Lys Thr Ile Val Gln
    270                 275                 280 gac ggc tac gcc gtc tac ttc gac tgc gcc gag ccg cag ctg ctc gag    960
Asp Gly Tyr Ala Val Tyr Phe Asp Cys Ala Glu Pro Gln Leu Leu Glu
285                 290                 295                 300 ctg aac tac cac ggc cgc tgg ttc gcc gtc gac ccg ctc gac ttg ata    1008
Leu Asn Tyr His Gly Arg Trp Phe Ala Val Asp Pro Leu Asp Leu Ile
                305                 310                 315 atc ccc agc gac cat ggt gtg gtc aac ggg acg gtg atg tgc aag tcc    1056
Ile Pro Ser Asp His Gly Val Val Asn Gly Thr Val Met Cys Lys Ser
        320                 325                 330 gcg ctg ggc acg tgg agc agg acg ttt gcg gac tcg att atc ggt gtg    1104
Ala Leu Gly Thr Trp Ser Arg Thr Phe Ala Asp Ser Ile Ile Gly Val
            335                 340                 345 ccg ttt atg cgg aat acg ctg agt gtg ttt gat tac gtg acg gag gat    1152
Pro Phe Met Arg Asn Thr Leu Ser Val Phe Asp Tyr Val Thr Glu Asp
    350                 355                 360 ttg tac agt gtg cag ccg cgc gtg ggg ttg ggg agc ttg acg gat ggc    1200
Leu Tyr Ser Val Gln Pro Arg Val Gly Leu Gly Ser Leu Thr Asp Gly
365                 370                 375                 380 gcg gcg gcg atg gag agg tat gcg ggg ttg tat cag aat agg ttg ttg    1248
Ala Ala Ala Met Glu Arg Tyr Ala Gly Leu Tyr Gln Asn Arg Leu Leu
                385                 390                 395

<210> SEQ ID NO 40
<211> LENGTH: 416
<212> TYPE: PRT
<213> ORGANISM: Botryosphaeria rhodina

<400> SEQUENCE: 40

Met Ala Thr Arg Ala Leu Ser Thr Phe Val Leu Ala Asn Phe Leu Gly
-20                 -15                 -10                 -5
```

```
Ser Cys Leu Ser Leu Ala Val Pro Val Val Arg Gln Ser Gly Lys Val
         -1  1               5                        10
Gly Val Leu Asp Val Ser Ile Pro Pro Asn Arg Asn Asp Asp Gln Tyr
        15              20                  25
Tyr Thr Val Asp Leu Asp Phe Asp Gly Gln Thr Val Pro Val Leu Leu
     30              35                  40
Asp Thr Gly Ser Gly Asp Leu Phe Val Gly Ser Asn Gln Cys Ser Thr
 45              50                  55                      60
Thr Asp Pro Asp Ser Gly Cys Tyr Asn Ser Pro Phe Tyr Gln Ile Thr
             65                  70                  75
Asn Glu Thr Val Ile Val Ala Asn Glu Thr Phe Gly Thr Val Val Gly
             80                  85                  90
Val Ala Gly Val Asn Gly Asn Gln Ser Ile Met Pro Val Asp Phe Gly
         95                 100                 105
Gly Val Thr Ile Pro Asp Leu Ala Thr Pro Leu Leu Tyr Tyr Ala Gly
        110                 115                 120
Lys Gly Glu Phe Gln Asn Gly Ser Phe Gly Gly Ile Leu Gly Val Ser
125             130                 135                     140
Pro Arg Asn Val Ser Arg Asn Tyr Tyr Phe Phe Glu Arg Leu Pro Pro
                145                 150                 155
Ile Asp Ala Met Ile Thr Glu Gly Leu Leu Glu Lys Pro Val Phe Ser
                160                 165                 170
Leu Thr Leu Pro Arg Leu Gly Asp Pro Asp Ser Ile Ser Gly Lys Leu
        175                 180                 185
Thr Leu Gly Ala Ile Glu Asp Ala Pro Ile Ile Gly Asp Ile Ser Tyr
190                 195                 200
Asn Glu Ile Ile Asp Ala Pro Asn Tyr Gly Tyr Glu Asp Ala Arg Leu
205                 210                 215                 220
Ala Pro Met Ser Trp Thr Ser Gln Leu Glu Gly Val Arg Met Asn Gly
                225                 230                 235
Val Glu Ile Asn Met Thr Gln Ser Ser Ile Asp Ala Gln Gly Arg Tyr
                240                 245                 250
Leu Ser Leu Phe Asp Ser Gly Ala Gln Thr Ile Leu Arg Tyr Gln
                255                 260                 265
Glu Phe Thr Ala Val Ala Ala Leu Phe Lys Gly Lys Thr Ile Val Gln
    270                 275                 280
Asp Gly Tyr Ala Val Tyr Phe Asp Cys Ala Glu Pro Gln Leu Leu Glu
285                 290                 295                 300
Leu Asn Tyr His Gly Arg Trp Phe Ala Val Asp Pro Leu Asp Leu Ile
                305                 310                 315
Ile Pro Ser Asp His Gly Val Val Asn Gly Thr Val Met Cys Lys Ser
                320                 325                 330
Ala Leu Gly Thr Trp Ser Arg Thr Phe Ala Asp Ser Ile Ile Gly Val
        335                 340                 345
Pro Phe Met Arg Asn Thr Leu Ser Val Phe Asp Tyr Val Thr Glu Asp
        350                 355                 360
Leu Tyr Ser Val Gln Pro Arg Val Gly Leu Gly Ser Leu Thr Asp Gly
365                 370                 375                 380
Ala Ala Ala Met Glu Arg Tyr Ala Gly Leu Tyr Gln Asn Arg Leu Leu
                385                 390                 395
```

<210> SEQ ID NO 41  
<211> LENGTH: 849  
<212> TYPE: DNA

<213> ORGANISM: Botryosphaeria rhodina
<220> FEATURE:
<221> NAME/KEY: CDS
<222> LOCATION: (1)..(849)
<220> FEATURE:
<221> NAME/KEY: sig_peptide
<222> LOCATION: (1)..(63)
<220> FEATURE:
<221> NAME/KEY: mat_peptide
<222> LOCATION: (64)..(849)

<400> SEQUENCE: 41

```
atg ctt ccg aaa atc gct ctt cag ggt ggc ctc gtg gct ctg ctg gtg    48
Met Leu Pro Lys Ile Ala Leu Gln Gly Gly Leu Val Ala Leu Leu Val
    -20             -15                 -10 caa aca gcc gca gcc caa gta cga tgc gcc act ccc gat ccc cca aaa    96
Gln Thr Ala Ala Ala Gln Val Arg Cys Ala Thr Pro Asp Pro Pro Lys
-5              -1   1               5                  10 gag ctg ctg gag cat gca gcg gag atg aaa gcg caa gaa aag gcg atg   144
Glu Leu Leu Glu His Ala Ala Glu Met Lys Ala Gln Glu Lys Ala Met
            15                  20                  25 aaa gat gct gga att cag caa gcc cgg gcc cct atc aca atc aat gct   192
Lys Asp Ala Gly Ile Gln Gln Ala Arg Ala Pro Ile Thr Ile Asn Ala
        30                  35                  40 tgg ttc cac gtc atc gct gcc tct gac acc gtt gag gat gcc aac ttg   240
Trp Phe His Val Ile Ala Ala Ser Asp Thr Val Glu Asp Ala Asn Leu
    45                  50                  55 act gat gaa atg ctt caa aac caa ctt gag gtg ctc aat tcc aac tac   288
Thr Asp Glu Met Leu Gln Asn Gln Leu Glu Val Leu Asn Ser Asn Tyr
60                  65                  70                  75 gct ccg cac gac atc cag ttc aat ctc tcg ggc aca acc agg act gtc   336
Ala Pro His Asp Ile Gln Phe Asn Leu Ser Gly Thr Thr Arg Thr Val
                80                  85                  90 aac agc agt tgg tct gac aac acc gat acg ctt gtc atg aag aca caa   384
Asn Ser Ser Trp Ser Asp Asn Thr Asp Thr Leu Val Met Lys Thr Gln
            95                  100                 105 ctc cgg aag ggc gat tat gct act ctc aac ttg tat ttc cag agg aaa   432
Leu Arg Lys Gly Asp Tyr Ala Thr Leu Asn Leu Tyr Phe Gln Arg Lys
        110                 115                 120 ctc ccg ggt gac tca tca ggt tac tgc acc ttc cct gga atc gtt gaa   480
Leu Pro Gly Asp Ser Ser Gly Tyr Cys Thr Phe Pro Gly Ile Val Glu
    125                 130                 135 gag ggg acg cta gac ttc ttc aac gac ggc tgc gtg att gac gcc cag   528
Glu Gly Thr Leu Asp Phe Phe Asn Asp Gly Cys Val Ile Asp Ala Gln
140                 145                 150                 155 acc gtg cct gga ggc agc aaa gtc ccg tac aac gag ggg aaa aca gcc   576
Thr Val Pro Gly Gly Ser Lys Val Pro Tyr Asn Glu Gly Lys Thr Ala
                160                 165                 170 acc cat gag gtc ggc cac tgg ttc ggt ctc tac cac aca ttt caa ggc   624
Thr His Glu Val Gly His Trp Phe Gly Leu Tyr His Thr Phe Gln Gly
            175                 180                 185 ggc tgc aac ggc ggc gac ggt att gac gac acg cca gct caa gca agc   672
Gly Cys Asn Gly Gly Asp Gly Ile Asp Asp Thr Pro Ala Gln Ala Ser
        190                 195                 200 tac agc gag ggt tgt ccc gtt ggt agg gac tcg tgt ccg gat ttg cct   720
Tyr Ser Glu Gly Cys Pro Val Gly Arg Asp Ser Cys Pro Asp Leu Pro
    205                 210                 215 gga ttg gac ccg att cac aac tac atg gac tat tca gat gac gct tgc   768
Gly Leu Asp Pro Ile His Asn Tyr Met Asp Tyr Ser Asp Asp Ala Cys
220                 225                 230                 235 tac gaa gaa ttt act cct gat caa gat gct cgc atg cgg tcc aac tgg   816
Tyr Glu Glu Phe Thr Pro Asp Gln Asp Ala Arg Met Arg Ser Asn Trp
                240                 245                 250
```

```
                         -continued gac tac tat cgc gcg gcc gcg cag ggc agt gag                        849
Asp Tyr Tyr Arg Ala Ala Ala Gln Gly Ser Glu
            255                 260

<210> SEQ ID NO 42
<211> LENGTH: 283
<212> TYPE: PRT
<213> ORGANISM: Botryosphaeria rhodina

<400> SEQUENCE: 42

Met Leu Pro Lys Ile Ala Leu Gln Gly Gly Leu Val Ala Leu Leu Val
    -20             -15                 -10

Gln Thr Ala Ala Ala Gln Val Arg Cys Ala Thr Pro Asp Pro Pro Lys
-5          -1  1               5                   10

Glu Leu Leu Glu His Ala Ala Glu Met Lys Ala Gln Glu Lys Ala Met
            15                  20                  25

Lys Asp Ala Gly Ile Gln Gln Ala Arg Ala Pro Ile Thr Ile Asn Ala
        30                  35                  40

Trp Phe His Val Ile Ala Ala Ser Asp Thr Val Glu Asp Ala Asn Leu
    45                  50                  55

Thr Asp Glu Met Leu Gln Asn Gln Leu Glu Val Leu Asn Ser Asn Tyr
60                  65                  70                  75

Ala Pro His Asp Ile Gln Phe Asn Leu Ser Gly Thr Thr Arg Thr Val
            80                  85                  90

Asn Ser Ser Trp Ser Asp Asn Thr Asp Thr Leu Val Met Lys Thr Gln
        95                  100                 105

Leu Arg Lys Gly Asp Tyr Ala Thr Leu Asn Leu Tyr Phe Gln Arg Lys
    110                 115                 120

Leu Pro Gly Asp Ser Ser Gly Tyr Cys Thr Phe Pro Gly Ile Val Glu
    125                 130                 135

Glu Gly Thr Leu Asp Phe Phe Asn Asp Gly Cys Val Ile Asp Ala Gln
140                 145                 150                 155

Thr Val Pro Gly Gly Ser Lys Val Pro Tyr Asn Glu Gly Lys Thr Ala
            160                 165                 170

Thr His Glu Val Gly His Trp Phe Gly Leu Tyr His Thr Phe Gln Gly
        175                 180                 185

Gly Cys Asn Gly Gly Asp Gly Ile Asp Asp Thr Pro Ala Gln Ala Ser
    190                 195                 200

Tyr Ser Glu Gly Cys Pro Val Gly Arg Asp Ser Cys Pro Asp Leu Pro
205                 210                 215

Gly Leu Asp Pro Ile His Asn Tyr Met Asp Tyr Ser Asp Asp Ala Cys
220                 225                 230                 235

Tyr Glu Glu Phe Thr Pro Asp Gln Asp Ala Arg Met Arg Ser Asn Trp
            240                 245                 250

Asp Tyr Tyr Arg Ala Ala Ala Gln Gly Ser Glu
            255                 260

<210> SEQ ID NO 43
<211> LENGTH: 34
<212> TYPE: DNA
<213> ORGANISM: Artificial sequence
<220> FEATURE:
<223> OTHER INFORMATION: Primer SigA2NotU-P

<400> SEQUENCE: 43
tcgcgatccg ttttcgcatt tatcgtgaaa cgct                               34
```

```
<210> SEQ ID NO 44
<211> LENGTH: 33
<212> TYPE: DNA
<213> ORGANISM: Artificial sequence
<220> FEATURE:
<223> OTHER INFORMATION: Primer SigA2NotD-P

<400> SEQUENCE: 44
ccgcaaacgc tggtgaaagt aaaagatgct gaa                          33

<210> SEQ ID NO 45
<211> LENGTH: 20
<212> TYPE: DNA
<213> ORGANISM: Artificial sequence
<220> FEATURE:
<223> OTHER INFORMATION: Primer A

<400> SEQUENCE: 45
agcgtttgcg gccgcgatcc                                         20

<210> SEQ ID NO 46
<211> LENGTH: 21
<212> TYPE: DNA
<213> ORGANISM: Artificial sequence
<220> FEATURE:
<223> OTHER INFORMATION: Primer B

<400> SEQUENCE: 46
ttattcggtc gaaaaggatc c                                       21

<210> SEQ ID NO 47
<211> LENGTH: 34
<212> TYPE: DNA
<213> ORGANISM: Artificial sequence
<220> FEATURE:
<223> OTHER INFORMATION: Primer #166

<400> SEQUENCE: 47
cgcggatcca ccatggtctc cttcaagtcg attc                         34

<210> SEQ ID NO 48
<211> LENGTH: 30
<212> TYPE: DNA
<213> ORGANISM: Artificial sequence
<220> FEATURE:
<223> OTHER INFORMATION: Primer #167

<400> SEQUENCE: 48
ccgctcgagt tactgcacgg taatcgtagc                              30
```

POLYPEPTIDES OF BOTRYOSPHAERIA RHODINA

CROSS-REFERENCE TO RELATED APPLICATIONS

This application is a divisional of U.S. application Ser. No. 11/573,261 filed on Mar. 13, 2007 (now U.S. Pat. No. 7,666,649) which claims priority of 35 U.S.C. 371 national application of PCT/DK2005/00519 filed Aug. 6, 2005, which claims priority or the benefit under 35 U.S.C. 119 of Danish application nos. PA 2004 01197 and PA 2004 01215 filed Aug. 6, 2004 and Aug. 11, 2004 and U.S. provisional application No. 60/622,984 filed Oct. 28, 2004, the contents of which are fully incorporated herein by reference.

FIELD OF THE INVENTION

The present invention relates to functional polypeptides encoded by polynucleotides comprised in the mRNA of *Diplodia gossypina*, syn. *Botryospaeria rhodina* deposited under deposit accession number CBS 274.96. The invention relates further to the polynucleotides and constructs of such polynucleotides encoding such polypeptides or facilitating their expression as well as to method for preparing the polypeptide. Still further the invention relates to compositions comprising the polypeptide and to uses of the polypeptide.

BACKGROUND OF THE INVENTION

*Botryosphaeria rhodina* (Berk. & M. A. Curtis) Arx, (syn. *Diplodia gossypina* Cooke). Very few reports have been published concerning the characterization of this organism; Selbmann et al., 2003 report exopolysaccharide production from *Botryosphaeria rhodina* (Selbmann L, Stingele F, and Petruccioli M (2003) Exopolysaccharide production by filamentous fungi: the example of *Botryosphaeria rhodina*. Antonie van Leeuwenhoek, 84:2, pp. 135-145. A single patent exists on the use of *Botryosphaeria rhodina* to hydroxylate beta Damascone as a flavouring agent for tobacco (CH654567-A). Jasmonic acid can also be produced by fermenting the organism (EP1118672-A). The presence of cellobiohydrolases (WO 03/000941-A2) and lactase (WO 01/49878-A) have been previously reported.

In the pursuit of novel enzymes it is also known to screen for such new enzymes by subjecting potential candidates to specific enzyme assays. This approach is limited to the availability of enzyme assays and does not allow the identification of functional enzymes or polypeptides for which the activity is still unknown.

Further, whole genome sequencing is a known method to obtain the information on all genes from a given microorganism e.g. as described in Fleischmann et al.; Whole genome sequences and assembly of Haemophilus influenzae Rd; Nature 269: 496-512; (1995).

Most enzymes for industrial use are enzymes which are secreted to the medium by a microorganism. However, only a few percent of a microorganisms' genome encodes secreted proteins. For example only approx. 4% of the *Bacillus subtilis* genome or its closest relatives encode secreted proteins (Van Dijl et al.: Protein transport pathways in *Bacillus subtilis*: a genome-based road map; in "*Basillus subtilis* and it's closest relatives"—From genes to cells; p. 337-355; A. L. Sonenshein (ed.); ASM Press 2002).

One disadvantage of genome sequencing is that the vast majority of the obtained sequences encode non secreted proteins.

An additional disadvantage of gemomic sequencing particular to eukaryotes such as fungi is that the genome size is many times larger than a bacterial genome making gene discovery by this method more costly and time consuming.

The random sequencing of cDNAs (Expressed sequence tags or ESTs) is another approach that allows for discovery of secreted proteins. In general, EST approaches suffer two drawbacks with regard to secreted protein identification; 1) Depending on the induction conditions used for the cDNA library sequenced, very few, typically between 0.5%-15% or even 1 and 5% of the cDNAs encode secreted proteins. 2) The clones all come from a cDNA pool derived from mRNAs that are present in the organism in proportion to the induction level of each particular gene.

Also known is signal trapping which is a method to identify genes including nucleotides encoding a signal peptide using a translational fusion to an extracellular reporter gene lacking its own signal (WO 01/77315).

SUMMARY OF THE INVENTION

The genome of a microorganism contains thousands of different genes; some encoding polypeptides some coding for RNAs. Only a limited number of the genes in the genome of a microorganism encode functional polypeptides which are secreted by the microorganism to the surrounding medium serving an external purpose for the microorganism.

Such polypeptides are interesting for industry from the point of view that such polypeptides may be produced in considerable amounts in continuous processes without destroying the cells producing the polypeptides.

It is an object of the present invention to identify and provide polypeptides secreted from *Botryosphaeria rhodina* deposited under deposit accession number CBS 274.96 which have functional purpose for the *Botryosphaeria rhodina* because such polypeptides may not only be used for industrial purposes but they may also be produced in industrially relevant processes and amounts.

The present invention provides in a first aspect an isolated polypeptide selected from the group consisting of:

(a) a polypeptide comprising an amino acid sequence which has at least 90% identity with a sequence of a mature polypeptide comprised in the group consisting of SEQ ID NO: 2, 4, 6, 8, 10, 12, 14, 16, 18, 20, 22, 24, 26, 28, 30 32, 34, 36, 38, 40 and 42; and (b) a polypeptide which is encoded by a nucleotide sequence which hybridize under high stringency conditions with a polynucleotide probe selected from the group consisting of
   (i) the complementary strand to a nucleotide sequence selected from the group of regions of SEQ ID NO: 1, 3, 5, 7, 9, 11, 13, 15, 17, 19, 21, 23, 25, 27, 29, 31, 33, 35, 37, 39 and 41 encoding a mature polypeptide.
   (ii) the complementary strand to the cDNA sequence contained in a nucleotide sequences selected from the group of regions of SEQ ID NO: 1, 3, 5, 7, 9, 11, 13, 15, 17, 19, 21, 23, 25, 27, 29, 31, 33, 35, 37, 39 and 41 encoding a mature polypeptide wherein the polypeptide has a function of the corresponding mature polypeptides comprised in the group consisting of SEQ ID NO: 2, 4, 6, 8, 10, 12, 14, 16, 18, 20, 22, 24, 26, 28, 30 32, 34, 36, 38, 40 and 42.

In a further aspect the invention provides an isolated enzyme selected from the group consisting of:
(a) an enzyme comprising an amino acid sequence which has at least 90% identity with the amino acid sequence of a mature enzyme selected from the group consisting of xylanase, serine esterase, peroxidase, GH 61A polypeptide, GH 61B polypeptide, GH 61C polypeptide, GH 61D polypeptide, beta-glucosidase, endo-arabinase and pepsin peptidase secreted from the strain of *Botryosphaeria rhodina* deposited under CBS accession No. 274.96
(b) a polypeptide which is encoded by a nucleotide sequence which hybridize under high stringency conditions with a polynucleotide probe selected from the group consisting of
(i) the complementary strand to a nucleotide sequence comprised in the strain of *Botryosphaeria rhodina* Deposited under CBS accession No. 274.96 encoding a mature enzyme selected from the group consisting of xylanase, serine esterase, peroxidase, GH 61A polypeptide, GH 61B polypeptide, GH 61C polypeptide, GH 61 D polypeptide, beta-glucosidase, endo-arabinase and pepsin peptidase secreted from that strain;
ii) the complementary strand to the cDNA sequence contained in a nucleotide sequences comprised in the strain of *Botryosphaeria rhodina* Deposited under CBS accession No. 274.96 encoding a mature enzyme selected from the group consisting of xylanase, serine esterase, peroxidase, GH 61A polypeptide, GH 61B polypeptide, GH 61C polypeptide, GH 61D polypeptide, beta-glucosidase, endo-arabinase and pepsin peptidase secreted from that strain;
wherein the enzyme have a function selected from xylanase, serine esterase, peroxidase, GH 61A polypeptide, GH 61B polypeptide, GH 61C polypeptide, GH 61D polypeptide, beta-glucosidase, endo-arabinase and pepsin peptidase.

In further aspects the invention provides a polynucleotide encoding the polypeptide of the invention; a nucleotide construct comprising the polynucleotide encoding the polypeptide, operably linked to one or more control sequences that direct the production of the polypeptide in a host cell; a recombinant expression vector comprising the nucleotide construct of the invention and to a recombinant host cell comprising the nucleotide construct of the invention.

In still further aspects the invention provides a method of preparing a polypeptide of the invention comprising:
(a) cultivating a strain comprising a nucleotide sequence encoding a polypeptide of the invention which strain is capable of expressing and secreting the polypeptide and
(b) recovering the polypeptide.

In still further aspects the invention provide a composition comprising a polypeptide of the invention and a method for preparing such a composition comprising admixing the polypeptide of the invention with an excipient.

In still further aspects the invention provides use of the polypeptide of the invention or a composition comprising said polypeptide in various applications.

Sequence Listing

The present application contains information in the form of a sequence listing, which is appended to the application and also submitted on a data carrier accompanying this application. The contents of the data carrier are fully incorporated herein by reference. The regions of sequences selected from the group consisting of SEQ ID NO: 1, 3, 5, 7, 9, 11, 13, 15, 17, 19, 21, 23, 25, 27, 29, 31, 33, 35, 37, 39 and 41 which encode a mature polypeptide, encodes the mature polypeptides of sequences selected from the group consisting of SEQ ID NO: 2, 4, 6, 8, 10, 12, 14, 16, 18, 20, 22, 24, 26, 28, 30 32, 34, 36, 38, 40 and 42 respectively. The region of SEQ ID NO: 1 encoding a mature polypeptide thus encodes the mature polypeptide sequence comprised in SEQ ID NO:2, the region of SEQ ID NO:3 encoding a mature polypeptide encode the mature polypeptide comprised in SEQ ID NO:4 and so on.

BRIEF DESCRIPTION OF DRAWINGS

No drawings.

DETAILED DESCRIPTION OF THE INVENTION

Definitions

The term "group $A_{DNA}$" as used hereinafter means a group of nucleotide sequences consisting of SEQ ID NO: 1, 3, 5, 7, 9, 11, 13, 15, 17, 19, 21, 23, 25, 27, 29, 31, 33, 35, 37, 39 and 41. Hence when referral is made to a nucleotide sequence comprised in or selected from group of sequences consisting of "group $A_{DNA}$ "(or just comprised in or selected from "group $A_{DNA}$"), it means that the sequence is comprised in or selected from the group of nucleotide sequences consisting of SEQ ID NO: 1, 3, 5, 7, 9, 11, 13, 15, 17, 19, 21, 23, 25, 27, 29, 31, 33, 35, 37, 39 and 41.

The term "group $E_{DNA}$" as used hereinafter means a group of nucleotide sequences consisting of SEQ ID NO: 1, 3, 5, 7, 9, 11, 13, 15, 17, 33, 35, 37, 39 and 41. Hence when referral is made to a nucleotide sequence comprised in or selected from group of sequences consisting of "group $E_{DNA}$ "(or just comprised in or selected from "group $E_{DNA}$"), it means that the sequence is comprised in or selected from the group of nucleotide sequences consisting of SEQ ID NO: 1, 3, 5, 7, 9, 11, 13, 15, 17, 33, 35, 37, 39 and 41.

Like wise the term "group $B_{polypeptide}$" as used hereinafter means a group of polypeptide sequences consisting of SEQ ID NO: 2, 4, 6, 8, 10, 12, 14, 16, 18, 20, 22, 24, 26, 28, 30 32, 34, 36, 38, 40 and 42. Hence when referral is made to a polypetide sequence comprised in or selected from the group of sequences consisting of "group $B_{Polypeptide}$" (or just comprised in or selected from "group $B_{Polypeptide}$") it means that the sequence is comprised in or selected from the group of polypeptide sequences consisting of SEQ ID NO: 2, 4, 6, 8, 10, 12, 14, 16, 18, 20, 22, 24, 26, 28, 30 32, 34, 36, 38, 40 and 42.

Like wise the term "group $D_{polypeptide}$" as used hereinafter means a group of polypeptide sequences consisting of SEQ ID NO: 2, 4, 6, 8, 10, 12, 14, 16, 18, 34, 36, 38, 40 and 42. Hence when referral is made to a polypetide sequence comprised in or selected from the group of sequences consisting of "group $D_{polypeptide}$" (or just comprised in or selected from "group $D_{polypeptide}$") it means that the sequence is comprised in or selected from the group of polypeptide sequences consisting of SEQ ID NO: 2, 4, 6, 8, 10, 12, 14, 16, 18, 34, 36, 38, 40 and 42.

The term "identity" as used herein, is to be understood as the homology between two amino acid sequences or between two nucleotide sequences. For purposes of the present invention, the degree of identity between two amino acid sequences is determined by using AlignX in the program of Vector NTI ver. 7.1 (Informax inc., 7600 Wisconsin Avenue, Suite #1100, Bethesda, Md. 20814, USA). Amino acid alignment is created using the Clustal W algorithm (Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680). The following additional parameters are used: Gap opening penalty of 10, Gap extension penalty of 0.05, Gap separation penalty range of 8. Pairwise alignment parameters were Ktuple=1, gap penalty=3, gap length opening penalty=10, gap extension penalty=0.1, window size=5 and diagonals=5. The degree of identity between two nucleotide sequences is determined using the same algorithm and software package as described above for example with the following settings: Gap penalty of 10, and gap length penalty of 10. Pairwise alignment parameters is Ktuple=3, gap penalty=3 and windows=20.

The term "functional polypeptide" as used herein in the context of the present invention means a polypeptide which can be expressed and secreted by a cell and which constitutes an operational unit capable of operating in accordance with the function it is designed to fulfill by the cell. Optionally, co-factors may be required for the polypeptide to adopt the intended function. One example of functional polypeptides is catalytically active polypeptides or enzymes which help the cell catalyzing reactions in the environment surrounding the cell. Another example could be polypeptides which serve as signal substance. Further examples are polypeptides which function as sensors (receptors) for environmental parameters (chemicals in the environment surrounding the cell) or polypeptides, which are active against other organisms (antimicrobial (poly)peptides) or polypeptides, which contributes to the structural integrity of the cell.

The term "mature region" as used herein about portion of an amino acid sequences or polypeptide means the portion or region or domain or section of the amino acid sequences or polypeptide which is the mature functional polypeptide.

The term "region of nucleotide sequence encoding a mature polypeptide" as used herein means the region of a nucleotide sequence counting from the triplet encoding the first amino acid of a mature polypeptide to the last triplet encoding the last amino acid of a mature polypeptide.

The term "GH" as used about certain enzymes of the present invention, as for example "GH10", is a family classification system for glycosyl hydrolase enzymes made by B. Henrissat. The number following the GH each denotes distinct families. This classification system is well known to the skilled person. See Henrissat B., *A classification of glycosyl hydrolases based on amino-acid sequence similarities*, Biochem. J. 280:309-316 (1991); Henrissat B., Bairoch A, *New families in the classification of glycosyl hydrolases based on amino-acid sequence similarities*, Biochem. J. 293:781-788 (1993); Henrissat B., Bairoch A., *Updating the sequence-based classification of glycosyl hydrolases*, Biochem. J. 316: 695-696 (1996); Davies G., Henrissat B., *Structures and mechanisms of glycosyl hydrolases*, Structure 3:853-859 (1995).

Polypeptides of the Invention

The polypeptides of the invention are all polypeptides secreted by *Botryosphaeria rhodina* CBS 274.96 with the purpose of serving a function for that particular cell.

Among the thousands of potential genes in the genome of *Botryosphaeria rhodina* CBS 274.96 the polynucleotides of this genome encoded 21 secreted functional mature polypeptides comprised in group $B_{Polypeptide}$, which were determined to be functional, that is translated into functional polypeptides and secreted by the chosen host cell.

Accordingly, *Botryosphaeria rhodina* CBS 274.96 expresses and secretes the functional mature polypeptides comprised in group $B_{Polypeptide}$, and in the genome of that particular strain, the regions of sequences of group $A_{DNA}$, encoding a mature polypeptide are the genes encoding the mature polypeptides comprised in the sequences of group $B_{Polypeptide}$. Further in a particular embodiment the genes encoding the mature polypeptides comprised in the sequences of of group $B_{Polypeptide}$ can all be expressed and their corresponding mature polypeptides can be secreted when culturing an *E. coli* host transformed with polynucleotides comprising those regions of the sequences of group $A_{DNA}$ encoding a mature polypeptide. By comparing homology or identity of the sequences of the 21 polypeptide sequences to known sequences the particular function of the polypeptides were annotated. At least 14 of the 21 secreted functional polypeptides were determined to be enzymes and/or enzyme like.

The invention thus provides an isolated polypeptide selected from the group consisting of:
(a) a polypeptide having an amino acid sequence which has at least 90% identity with an amino acid sequence selected from the group consisting of the mature polypeptides comprised in group $B_{Polypeptide}$ and
(b) a polypeptide which is encoded by a nucleotide sequence which hybridize under high stringency conditions with a polynucleotide probe selected from the group consisting of
 (i) the complementary strand to a nucleotide sequence selected from the group consisting of the regions of group $A_{DNA}$ sequences encoding a mature polypeptide,
 (ii) the complementary strand to the cDNA sequence contained in a nucleotide sequences selected from the group consisting of the regions of group $A_{DNA}$ sequences encoding a mature polypeptide;
wherein the polypeptide exhibits the function of the corresponding mature polypeptides of group $B_{Polypeptide}$.

In one particular embodiment the polypeptide of the invention is selected among the enzymes secreted by *Botryosphaeria rhodina* deposited under CBS accession No. 274.96 and isolated by the present inventors, i.e. the group of enzymes consisting of xylanase, serine esterase, peroxidase, GH 61A polypeptide, GH 61B polypeptide, GH 61C polypeptide, GH 61D polypeptide, beta-glucosidase, endo-arabinase and pepsin peptidase.

The invention also provides an isolated enzyme selected from the group consisting of:
(a) an enzyme comprising an amino acid sequence which has at least 90% identity with the amino acid sequence of a mature enzyme selected from the group consisting of xylanase, serine esterase, peroxidase, GH 61A polypeptide, GH 61B polypeptide, GH 61C polypeptide, GH 61D polypeptide, beta-glucosidase, endo-arabinase and pepsin peptidase secreted from the strain of *Botryosphaeria rhodina* Deposited under CBS accession No. 274.96 and
(b) a polypeptide which is encoded by a nucleotide sequence which hybridize under high stringency conditions with a polynucleotide probe selected from the group consisting of
 (i) the complementary strand to a nucleotide sequence comprised in the strain of *Botryosphaeria rhodina* Deposited under CBS accession No. 274.96 encoding a mature enzyme selected from the group consisting of xylanase, serine esterase, peroxidase, GH 61A polypeptide, GH 61B polypeptide, GH 61C polypeptide, GH 61 D polypeptide, beta-glucosidase, endo-arabinase and pepsin peptidase secreted from that strain;
 ii) the complementary strand to the cDNA sequence contained in a nucleotide sequences comprised in the strain of *Botryosphaeria rhodina* Deposited under CBS accession No. 274.96 encoding a mature enzyme selected from the group consisting of xylanase, serine esterase, peroxidase, GH 61A polypeptide, GH 61B polypeptide, GH 61C polypeptide, GH 61D polypeptide, beta-glucosidase, endo-arabinase and pepsin peptidase secreted from that strain and
wherein the enzyme have a function selected from xylanase, serine esterase, peroxidase, GH 61A polypeptide, GH 61B polypeptide, GH 61C polypeptide, GH 61D polypeptide, beta-glucosidase, endo-arabinase and pepsin peptidase.

In a particular embodiment the enzyme is an isolated enzyme selected from the group consisting of:
(a) an enzyme having an amino acid sequence which has at least 90% identity with an amino acid sequence selected from mature enzymes comprised in the sequences of group $D_{Polypeptide}$ and
(b) an enzyme which is encoded by a nucleotide sequence which hybridize under high stringency conditions with a polynucleotide probe selected from the group consisting of
 (i) the complementary strand to a nucleotide sequence selected from the group consisting of the regions of group $E_{DNA}$ sequences encoding a mature enzyme,
 (ii) the complementary strand to the cDNA sequence contained in a nucleotide sequences selected from the group consisting of the regions of group $E_{DNA}$ sequences encoding a mature enzyme;
wherein the enzyme exhibits the function of the corresponding mature enzyme of group $D_{Polypeptide}$.

The polypeptide of the invention is an isolated polypeptide, preferably the preparation of the polypeptide of the invention contains at the most 90% by weight of other polypeptide material with which it may be natively associated (lower percentages of other polypeptide material are preferred, e.g. at the most 80% by weight, at the most 60% by weight, at the most 50% by weight, at the most 40% at the most 30% by weight, at the most 20% by weight, at the most 10% by weight, at the most 9% by weight, at the most 8% by weight, at the most 6% by weight, at the most 5% by weight, at the most 4% at the most 3% by weight, at the most 2% by weight, at the most 1% by weight and at the most ½% by weight). Thus, it is preferred that the isolated polypeptide of the invention is at least 92% pure, i.e. that the polypeptide of the invention constitutes at least 92% by weight of the total polypeptide material present in the preparation, and higher percentages are preferred such as at least 94% pure, at least 95% pure, at least 96% pure, at least 96% pure, at least 97% pure, at least 98% pure, at least 99%, and at the most 99.5% pure. In particular, it is preferred that the polypeptide of the invention is in "essentially pure form", i.e. that the polypeptide preparation is essentially free of other polypeptide material with which it is natively associated. This can be accomplished, for example, by preparing the polypeptide of the invention by means of well-known recombinant methods.

The polypeptide of the invention of the invention may be synthetically made, naturally occurring or a combination thereof. In a particular embodiment the polypeptide of the invention may be obtained from a microorganism such as a prokaryotic cell, an archaeal cell or a eukaryotic cell. The cell may further have been modified by genetic engineering In a particular embodiment, the polypeptide of the invention is an enzyme exhibiting optimum enzyme activity at a temperature within the range from about 10° C. to about 80° C., particularly in the range from about 20° C. to about 60° C.

In a particular embodiment the polypeptide of the invention is an enzyme, which is functionally stabile at a temperature of up to 100° C., in particular up to 80° C., more particularly up to 60° C.

In a particular embodiment the polypeptide of the invention is an enzyme exhibiting at least 20%, in particular at least 40%, such as at least 50%, in particular at least 60%, such as at least 70%, more particularly at least 80%, such as at least 90%, most particularly at least 95%, such as about or at least 100% of the enzyme activity of an enzyme selected from mature enzymes comprised in group $B_{Polypeptide}$.

In a particular embodiment the polypeptide of the invention comprises, contains or consists of an amino acid sequence which has at least 90% identity with a polypeptide sequence selected from the group consisting of mature polypeptides comprised in group $B_{Polypeptide}$; particularly at least 95%, e.g. at least 96%, such as at least 97%, and even more particularly at least 98%, such as at least 99% or even 100% identity.

In another particular embodiment the polypeptide of the invention comprises, contains or consists of an amino acid sequence, which has at least 50% identity with a polypeptide sequence selected from the group consisting of mature polypeptides comprised in group $B_{Polypeptide}$; particularly at least 60%, particularly at least 65%, particularly at least 70%, particularly at least 75%, particularly at least 80%, and even more particularly at least 85% identity.

In a particular embodiment, the amino acid sequence of the polypeptide of the invention differs by at the most ten amino acids (e.g. by ten amino acids), in particular by at the most five amino acids (e.g. by five amino acids), such as by at the most four amino acids (e.g. by four amino acids), e.g. by at the most three amino acids (e.g. by three amino acids), in particular by at the most two amino acids (e.g. by two amino acids), such as by one amino acid from the mature polypeptides comprised in group $B_{Polypeptide}$.

The polypeptide of the invention may be a wild-type polypeptide isolated from a natural source such as the strain *Botryosphaeria rhodina* CBS 274.96 or another wild type strain, however the present invention also encompass artificial variants, where a polypeptide of the invention has been mutated for example by adding, substituting and/or deleting one or more amino acids from said polypeptide while retaining the function of the polypeptide and/or other properties.

Hence, the polypeptide of the invention may be an artificial variant, wherein at least one substitution, deletion and/or insertion of an amino acid has been made to an amino acid sequence comprising or consisting of the mature polypeptide comprised in group $B_{Polypeptide}$.

The polypeptides of the invention also include functional fragments of the amino acid sequences described herein and nucleic acids encoding functional fragments of the amino acid sequences described herein, including fragments of the mature enzymes secreted from the strain of *Botryosphaeria rhodina* Deposited under CBS accession No. 274.96, as described herein, including fragment of an enzyme selected from the group consisting of xylanase, serine esterase, peroxidase, GH 61A polypeptide, GH 61B polypeptide, GH 61C polypeptide, GH 61D polypeptide, beta-glucosidase, endo-arabinase and pepsin peptidase secreted from the strain of *Botryosphaeria rhodina* Deposited under CBS accession No. 274.96.

Artificial variants may be constructed by standard techniques known in the art usually followed by screening and/or characterization. Standard techniques includes classical mutagenesis, e.g. by UV irradiation of the cells or treatment of cells with chemical mutagens as described by Gerhardt et al. (1994); in vivo gene shuffling as described in WO 97/07205; in vitro shuffling as described by Stemmer, (1994) or WO 95/17413, random mutagenesis as described by Eisenstadt E. et al., (1994); PCR techniques as described by Poulsen et al. (1991); family shuffling as described by J. E. Ness, et al, Nature Biotechnology, vol. 17, pp. 893-896 (1999); site-directed mutagenesis as described by Sambrook et al. (1989), Sambrook et al., Molecular Cloning, A Laboratory Manual, Cold Spring Harbor, N.Y. A general description of nucleotide substitution can be found in e.g. Ford et al., 1991, Protein Expression and Purification 2, p. 95-107.

Such standard genetic engineering methods may also be used prepare a diversified library of variant nucleotide sequences from the genes encoding one or more parent enzymes of the invention, expressing the enzyme variants in a suitable host cell and selecting a preferred variant(s). A diversified library can be established by a range of techniques known to the art (Reetz M T; Jaeger K E, in Biocatalysis—from Discovery to Application edited by Fessner W D, Vol. 200, pp. 31-57 (1999); Stemmer, Nature, vol. 370, p.389-391, 1994; Zhao and Arnold, Proc. Natl. Acad. Sci., USA, vol. 94, pp. 7997-8000, 1997; or Yano et al., Proc. Natl. Acad. Sci., USA, vol. 95, pp 5511-5515, 1998).

In a particular embodiment of the invention, amino acid changes (in the artificial variant as well as in wild-type enzyme) are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine and threonine). Amino acid substitutions which do not generally alter and or impair the function of a protein are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a particular embodiment the amino acid changes are of such a nature that the physico-chemical properties of the polypeptides are altered. For example, amino acid changes may be performed, which improve the thermal stability of the enzyme, which alter the substrate specificity, which changes the pH optimum, and the like.

Particularly, the number of such substitutions, deletions and/or insertions in the polypeptide of the invention, particularly in those polypeptides selected from the group consisting of mature polypeptides comprised in group $B_{Polypeptide}$ to produce an artificial variant is at the most 10, such as at the most 9, e.g. at the most 8, more preferably at the most 7, e.g. at the most 6, such as at the most 5, most preferably at the most 4, e.g. at the most 3, such as at the most 2, in particular at the most 1.

In a particular embodiment the artificial variant is a variant, which has an altered, preferably reduced, immunogenicity, especially allergenicity, in animals including man as compared to a parent enzyme. The term "immunogenicity" in this context is to be understood as the artificial variant capability of invoking a an altered, in particular reduced, immunological response when administered to an animal, including intravenous, cutaneous, subcutaneous, oral and intratracheal administration. The term "immunological response" in this context means that the administration of the artificial variant causes an alteration in the immunoglobulin levels in the animal body, such as in IgE, IgG and IgM or an alteration in the cytokine level in the animal body. Methods for mapping immunogenic/antigenic epitopes of a protein, preparing variants with altered immunogenicity and methods for measuring an immunological response is well known to the art and are described e.g. in WO 92/10755, WO 00/26230, WO 00/26354 and WO 01/31989. The term "allergenicity" in this context is to be understood as the artificial variant ability of invoking an altered, in particular reduced, production of IgE in an animal as well as the ability to bind IgE from said animal. Particularly allergenicity arising from intratracheal administration of the polypeptide variant to the animal is particularly of interest (also known as respiratory allergenicity).

In a further embodiment, the polypeptide of the invention is a polypeptide which is encoded by nucleotide sequences which hybridize under at least high stringency conditions, particularly under very high stringency conditions with a polynucleotide probe selected from the group consisting of (i) the complementary strand to a nucleotide sequence selected from the group consisting of the regions of group $A_{DNA}$ sequences encoding a mature polypeptide, (ii) the complementary strand to the cDNA sequence contained in a nucleotide sequences selected from the group consisting of the regions of group $A_{DNA}$ sequences encoding a mature polypeptide;

(iii) a fragment of (i) or (ii) encoding a secreted polypeptide having the function of the corresponding mature polypeptide comprised in group $B_{Polypeptide}$.

(J. Sambrook, E. F. Fritsch, and T. Maniatus, 1989, Molecular Cloning, A Laboratory Manual, 2d edition, Cold Spring Harbor, New York).

In particular, the polypeptide of the invention is encoded by a polynucleotide comprising a nucleotide sequence selected from the group of regions of group $A_{DNA}$ sequences encoding a mature polypeptide or a sequences differing there from by virtue of the degeneracy of the genetic code. More particularly, the polypeptide of the invention is encoded by a polynucleotide consisting of a nucleotide sequence selected from the group of regions of group $A_{DNA}$ sequences encoding a mature polypeptide or a sequence differing there from by virtue of the degeneracy of the genetic code.

The nucleotide sequences of regions of group $A_{DNA}$ sequences encoding a mature polypeptide or a subsequence thereof, as well as the amino acid sequences of the mature polypeptides comprised in group $B_{Polypeptide}$ or a fragment thereof, may be used to design a polynucleotide probe to identify and clone DNA encoding enzymes of the invention from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, more preferably at least 35 nucleotides in length, such as at least 70 nucleotides in length. It is; however, preferred that the polynucleotide probe is at least 100 nucleotides in length. For example, the polynucleotide probe may be at least 200 nucleotides in length, at least 300 nucleotides in length, at least 400 nucleotides in length or at least 500 nucleotides in length. Even longer probes may be used, e.g., polynucleotide probes which are at least 600 nucleotides in length, at least 700 nucleotides in length, at least 800 nucleotides in length, or at least 900 nucleotides in length. Both DNA and RNA probes can be used. The probes are typically labelled for detecting the corresponding gene (for example, with $^{32}P$, $^{3}H$, $^{35}S$, biotin, or avidin).

Thus, a genomic DNA or cDNA library prepared from such other organisms may be screened for DNA, which hybridizes with the probes described above and which encodes enzymes of the invention. Genomic or other DNA from such other organisms may be separated by agarose or polyacrylamide gel electrophoresis, or other separation techniques. DNA from the libraries or the separated DNA may be transferred to, and immobilized, on nitrocellulose or other suitable carrier materials. In order to identify a clone or DNA which has the required homology and/or identity or is homologous and/or identical with nucleotides selected from regions of group $A_{DNA}$ sequences encoding a mature polypeptide, the carrier material with the immobilized DNA is used in a Southern blot.

For purposes of the present invention, hybridization indicates that the nucleotide sequence hybridizes to a labelled polynucleotide probe which again hybridizes to a nucleotide sequence selected from regions of group $A_{DNA}$ sequences encoding a mature polypeptide under high to very high stringency conditions. Molecules to which the polynucleotide probe hybridizes under these conditions may be detected using X-ray film or by any other method known in the art. Whenever the term "polynucleotide probe" is used in the present context, it is to be understood that such a probe contains at least 15 nucleotides.

In an interesting embodiment, the polynucleotide probe is the complementary strand of a nucleotide sequence selected from regions of group $A_{DNA}$ sequences encoding a mature polypeptide.

In another interesting embodiment, the polynucleotide probe is the complementary strand of a nucleotide sequence which encodes an enzyme selected from group $B_{Polypeptide}$. In a further interesting embodiment, the polynucleotide probe is the complementary strand of a mature polypeptide coding region of a nucleotide sequence selected from regions of group $A_{DNA}$ sequences encoding a mature polypeptide.

For long probes of at least 100 nucleotides in length, high to very high stringency conditions are defined as pre-hybridization and hybridization at 42° C. in 5×SSPE, 1.0% SDS, 5× Denhardt's solution, 100 microgram/ml sheared and denatured salmon sperm DNA, following standard Southern blotting procedures. Preferably, the long probes of at least 100 nucleotides do not contain more than 1000 nucleotides. For long probes of at least 100 nucleotides in length, the carrier material is finally washed three times each for 15 minutes using 0.1×SSC, 0.1% SDS at 60° C. (high stringency), in particular washed three times each for 15 minutes using 0.1× SSC, 0.1% SDS at 68° C. (very high stringency).

Although not particularly preferred, it is contemplated that shorter probes, e.g. probes which are from about 15 to 99 nucleotides in length, such as from about 15 to about 70 nucleotides in length, may be also be used. For such short probes, stringency conditions are defined as pre-hybridization, hybridization, and washing post-hybridization at 5° C. to 10° C. below the calculated Tm using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to 99 nucleotides in length, the carrier material is washed once in 6×SCC plus 0.1% SDS for 15 minutes and twice each for 15 minutes using 6×SSC at 5° C. to 10° C. below the calculated Tm.

SEQ ID NO: 2 Xylanase GH10

In a particular embodiment the polypeptide of the invention is a GH10 xylanase comprising or consisting of an amino acid sequence which has at least 90%, particularly at least 95%, more particularly at least 96%, more particularly at least 97%, more particularly at least 98%, more particularly at least 99% or most particularly 100% identity with a GH10 xylanase obtainable from Botryosphaeria rhodina, in particular that strain of Botryosphaeria rhodina deposited under deposit accession number CBS 274.96, more particularly the mature GH10 xylanase comprised in SEQ ID NO: 2. More specifically the mature GH10 xylanase comprise or consists of the sequences from position 1 to 291 of SEQ ID NO: 2. In the present context a GH10 xylanase is defined as an enzyme belonging to the EC 3.2.1.8 enzyme activity grouping. This grouping endohydrolyses 1,4-β-D-xylosidic linkages in xylans. The glycoside hydrolase family 10 (GH10) also comprises enzymes with two other known activities; endo-1,3-beta-xylanase (EC: 3.2.1.32); cellobiohydrolase (EC: 3.2.1.91).

SEQ ID NO: 4 Xylanase GH11

In a particular embodiment the polypeptide of the invention is a GH11 xylanase comprising or consisting of an amino acid sequence which has at least 90%, particularly at least 95%, more particularly at least 96%, more particularly at least 97%, more particularly at least 98%, more particularly at least 99% or most particularly 100% identity with a xylanase GH11 obtainable from Botryosphaeria rhodina, in particular that strain of Botryosphaeria rhodina deposited under deposit accession number CBS 274.96, more particularly the mature GH11 xylanase comprised in SEQ ID NO: 4. More specifically the mature GH11 xylanase comprise or consists of the sequences from position 1 to 202 of SEQ ID NO: 4. In the present context a GH11 xylanase is defined as an enzyme beloning to the EC 3.2.1.8 enzyme activity grouping. This grouping endohydrolyses 1,4-β-D-xylosidic linkages in xylans. Glycoside hydrolase family 11 (GH11) comprises enzymes with only one known activity; xylanase (EC: 3.2.1.8).

SEQ ID NO: 6 Serine Esterase

In a particular embodiment the polypeptide of the invention is a serine esterase, in particular a cutinase or a lipase or a carboxyesterase comprising or consisting of an amino acid sequence which has at least 90%, particularly at least 95%, more particularly at least 96%, more particularly at least 97%, more particularly at least 98%, more particularly at least 99% or most particularly 100% identity with a serine esterase obtainable from Botryosphaeria rhodina, in particular that strain of Botryosphaeria rhodina deposited under deposit accession number CBS 274.96, more particularly the mature serine esterase comprised in SEQ ID NO: 6. More specifically the mature serine esterase comprise or consists of the sequences from position 1 to 352 of SEQ ID NO: 6. In the present context a serine esterase is defined as an enzyme capable of hydrolysing soluble esters in solution (esters which are not in micelle form). More specifically the serin esters are enzymes acting as cutinase (EC 3.1.1.50) or lipase (EC.3.1.1.3) or carboxyesterase capable of hydrolysing wax-esters, cutin, tracyl fats, oils and/or fatty acid chains. In particular the serine esterases contain the classical Ser, His, Asp triad of serine hydrolase, such as tri-acyl lipase/cutinase.

SEQ ID NO: 8 Candida B Type Lipase

In a particular embodiment the polypeptide of the invention is a Candida B type lipase (EC 3.1.1.3) comprising or consisting of an amino acid sequence which has at least 90%, particularly at least 95%, more particularly at least 96%, more particularly at least 97%, more particularly at least 98%, more particularly at least 99% or most particularly 100% identity with a Candida B type Lipase obtainable from *Botryosphaeria rhodina*, in particular that strain of *Botryosphaeria rhodina* deposited under deposit accession number CBS 274.96, more particularly the mature Candida B type Lipase comprised in SEQ ID NO: 8. More specifically the mature Candida B type Lipase comprise or consists of the sequences from position 1 to 431 of SEQ ID NO: 8. In the present context the Candida B type Lipase is defined as an enzyme capable of hydrolysing triglycerides to diacyl glycerides and fatty acid anions, in particular triacylglycerol to diacylglycerol and a fatty acid anion.

SEQ ID NO: 10 Peroxidase

In a particular embodiment the polypeptide of the invention is a peroxidase comprising or consisting of an amino acid sequence which has at least 90%, particularly at least 95%, more particularly at least 96%, more particularly at least 97%, more particularly at least 98%, more particularly at least 99% or most particularly 100% identity with a peroxidase obtainable from *Botryosphaeria rhodina*, in particular that strain of *Botryosphaeria rhodina* deposited under deposit accession number CBS 274.96, more particularly the mature peroxidase comprised in SEQ ID NO: 10. More specifically the mature peroxidase comprises or consists of the sequences from position 1 to 185 of SEQ ID NO: 10. In the present context a peroxidase is defined as an enzyme belonging to defined as a group of enzymes that catalyze oxidation-reduction reactions. As such, they are classified as oxidoreductases. They are given the official EC number 1.11.1. Peroxidases reduce $H_2O_2$ to water while oxidizing a variety of substrates. Thus, peroxidases are oxidoreductases which use $H_2O_2$ as electron acceptor for catalyzing different oxidative reactions.

SEQ ID NO: 12 GH61A Polypeptide

In a particular embodiment the polypeptide of the invention is a GH61A polypeptide comprising or consisting of an amino acid sequence which has at least 90%, particularly at least 95%, more particularly at least 96%, more particularly at least 97%, more particularly at least 98%, more particularly at least 99% or most particularly 100% identity with a GH61A polypeptide obtainable from *Botryosphaeria rhodina*, in particular that strain of *Botryosphaeria rhodina* deposited under deposit accession number CBS 274.96, more particularly the mature GH61A polypeptide comprised in SEQ ID NO: 12. More specifically the mature GH61A polypeptide comprises or consists of the sequences from position 1 to 218 of SEQ ID NO: 12. In the present context a GH 61A polypeptide is defined as a secreted polypeptide or protein providing one or more of the group of effects selected from:
1) Enhancing degradation of cellulosic materials when used in conjunction with a cellulase or a mixture of cellulases.
2) Increasing solubility of enzymes.
3) Increasing the stability of enzymes
4) Reducing enzyme inhibition.

SEQ ID NO: 14 GH 61B Polypeptide

In a particular embodiment the polypeptide of the invention is a GH 61 B polypeptide comprising or consisting of an amino acid sequence which has at least 90%, particularly at least 95%, more particularly at least 96%, more particularly at least 97%, more particularly at least 98%, more particularly at least 99% or most particularly 100% identity with a GH 61B polypeptide obtainable from *Botryosphaeria rhodina*, in particular that strain of *Botryosphaeria rhodina* deposited under deposit accession number CBS 274.96, more particularly the mature GH 61B polypeptide comprised in SEQ ID NO: 14. More specifically the mature GH 61B polypeptide comprises or consists of the sequences from position 1 to 249 of SEQ ID NO: 14. In the present context a GH 61B polypeptide is defined as a secreted polypeptide or protein providing one or more of the group of effects selected from:
1) Enhancing degradation of cellulosic materials when used in conjunction with a cellulase or a mixture of cellulases.
2) Increasing solubility of enzymes.
3) Increasing the stability of enzymes SEQ ID NO: 16 GH 61C Polypeptide In a particular embodiment the polypeptide of the invention is a GH 61 C polypeptide comprising or consisting of an amino acid sequence which has at least 90%, particularly at least 95%, more particularly at least 96%, more particularly at least 97%, more particularly at least 98%, more particularly at least 99% or most particularly 100% identity with a GH 61C polypeptide obtainable from *Botryosphaeria rhodina*, in particular that strain of *Botryosphaeria rhodina* deposited under deposit accession number CBS 274.96, more particularly the mature GH 61C polypeptide comprised in SEQ ID NO: 16. More specifically the mature GH 61C polypeptide comprises or consists of the sequences from position 1 to 255 of SEQ ID NO: 16. In the present context a GH 61C polypeptide is defined as a secreted polypeptide or protein providing one or more of the group of effects selected from:
1) Enhancing degradation of cellulosic materials when used in conjunction with a cellulase or a mixture of cellulases.
2) Increasing solubility of enzymes.
3) Increasing the stability of enzymes SEQ ID NO: 18 GH 61D Polypeptide In a particular embodiment the polypeptide of the invention is a GH 61 D polypeptide comprising or consisting of an amino acid sequence which has at least 90%, particularly at least 95%, more particularly at least 96%, more particularly at least 97%, more particularly at least 98%, more particularly at least 99% or most particularly 100% identity with a GH 61D polypeptide obtainable from *Botryosphaeria rhodina*, in particular that strain of *Botryosphaeria rhodina* deposited under deposit accession number CBS 274.96, more particularly the mature GH 61 D polypeptide comprised in SEQ ID NO: 18. More specifically the mature GH 61D polypeptide comprises or consists of the sequences from position 1 to 205 of SEQ ID NO: 18. In the present context a GH 61C polypeptide is defined as a secreted polypeptide or protein providing one or more of the group of effects selected from:
1) Enhancing degradation of cellulosic materials when used in conjunction with a cellulase or a mixture of cellulases.
2) Increasing solubility of enzymes.
3) Increasing the stability of enzymes SEQ ID NO:20 Functional Polypeptide In a particular embodiment the polypeptide of the invention is a functional polypeptide comprising or consisting of an amino acid sequence which has at least 90%, particularly at least 95%, more particularly at least 96%, more particularly at least 97%, more particularly at least 98%, more particularly at least 99% or most particularly 100% identity with SEQ ID NO: 20. In particular with the mature functional polypeptide comprised in SEQ ID NO: 20. More specifically the mature functional polypeptide comprises or consists of the sequences from position 1 to 243 of SEQ ID NO: 20.

SEQ ID NO: 22 Functional Polypeptide

In a particular embodiment the polypeptide of the invention is a functional polypeptide comprising or consisting of an amino acid sequence which has at least 90%, particularly at least 95%, more particularly at least 96%, more particularly at least 97%, more particularly at least 98%, more particularly at least 99% or most particularly 100% identity with SEQ ID NO: 22. In particular with the mature functional polypeptide comprised in SEQ ID NO: 22. More specifically the mature functional polypeptide comprises or consists of the sequences from position 1 to 415 of SEQ ID NO: 22.

SEQ ID NO: 24 Functional Polypeptide

In a particular embodiment the polypeptide of the invention is a functional polypeptide comprising or consisting of an amino acid sequence which has at least 90%, particularly at least 95%, more particularly at least 96%, more particularly at least 97%, more particularly at least 98%, more particularly at least 99% or most particularly 100% identity with SEQ ID NO: 24. In particular with the mature functional polypeptide comprised in SEQ ID NO: 24. More specifically the mature functional polypeptide comprises or consists of the sequences from position 1 to 377 of SEQ ID NO: 24.

SEQ ID NO: 26 Functional Polypeptide

In a particular embodiment the polypeptide of the invention is a functional polypeptide comprising or consisting of an amino acid sequence which has at least 90%, particularly at least 95%, more particularly at least 96%, more particularly at least 97%, more particularly at least 98%, more particularly at least 99% or most particularly 100% identity with SEQ ID NO: 26. In particular with the mature functional polypeptide comprised in SEQ ID NO: 26. More specifically the mature functional polypeptide comprises or consists of the sequences from position 1 to 259 of SEQ ID NO: 26.

SEQ ID NO: 28 Functional Polypeptide

In a particular embodiment the polypeptide of the invention is a functional polypeptide comprising or consisting of an amino acid sequence which has at least 90%, particularly at least 95%, more particularly at least 96%, more particularly at least 97%, more particularly at least 98%, more particularly at least 99% or most particularly 100% identity with SEQ ID NO: 28. In particular with the mature functional polypeptide comprised in SEQ ID NO: 28. More specifically the mature functional polypeptide comprises or consists of the sequences from position 1 to 248 of SEQ ID NO: 28.

SEQ ID NO: 30 Functional Polypeptide

In a particular embodiment the polypeptide of the invention is a functional polypeptide comprising or consisting of an amino acid sequence which has at least 90%, particularly at least 95%, more particularly at least 96%, more particularly at least 97%, more particularly at least 98%, more particularly at least 99% or most particularly 100% identity with SEQ ID NO: 30. In particular with the mature functional polypeptide comprised in SEQ ID NO: 30. More specifically the mature functional polypeptide comprises or consists of the sequences from position 1 to 149 of SEQ ID NO: 30.

SEQ ID NO: 32 Functional Polypeptide

In a particular embodiment the polypeptide of the invention is a functional polypeptide comprising or consisting of an amino acid sequence which has at least 90%, particularly at least 95%, more particularly at least 96%, more particularly at least 97%, more particularly at least 98%, more particularly at least 99% or most particularly 100% identity with SEQ ID NO: 32. In particular with the mature functional polypeptide comprised in SEQ ID NO: 32. More specifically the mature functional polypeptide comprises or consists of the sequences from position 1 to 202 of SEQ ID NO: 32.

SEQ ID NO: 34 Beta-glucosidase

In a particular embodiment the polypeptide of the invention is a beta-glucosidase comprising or consisting of an amino acid sequence which has at least 90%, particularly at least 95%, more particularly at least 96%, more particularly at least 97%, more particularly at least 98%, more particularly at least 99% or most particularly 100% identity with a beta-glucosidase obtainable from *Botryosphaeria rhodina*, in particular that strain of *Botryosphaeria rhodina* deposited under deposit accession number CBS 274.96, more particularly the mature beta-glucosidase comprised in SEQ ID NO: 34. More specifically the mature beta-glucosidase comprise or consists of the sequences from position 1 to 603 of SEQ ID NO: 34. In the present context the beta-glucosidase is defined as a beta-D-glucoside glucohydrolase (E.C. 3.2.1.21) which catalyzes the hydrolysis of terminal non-reducing beta-D-glucose residues with the release of beta-D-glucose. For purposes of the present invention, beta-glucosidase activity is determined according to the basic procedure described by Venturi et al., 2002, J. Basic Microbiol. 42: 55-66, except different conditions were employed as described herein. One unit of beta-glucosidase activity is defined as 1.0 micromole of p-nitrophenol produced per minute at 50° C., pH 5 from 4 mM p-nitrophenyl-beta-D-glucopyranoside as substrate in 100 mM sodium citrate, 0.01% Tween-20.

SEQ ID NO: 36 Endo-arabinase

In a particular embodiment the polypeptide of the invention is a endo-arabinase comprising or consisting of an amino acid sequence which has at least 90%, particularly at least 95%, more particularly at least 96%, more particularly at least 97%, more particularly at least 98%, more particularly at least 99% or most particularly 100% identity with a endo-arabinase obtainable from *Botryosphaeria rhodina*, in particular that strain of *Botryosphaeria rhodina* deposited under deposit accession number CBS 274.96, more particularly the mature endo-arabinase comprised in SEQ ID NO: 36. More specifically the mature endo-arabinase comprises or consists of the sequences from position 1 to 301 of SEQ ID NO: 36. In the present context an endo-arabinase is defined as an enzyme capable of hydrolysing arabinan.

SEQ ID NO: 38 Endo-arabinase

In a particular embodiment the polypeptide of the invention is a endo-arabinase comprising or consisting of an amino acid sequence which has at least 90%, particularly at least 95%, more particularly at least 96%, more particularly at least 97%, more particularly at least 98%, more particularly at least 99% or most particularly 100% identity with a endo-arabinase obtainable from *Botryosphaeria rhodina*, in particular that strain of *Botryosphaeria rhodina* deposited under deposit accession number CBS 274.96, more particularly the mature endo-arabinase comprised in SEQ ID NO: 38. More specifically the mature endo-arabinase comprises or consists of the sequences from position 1 to 438 of SEQ ID NO: 38. In the present context an endo-arabinase is defined as an enzyme capable of hydrolysing arabinan.

SEQ ID NO: 40 Al Pepsin Peptidase

In a particular embodiment the polypeptide of the invention is a pepsin peptidase comprising or consisting of an amino acid sequence which has at least 90%, particularly at least 95%, more particularly at least 96%, more particularly at least 97%, more particularly at least 98%, more particularly at least 99% or most particularly 100% identity with a pepsin peptidase obtainable from *Botryosphaeria rhodina*, in particular that strain of *Botryosphaeria rhodina* deposited under deposit accession number CBS 274.96, more particularly the mature pepsin peptidase comprised in SEQ ID NO: 40. More specifically the mature pepsin peptidase comprises or consists of the sequences from position 1 to 396 of SEQ ID NO: 40. In the present context a pepsin peptidase is defined as an enzyme capable of hydrolysing proteins or peptides.

SEQ ID NO: 42 M43 Pepsin Peptidase

In a particular embodiment the polypeptide of the invention is a pepsin peptidase comprising or consisting of an amino acid sequence which has at least 90%, particularly at least 95%, more particularly at least 96%, more particularly at least 97%, more particularly at least 98%, more particularly at least 99% or most particularly 100% identity with a pepsin peptidase obtainable from *Botryosphaeria rhodina*, in particular that strain of *Botryosphaeria rhodina* deposited under deposit accession number CBS 274.96, more particularly the mature pepsin peptidase comprised in SEQ ID NO: 42. More specifically the mature pepsin peptidase comprises or consists of the sequences from position 1 to 262 of SEQ ID NO: 42. In the present context a Pepsin peptidase is defined as an enzyme capable of hydrolysing proteins or peptides.

Polynucleotides

The present invention also relates to polynucleotides comprising or consisting of a nucleotide sequence encoding a polypeptide of the invention. In a particular embodiment, the nucleotide sequence is set forth in the sequences of group $A_{DNA}$ including nucleotide sequences differing there from by virtue of the degeneracy of the genetic code. In a further embodiment the polynucleotide of the invention is a modified nucleotide sequence which comprises or consists of a nucleotide sequence selected from the the regions of group $A_{DNA}$ sequences encoding a mature polypeptide and which comprises at least one modification/mutation compared with the parent nucleotide sequence comprised in the sequences of group $A_{DNA}$.

The techniques used to isolate and/or clone a nucleotide sequence encoding an enzyme are known in the art and include isolation from genomic DNA, preparation from cDNA, or a combination thereof. The cloning of the nucleotide sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: *A Guide to Methods and Application*, Academic Press, New York. Other amplification procedures such as ligase chain reaction (LCR), ligated activated transcription (LAT) and nucleotide sequence-based amplification (NASBA) may be used.

The nucleotide sequence may be obtained by standard cloning procedures used in genetic engineering to relocate the nucleotide sequence from its natural location to a different site where it will be reproduced. The cloning procedures may involve excision and isolation of a desired fragment comprising the nucleotide sequence encoding the polypeptide, insertion of the fragment into a vector molecule, and incorporation of the recombinant vector into a host cell where multiple copies or clones of the nucleotide sequence will be replicated. The nucleotide sequence may be of genomic, cDNA, RNA, semi-synthetic, synthetic origin, or any combinations thereof.

In particular the polynucleotide comprises, preferably consists of, a nucleotide sequence which has at least 50% identity with a nucleotide sequence selected from the regions of group $A_{DNA}$ sequences encoding a mature polypeptide. Particularly, the nucleotide sequence has at least 65% identity, more particularly at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with a nucleotide sequence selected from the regions of group $A_{DNA}$ sequences encoding a mature polypeptide. Particularly, the nucleotide sequence comprises a nucleotide sequence selected from the regions of group $A_{DNA}$ sequences encoding a mature polypeptide. In an even more particular embodiment, the nucleotide sequence consists of a nucleotide sequence selected from the regions of group $A_{DNA}$ sequences encoding a mature polypeptide.

In particular the polynucleotide comprises, preferably consists of, a nucleotide sequence encoding a mature enzyme selected from xylanase, serine esterase, peroxidase, GH 61A polypeptide, GH 61B polypeptide, GH 61C polypeptide, GH 61D polypeptide, beta-glucosidase, endo-arabinase and pepsin peptidase and which has at least 50% identity, particularly at least 65% identity, more particularly at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with a nucleotide sequence encoding a mature enzyme selected from xylanase, serine esterase, peroxidase, GH 61A polypeptide, GH 61B polypeptide, GH 61C polypeptide, GH 61D polypeptide, beta-glucosidase, endo-arabinase and pepsin peptidase secreted from *Botryosphaeria rhodina* deposited under CBS accession No. 274.96 and isolated by the present inventors.

In a particular embodiment the polynucleotide comprises, preferably consists of, a nucleotide sequence encoding a mature enzyme selected from xylanase, serine esterase, peroxidase, GH 61A polypeptide, GH 61B polypeptide, GH 61C polypeptide, GH 61D polypeptide, beta-glucosidase, endo-arabinase and pepsin peptidase and which has at least 50% identity, particularly at least 65% identity, more particularly at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with a nucleotide sequence encoding a mature enzyme selected from from group $D_{Polypeptide}$ sequences.

In a particular embodiment the polynucleotide comprises, preferably consists of, a nucleotide sequence encoding a mature enzyme selected from xylanase, serine esterase, peroxidase, GH 61A polypeptide, GH 61B polypeptide, GH 61C polypeptide, GH 61D polypeptide, beta-glucosidase, endo-arabinase and pepsin peptidase and which has at least 50% identity, particularly at least 65% identity, more particularly at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with a nucleotide sequence selected from $E_{DNA}$ sequences

SEQ ID NO: 1

In a particular embodiment the polynucleotide of the invention encodes a GH 10 xylanase and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 55 to 927 of SEQ ID NO: 1

SEQ ID NO: 3

In a particular embodiment the polynucleotide of the invention encodes a GH11 xylanase and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 58 to 663 of SEQ ID NO: 3

SEQ ID NO: 5

In a particular embodiment the polynucleotide of the invention encodes a serine esterase and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 55 to 1110 of SEQ ID NO: 5

SEQ ID NO: 7

In a particular embodiment the polynucleotide of the invention encodes a lipase and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 55 to 1347 of SEQ ID NO: 7.

SEQ ID NO: 9

In a particular embodiment the polynucleotide of the invention encodes a peroxidase and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 1 to 555 of SEQ ID NO: 9.

SEQ ID NO: 11

In a particular embodiment the polynucleotide of the invention encodes a GH61A polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 49 to 702 of SEQ ID NO: 11.

SEQ ID NO: 13

In a particular embodiment the polynucleotide of the invention encodes a GH 61 B polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 40 to 786 of SEQ ID NO: 13.

SEQ ID NO: 15

In a particular embodiment the polynucleotide of the invention encodes a GH 61C polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 55 to 819 of SEQ ID NO: 15.

SEQ ID NO: 17

In a particular embodiment the polynucleotide of the invention encodes a GH 61D polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 61 to 675 of SEQ ID NO: 17.

SEQ ID NO: 19

In a particular embodiment the polynucleotide of the invention encodes a mature functional polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 1 to 729 of SEQ ID NO: 19.

SEQ ID NO: 21

In a particular embodiment the polynucleotide of the invention encodes a mature functional polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 55 to 1299 of SEQ ID NO: 21.

SEQ ID NO: 23

In a particular embodiment the polynucleotide of the invention encodes a mature functional polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 49 to 1179 of SEQ ID NO: 23.

SEQ ID NO: 25

In a particular embodiment the polynucleotide of the invention encodes a mature functional polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 70 to 846 of SEQ ID NO: 25.

SEQ ID NO: 27

In a particular embodiment the polynucleotide of the invention encodes mature functional polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 58 to 801 of SEQ ID NO: 27.

SEQ ID NO: 29

In a particular embodiment the polynucleotide of the invention encodes a mature functional polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 157 to 603 of SEQ ID NO: 29.

SEQ ID NO: 31

In a particular embodiment the polynucleotide of the invention encodes a mature functional polypeptide and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 55 to 660 of SEQ ID NO: 31.

SEQ ID NO: 33

In a particular embodiment the polynucleotide of the invention encodes a beta-glucosidase and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 46 to 1854 of SEQ ID NO: 33.

SEQ ID NO: 35

In a particular embodiment the polynucleotide of the invention encodes a endo-arabinase and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 64 to 966 of SEQ ID NO: 35.

SEQ ID NO: 37

In a particular embodiment the polynucleotide of the invention encodes a endo-arabinase and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 55 to 1368 of SEQ ID NO: 37.

SEQ ID NO: 39

In a particular embodiment the polynucleotide of the invention encodes a pepsin protease and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 61 to 1248 of SEQ ID NO: 39.

SEQ ID NO: 41

In a particular embodiment the polynucleotide of the invention encodes a pepsin protease and comprises or consists of an nucleotide sequence which has at least 70% identity, more particularly at least 80% identity, more particularly at least 90% identity, more particularly at least 95% identity, more particularly at least 96% identity, more particularly at least 97% identity, more particularly at least 98% identity, more particularly at least 99% identity or most particularly 100% identity with the nucleotide sequence of position 64 to 849 of SEQ ID NO: 41.

Modification of a nucleotide sequence encoding a polypeptide of the present invention may be necessary for the synthesis of a polypeptide which comprises an amino acid sequence that has at least one substitution, deletion and/or insertion as compared to an amino acid sequence selected from mature polypeptide comprised in group $B_{Polypeptide}$.

It will be apparent to those skilled in the art that such modifications can be made to preserve the function of the enzyme i.e. made outside regions critical to the function of the enzyme. Amino acid residues which are essential to the function are therefore preferably not subject to modification, such as substitution. Amino acid residues essential to the function may be identified according to procedures known in the art, such as site-directed mutagenesis or alanine-scanning mutagenesis (see, e.g., Cunningham and Wells, 1989, *Science* 244: 1081-1085). Sites of substrate-enzyme interaction can be determined by analysis of the three-dimensional structure as determined by such techniques as nuclear magnetic resonance analysis, crystallography or photoaffinity labeling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

Moreover, a nucleotide sequence encoding an enzyme of the invention may be modified by introduction of nucleotide substitutions which do not give rise to another amino acid sequence of the enzyme encoded by the nucleotide sequence, but which correspond to the codon usage of the host organism intended for production of the enzyme.

The introduction of a mutation into the nucleotide sequence to exchange one nucleotide for another nucleotide may be accomplished by site-directed mutagenesis using any of the methods known in the art. Particularly useful is the procedure, which utilizes a super coiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with Dpnl, which is specific for methylated and hemimethylated DNA to digest the parental DNA template and to select for mutation-containing synthesized DNA. Other procedures known in the art may also be used. For a general description of nucleotide substitution, one may consult with e.g., Ford et al., 1991, *Protein Expression and Purification* 2: 95-107.

The present invention also relates to a polynucleotide comprising, preferably consisting of, a nucleotide sequence which encodes a polypeptide of the invention and which hybridizes under high stringency conditions, preferably under very high stringency conditions with a polynucleotide probe selected from the group consisting of:

(i) the complementary strand to a nucleotide sequence selected from the group consisting of the regions of group $A_{DNA}$ sequences encoding a mature polypeptide,
(ii) the complementary strand to the cDNA sequence contained in a nucleotide sequences selected from the group consisting of the regions of group $A_{DNA}$ sequences encoding a mature polypeptide,
(iii) a fragment of (i) or (ii) encoding a secreted mature polypeptide having the function of the corresponding mature polypeptides comprised in group $B_{Polypeptide}$
(J. Sambrook, E. F. Fritsch, and T. Maniatus, 1989, Molecular Cloning, A Laboratory Manual, 2d edition, Cold Spring Harbor, New York).

As will be understood, details and particulars concerning hybridization of the nucleotide sequences will be the same or analogous to the hybridization aspects discussed in the section titled "polypeptides of the invention" herein.

The present invention also encompasses a storage medium suitable for use in an electronic device comprising information of the amino acid sequence of polypeptides of the invention or the nucleotide sequences of the polynucleotide of the invention. The storage medium may suitably be a magnetic or optical disk and the electronic device a computing device and the information may in particular be stored on the storage medium in a digital form.

Nucleotide Constructs

The present invention also relates to nucleic acid constructs comprising a nucleotide sequence of the invention operably linked to one or more control sequences that direct the expression of the coding sequence in a suitable host cell under conditions compatible with the control sequences.

A nucleotide sequence encoding an enzyme of the invention may be manipulated in a variety of ways to provide for expression of the enzyme. Manipulation of the nucleotide sequence prior to its insertion into a vector may be desirable or necessary depending on the expression vector. The techniques for modifying nucleotide sequences utilizing recombinant DNA methods are well known in the art.

The control sequence may be an appropriate promoter sequence, a nucleotide sequence that is recognized by a host cell for expression of the nucleotide sequence. The promoter sequence contains transcriptional control sequences, which mediate the expression of the polypeptide. The promoter may be any nucleotide sequence which shows transcriptional activity in the host cell of choice including mutant, truncated, and hybrid promoters, and may be obtained from genes encoding extra cellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the enzyme. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a non-translated region of an mRNA which is important for translation by the host cell. The leader sequence is operably linked to the 5' terminus of the nucleotide sequence encoding the polypeptide. Any leader sequence that is functional in the host cell of choice may be used in the present invention. Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded enzyme into the cell's secretory pathway. The 5' end of the coding sequence of the nucleotide sequence may inherently contain a signal peptide coding region naturally linked in translation reading frame with the segment of the coding region which encodes the secreted enzyme. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the enzyme. However, any signal peptide coding region which directs the expressed enzyme into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a enzyme. The resultant polypeptide may be denoted a pro-enzyme or propolypeptide. A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836.

Where both signal peptide and propeptide regions are present at the amino terminus of a polypeptide, the propeptide region is positioned next to the amino terminus of a polypeptide and the signal peptide region is positioned next to the amino terminus of the propeptide region. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences.

Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Recombinant Expression Vectors

The present invention also relates to recombinant expression vectors comprising the nucleic acid construct of the invention. The various nucleotide and control sequences described above may be joined together to produce a recombinant expression vector, which may include one or more convenient restriction sites to allow for insertion or substitution of the nucleotide sequence encoding the polypeptide at such sites. Alternatively, the nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers that permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an Aspergillus cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6.

The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Recombinant Host Cells

The present invention also relates to recombinant a host cell comprising the nucleic acid construct of the invention, which are advantageously used in the recombinant production of the polypeptides. A vector comprising a nucleotide sequence of the present invention is introduced into a host cell so that the vector is maintained as a chromosomal integrant or as a self-replicating extra-chromosomal vector as described earlier.

The host cell may be a unicellular microorganism, e.g., a prokaryote or a non-unicellular microorganism, e.g., a eukaryote.

Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus*, or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, Ainsworth and Bisby's *Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

In an even more preferred embodiment, the yeast host cell is a *Candida, Hansenula, Kluyveromyces, Pichia, Saccharomyces, Schizosaccharomyces*, or *Yarrowia* cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium*, or *Trichoderma*.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium*

*graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming Fusarium species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods for Preparing Enzyme Polypeptides

The present invention also relates to methods for producing an enzyme of the invention comprising (a) cultivating a strain comprising a nucleotide sequence encoding an enzyme of the invention which strain is capable of expressing and secreting the enzyme and (b) recovering the enzyme. In a particular embodiment the strain is a wild type strain such as the *Botryospaeria rhodina* CBS 274.96, while in another embodiment the strain is a recombinant host cell as described, supra.

In these methods of the invention, the cells are cultivated in a nutrient medium suitable for production of the enzyme using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). As the enzyme is secreted into the nutrient medium, the enzyme can be recovered directly from the medium.

The resulting enzyme may be recovered by methods known in the art. For example, the enzyme may be recovered from the nutrient medium by conventional procedures including, but not limited to, centrifugation, filtration, extraction, spray-drying, evaporation, or precipitation. The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J. -C. Janson and Lars Ryden, editors, VCH Publishers, New York, 1989).

Transgenic Plants

The present invention also relates to a transgenic plant, plant part, or plant cell that has been transformed with a nucleotide sequence encoding an enzyme of the invention so as to express and produce the enzyme. In one embodiment the plant could be used as host for production of enzyme in recoverable quantities. The enzyme may be recovered from the plant or plant part. Alternatively, the plant or plant part containing the recombinant enzyme may be used as such for improving the quality of a food or feed, e.g., improving nutritional value, palatability, and rheological properties, or to destroy an antinutritive factor. In particular the plant or plant parts expressing the enzyme may be used as an improved starting material for production of fuel-alcohols or bio-ethanol The transgenic plant can be dicotyledonous (a dicot) or monocotyledonous (a monocot). Examples of monocot plants are grasses, such as meadow grass (blue grass, Poa), forage grass such as festuca, lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing an enzyme of the invention may be constructed in accordance with methods known in the art. Briefly, the plant or plant cell is constructed by incorporating one or more expression constructs encoding an enzyme of the invention into the plant host genome and propagating the resulting modified plant or plant cell into a transgenic plant or plant cell.

Conveniently, the expression construct is a nucleic acid construct which comprises a nucleotide sequence encoding an enzyme of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the enzyme is desired to be expressed. For instance, the expression of the gene encoding an enzyme of the invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285-294). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from Vicia faba (Conrad et al., 1998, *Journal of Plant Physiology* 152: 708-711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588).

A promoter enhancer element may also be used to achieve higher expression of the enzyme of the invention in the plant. For instance, the promoter enhancer element may be an intron which is placed between the promoter and the nucleotide sequence encoding an enzyme of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38). However, it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated therein the expression construct are selected and regenerated into whole plants according to methods well known in the art.

The present invention also relates to methods for producing an enzyme of the invention comprising (a) cultivating a transgenic plant or a plant cell comprising a nucleotide sequence encoding an enzyme of the invention under conditions conducive for production of the enzyme and (b) recovering the enzyme.

Compositions Comprising Enzyme Polypeptides and Methods for Their Preparation

The invention provide a composition comprising a polypeptide of the invention and an excipient and a method for preparing such a composition comprising admixing the polypeptide of the invention with an excipient. In a particular embodiment the polypeptide of the invention is the major (polypeptide) component of the composition, e.g., a mono-component composition. The excipient in this context is to be understood as any auxilliary agent or compound used to formulate the composition and includes solvent, carriers, stabilizers and the like.

The composition may further comprise one or more additional enzymes, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase.

The compositions may be prepared in accordance with methods known in the art and may be in the form of a liquid or a solid composition. For instance, the enzyme composition may be formulated using methods known to the art of formulating polypeptides and/or pharmaceutical products, e.g. into coated or uncoated granules or micro-granules. The polypeptide of the invention may thus be provided in the form of a granule, preferably a non-dusting granule, a liquid, in particular a stabilized liquid, a slurry or a protected polypeptide. For certain applications, immobilization of the polypeptide on a solid matrix may be preferred.

The polypeptide to be included in the composition may be stabilized in accordance with methods known in the art e.g. by stabilizing the polypeptide in the composition by adding and antioxidant or reducing agent to limit oxidation of the polypeptide or it may be stabilized by adding polymers such as PVP, PVA, PEG or other suitable polymers known to be beneficial to the stability of polypeptides in solid or liquid compositions.

In a further embodiment the composition of the invention is a detergent composition which, in addition to the polypeptide of the invention, comprises a surfactant and optionally compounds selected from the group consisting of builders such as zeolites, bleaching agents such as percarbonate, bleach enhancers such as TAED or NOBS, suds suppressors, fragrants, etc.

In a further embodiment the composition of the invention is a feed composition that in addition to the polypeptide of the invention comprises a cereal or grain product.

In a further embodiment the composition of the invention is a food composition such as a baker's flour composition, a brewed product, a fruit juice, an oil or lard product comprising the polypeptide of the invention.

In a further embodiment the composition of the invention is a pulping composition, which in addition to the polypeptide of the invention, comprises pulp.

In a further embodiment the composition of the invention is a biocidal composition, which comprises in addition to the polypeptide of the invention, an oxidoreductase enhancer.

Use of Enzyme Polypeptides or Compositions Comprising them

In still further aspects the invention provides use of the polypeptides or polynucleotides of the invention or a composition comprising said polypeptides or polynucleotides in various applications, particularly (technical) processes such as processes performed in industry or household, herein under for commercial research purposes. Hence the invention encompasses a process comprising employing a polypeptide of the invention or a polynucleotide of the invention in a (technical) industrial, research or household process.

In one embodiment the polypeptide or the composition of the invention is used for cleaning a cellulosic fabric.

In another embodiment the polypeptide or the composition of the invention is used to prepare a food or feed additive.

In yet another embodiment the polypeptide or the composition of the invention is used for treatment of lignolosic materials and pulp.

Detergent Disclosure

The polypeptide of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the polypeptide of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with the specific position substitutions mentioned therein.

Preferred commercially available protease enzymes include Alcalase®, Savinase®, Primase®, Duralase®, Esperase®, and Kannase® (Novozymes A/S), Maxatase®, Maxacal®, Maxapem®, Properase®, Purafect®, Purafect OxP®, FN2®, and FN3® (Genencor International Inc.).

Lipases: Suitable lipases include those of bacterial or fungal origin. Chemically modified or protein engineered mutants are included. Examples of useful lipases include lipases from *Humicola* (synonym Thermomyces), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g. from *B. sub-tilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™, Lipolase Ultra™ and Lipex™ (Novozymes A/S).

Amylases: Suitable amylases (alpha and/or beta) include those of bacterial or fungal origin. Chemically modified or protein engineered mutants are included. Amylases include, for example, alpha-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with the specific position substitutions mentioned therein.

Commercially available amylases are Duramyl™, Termamyl™, Fungamyl™ and BAN™ (Novozymes A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme®, and Carezyme® (Novozymes), Clazinase®, and Puradax HA® (Genencor International Inc.), and KAC-500(B) ® (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include Guardzyme® (Novozymes A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granule, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a H2O2 source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per litre of wash liquor, preferably 0.05-5 mg of enzyme protein per liter of wash liquor, in particular 0.1-1 mg of enzyme protein per litre of wash liquor.

The enzyme of the invention may additionally be incorporated in the detergent formulations disclosed in WO 97/07202 that is hereby incorporated as reference.

Deposited Microorganism

The following microorganism was deposited by the applicant according to the Budapest Treaty on the International Recognition of the Deposits of Microorganisms for the Purpose of Patent Procedures at Centraalbureau voor Schimmelcultures, Fungal and Yeast Collection, Uppsalalaan 8, 3584 CT Utrecht, P.O.Box 85167, 3508 AD Utrecht, The Netherlands:

| | |
|---|---|
| Name: | *Botryosphaeria rhodina* |
| Synonym: | *Diplodia gossypina* (SBL 274) (Berkeley & M. A. Curtis) von Arx Protolog Arx, J. A. von 1970, "The genera of fungi sporulating in pure culture": 143 |
| Classification: | Dothideaceae, Dothideales, Dothidemycetes; Ascomycota |
| Deposit accession number: | CBS 274.96 |
| Date of deposit: | 12-Mar-1996 |

EXAMPLES

Example 1

Identifying Functional Polypeptides Secreted by *Botryosphaeria rhodina* CBS 274.96

Enzyme Finger Printing of Culture Fluids

An enzyme activity profile was obtained by assaying the culture broth on a wide spectrum of enzyme assays. 96 wells microtitre (MT) plates were prepared with substrates and stored at +10° C. until use. Two different pH varieties were prepared: pH3 and pH7. Following substrates were used: 0.05% AZCL (Mazurine dyed and cross-linked substrates, Megazyme)—Amylose, Arabinan, Beta Glucan (Barley), Casein, Collagen, Curdlan, Dextran, Galactan (potato), Galactomannan (Carob), He-Cellulose, Pullulan, Xylan (oat), and Xyloglucan (AZCL-casein could not be used at pH3, and was therefore left out from these plates).

Preparation of pH3 Substrates:
0.1 g of each AZCL substrate was dissolved in 100 ml 0.2M Succinic acid pH3+10 microlitres TritonX-100 (0.01%), to give a final concentration of 0.1% AZCL.

Preparation of pH7 Substrates:
0.1 g of each AZCL substrate was dissolved in 50 ml sterile H20 plus 10 microlitres TritonX-100 (0.01%). 50 ml 0.4M MOPS pH 7 was added to each 50 ml AZCL substrate, to give a final volume of 100 ml and a final concentration of 0.2M buffer, 0.1% AZCL.

Laccase and lipase activity assays were included and substrates were prepared as follows:

Preparation of Laccase Substrate:
35 ml 0.08 mg/ml Chicago Sky Blue in 0.2 M phosphate/borate-buffer, pH 9, was prepared Preparation of Lipase Substrate:
A polyvinyl alcohol (PVA)/soy bean oil emulsion was prepared by mixing a 2% PVA solution with soy bean oil 3:1.

The oil was emulsified using ULTRA-TURRAX mixer and 12 ml of the emulsion was mixed with 500 ml 0.2M sodium-acetate buffer including 10mM CaCl₂ pH 5.5 and 5 ml 0.2% Crystal Violet solution.

US Sterilin 96-wells MT plates were used with a Multidrop S20 Stacker, Titertek Instruments, Inc., Alabama. 200 microlitres of each AZCL-substrate and of the lipase substrate and 150 microlitres of the laccase substrate were dispensed into MT wells and 30-50 µl culture broth were added to each substrate and incubated over night at 26 degree celcius. Result scores were made the assays as follows: 0: no activity, 1: weak activity, 2: strong activity.

Result table I: Fingerprinting of *D. gossypina* culture broth

| Substrate | Enzyme activity | pH 3 | pH7 |
|---|---|---|---|
| AZCL-Amylose | α-amylase | 0[a] | 1 |
| AZCL-Arabinan (Debranched) | endo-1,5-α-L-arabinanase | 0 | 2 |
| AZCL-Beta-Glucan (Barley) | β-glucanase, lichenase and cellulases | 2 | 1 |
| AZCL-Casein | proteases | Nt[b] | 2 |
| AZCL-Collagen | proteases | 0 | 1 |
| AZCL-Curdlan | endo-1,3-β-D-glucanase | 1 | 0 |
| AZCL-Dextran | endo-1,6-α-D-glucanase (dextranase) | 0 | 0 |
| AZCL-Galactan (Potato) | endo-1,4-β-D-galactanase | 0 | 2 |
| AZCL-Galactomannan (Carob) | endo-1,4-β-D-mannanase | 2 | 2 |
| AZCL-HE-Cellulose | endo-cellulase | 2 | 2 |
| AZCL-Pullulan | limit-dextrinase (pullulanase) | 0 | 0 |
| AZCL-Xylan (Oat Spelts) | endo-1,4-β-D-xylanase | 2 | 2 |
| AZCL-Xyloglucan | endo-cellulases | 0 | 2 |
| Chicago Sky Blue | Laccase | 0 | 0 |
| PVA/soyabean oil | Lipase | 0 | 0 |

[a] result score for the activity assays: 0 = no activity, 1 = weak reaction and 2 = strong reaction
[b] nt = not tested A. cDNA Library Construction cDNA from *Botryosphaeria rhodina* CBS 274.96 was prepared by using standard molecular biology techniques (Ausuble et al. 1995 "Current protocols in molecular biology" Publ.:John Wiley and sons).

Fermentation of the biomass used in the cDNA library production was initiated from an inoculated PDA plate that had been incubated for 7 days at 28 degrees. Several mycelia-PDA agar plugs were inoculated in shake flasks with Mex1 media containing (per litre): 20 g of soy bean, 15 g of wheat bran, 10 g of cellulose Avicel, 5 g of maltodextrin 01, 3 g of bacto peptone, 0.2 g of pluronic PE6100, and 1 gram Olive oil. The flasks were shaken at 150 RPM at 26 degrees. After 7 days the mycelium was harvested by filtration through Miracloth and frozen in liquid nitrogen and stored at −80° C. until use.

RNA isolation: The total RNA was prepared from frozen, powdered mycelium of *Botryospaeria rhodina* by extraction with guanidium thiocyanate followed by ultracentrifugation though a 5.7M CsCl cushion (Chirgwin, J. M., Przbyla, A. E., Macdonlad, R. J., and Ruttwer W. J., *Isolation of biologically active ribonucleic acid from sources enriched in ribonuclease*, Biochemistry 18, 5294-5299, 1979). The polyA enriched RNA was isolated by oligo (dT)-cellulose affinity chromatography (Aviv, H., and Leder, P., *Purification of biologically active globin messenger RNA by chromatography on oligothymidylic acid-cellulose*, Proc. Natl. Acad. Sci. USA 69 (6), 1408-1412, 1972).

Construction of the cDNA library: Double stranded cDNA was synthesized according to the general methods of Gubler U. and Hoffman, B. J., *A simple and very efficient method for generating cDNA libraries*, Gene 25(2-3), 263-269, (1983); Sambrook, J., Fritsch, E. F., and Maniantis, T. *Molecular cloning: A laboratory Manual*, 2$^{nd}$ ed., 1989, Cold Spring Harbor Laboratory, Cold Spring Harbor, N.Y. and Kofod et al. (1994) using a polyA-Not1 primer (Promega, USA). After synthesis, the cDNA was treated with mung bean nuclease, blunt ended with T4 DNA polymerase, and ligated to a 50 fold molar excess of EcoRI adaptors (Invitrogen, USA). The cDNA was cleaved with NotI restriction enzyme (New England Biolabs, USA) according to the manufacturer's instructions and the cDNA size fractionated by agarose gel electrophoresis. cDNA corresponding to 700 bp and larger were excised from the gel and purified using the GFX DNA isolation kit (AP Biotech). The prepared cDNA was then directionally cloned by ligation into EcoRI-NotI cleaved pMHas5. The ligation mixture was electroporated into DH10B cells (Invitrogen) and plated on LB agar with 50 mgs/liter kanamycin. A cDNA plasmid pool was prepared from 30,000 total transformants of the original cDNA-pM-Has5 vector ligation. Plasmid DNA was prepared directly from a pool of colonies recovered from solid LB kanamycin selective media according to the Qiagen protocol for plasmid DNA isolation (Qiagen Inc. GMBH).

Vector used for cloning was pMhas5, which is described in patent WO 03/044049 and has the following features:

| Feature | Location | Description |
|---|---|---|
| CDS | 365-1156 | Kanamycin resistance |
| CDS | 2232-2387 | Beta galactosidase alpha peptide |
| −10 signal | 2189-2192 | Shine Dalgarno |
| promotor | 2101-2189 | Lac promotor |
| misc feature | 626-650 | KanP1 primer for BACE system |

Notable features of this plasmid are the EcoRI-NotI restriction sites proximal to the Shine Dalgarno region of the Lac promoter. This allows EcoRI-NotI adapted cDNAs to be cloned into the vector and the resulting constructs to be actively transcribed and translated in the *E. coli* host.

B. Transposon Construction and Preparation

The rationale behind the methology of Transposon Assisted Signal Trapping (TAST) as described in WO 01/77315 A1 is to fuse all genes within a selected genome with a gene encoding a signalless beta-lactamase via a transposon tag. Hence when growing host cell clones comprising the genes of a genome fused with a gene encoding a signalless beta-lactamase via a transposon tag in an ampicillin containing medium only those clones expressing and secreting a beta-lactamase will survive. However the beta-lactamase will only be secreted if the gene to which the beta-lactamase gene is fused has an intact promotor and ribosome binding site (i.e. a gene which is expressed by the cell to produce a polypeptide in real life), which can be recognized in the host strain, and if the beta-lactamase is translated so that the synthesized polypeptide is transported across the cytoplasma membrane and folded correctly. Hence, when inserting the fused gene into a selected host cell, those clones, which are ampicillin resistant contains a gene which encodes a functional secreted polypeptide.

Usually, when employing the TAST methodology it is even not necessary to express the entire gene. When tagging the genes with a transposon, expression of the N-terminal part of the genes as protein fusion shows that the genes contain intact transcription, translation and secretion sequences. Hence expression of the N-terminal part of the genes as protein fusion is usually regarded as sufficient for assuring expression and secretion of the entire gene.

Thus it can be concluded that the genes obtained by the TAST method actually do encode secreted functional polypeptides.

Construction of a SigA4 Transposon Containing the β-lactamase Reporter Gene:

Following the instructions of WO 01/77315 Al, the construction of a transposon containing a signal-less β-lactamase gene was carried out using standard molecular biology techniques. The signal-less β-lactamase gene was initially PCR amplified from the vector pUC19) using a proofreading polymerase (Pfu Turbo, Stratagene, USA). The resulting PCR fragment contained the restriction sites NotI and EcoRI in order to aid cloning. The plasmid pEntranceposon(Cam$^r$) containing the Entranceposon and the antibiotic resistance markers CAT (encoding chloramphenicol resistance in the transposon) was obtained from Finnzymes, OY (Espoo Finland). The plasmid was digested with the restriction enzymes NotI and EcoRI, gel purified and ligated with the signal-less β-lactamase containing fragment. The ligation was transformed into electro-competent DH10 B cells and the *E. coli* clone containing the recombinant plasmid with the signal-less β-lactamase was identified by restriction analysis and named SigA2.

For transposon preparation, a smaller derivative of SigA2 was constructed, which lacked the bla gene encoding beta-lactamase: Two oligonucleotide primers SigA2NotU-P 5'-TCG CGA TCC GTT TTC GCA TTT ATC GTG AAA CGC T-3' (SEQ ID NO: 43) and SigA2NotD-P 5'-CCG CAA ACG CTG GTG AAA GTA AAA GAT GCT GAA-3' (SEQ ID NO: 44), which bind to the start and stop of the bla gene of SigA2 directing outwards were used PCR amplify SigA2 without the bla gene. A amplificate of approx. 3.6 kb generated in the this PCR reaction was relegated and transformed in to a suitable *E. coli* strain. A plasmid of 3.6 kb was isolated from a transformant which was able to grow on LB chloramphenicol but not on LB ampicillin. This plasmid maintained both BgIII sites and lacks the active bla gene and was called pSig4.

60 microlitres of pSigA4 plasmid DNA preparation with a concentration of 0.3 μg/μl was digested with BgIII and separated on an agarose gel. The SigA2 transposon DNA band of 2 kb was eluted and purified by using the "GFX™PCR, DNA and Gel Band Purification Kit" (Amersham Pharmacia Biotech Inc, USA) according to the instructions of the vendor and eluted in 200 microlitres EB buffer. SigA2 prepared in this manner could be be used for transposon assisted signal trapping (TAST vide infra).

C. Transposon Tagging

The transposon prepared from pSigA4 carries a 5'-truncated bla-gene encoding a β-lactamase from which the secretion signal was removed. The β-lactamase conveys ampicillin resistance on *E. coli* only when the protein is secreted to the periplasm, whereas cytoplasmic expression of β-lactamase does not confer ampicillin resistance. Without a signal sequence, the β-lactamase enzyme will not be transported to the periplasm and therefore the clone will not grow on media containing ampicillin. The signal-less β-lactamase gene was contained within the transposon in such a way that there was a continuous open reading frame between the transposon border and the β-lactamase coding region. In this way the modified transposon, when it transposes into a gene encoding a protein that is secreted, could cause an in-frame fusion with the target gene. This resulted in a fusion gene product that is secreted to the periplasm of *E. coli* and conveys resistance to the ampicillin. If the transposon integrated even in-frame into a gene encoding a non-secreted protein, the respective host will not become ampicillin resistance.

D. Transposon Assisted Signal Trapping of *Botryosphaeria rhodina*

A complete description of transposon assisted signal trapping can be found in WO 01/77315. A cDNA plasmid pool was prepared from 30,000 total transformants of the original cDNA-pMHas5 vector ligation. Plasmid DNA was prepared directly from a pool of colonies recovered from solid LB selective media according to the Qiagen protocol for plasmid DNA isolation (Qiagen Inc.). The plasmid pool was treated with transposon SigA2 and MuA transposase according to the transposase manufacturer's instructions (Finnizyme, Finland).

For the in vitro transposon tagging of the *Botryosphaeria rhodina* CBS 274.96 cDNA library, 4 or 8 microlitres of SigA2 transposon containing approx. 2.6 micrograms DNA were mixed with 1 microlitres of the DNA concentration of the plasmid pool DNA of the *Botryosphaeria rhodina* CBS 274.96 cDNA library, 2 microlitres of Finnzymes MuA Transposase (0.22 micrograms/microlitre) and 5 microlitres of 5× buffer from Finnzymes O Y, Espoo, Finland) in a total volume of 50 microlitres and incubated at 30° C. for 3.5 hours and followed by heat inactivation at 75° C. for 10 min. The DNA was precipitated by addition of 5 microlitres 3M Na-acetate pH 5 and 110 microlitres 96% ethanol and centrifugation for 30 min at 20000 rpm. The pellet was washed and dried and resuspended in 10 microlitres TE buffer.

1.5 microliter of the transposon tagged plasmid pool were electroporated into 20 microliter DH10B ultra-competent cells according to the standard protocol provided with the cells (Gibco-BRL) in a Biorad Gene Pulse device (50 uF, 25 mAmp, 1.8 kV)

Electroporated cells were incubated in SOC media with shaking (28 degrees celcius, 2 hours, 250 rpm) before being plated on selective media. Three agar media were used:

LB+50 microgram pr. ml kanamycin,

LB+kanamycin+15 microgram pr. ml chloramphencol, and/or

LB+kanamycin+chloramphenicol+12.5 microgram pr. ml ampicillin.

From dilution plating of the electroporation onto LB+kanamycin+chloramphenicol media, it was determined that approximately 72.000 colonies were present containing a cDNA library plasmid with a SigA2 transposition per electroporation and that approximately 69 colonies were recovered under triple selection (LB, kanamycin, chorlamphenicol, ampicillin). Further electroporation and plating experiments were performed until 445 colonies, in all, were recovered from the experiment under triple selection. The colonies were miniprepped according to the Qiagen Qiaturbo96 protocol (Qiagen Inc.—USA). Plasmids were sequenced with the transposon forward and reverse primers (primers A and B) according to the procedure disclosed in the examples of international patent application WO 01/77315 (page 28)

Primer A:
AGCGT TTGCG GCCGC GATCC       (SEQ ID NO: 45)

Primer B:
TTATT CGGTC GAAAA GGATC C     (SEQ ID NO: 46)

E. Sequence Assembly and Annotation

DNA sequence was obtained for the reactions on an AB3700 capillary sequencer. Sequences were trimmed to remove vector and transposon sequence and the A and B primer reads for each plasmid. This resulted in 225 assembled sequences which were grouped into 148 contigs by using the program PhredPhrap (Brent Ewing, LaDeana Hillier, Michael C. Wendl, and Phil Green; *Base-calling of automated sequencer traces using phred I. Accuracy assessment*; Genome Research; 8:175-185; 1998; Brent Ewing and Phil Green; *Base-calling of automated sequencer traces using phred II. Error probabilities*; Genome Research 8:186-194; 1998). All 148 contigs were subsequently compared to sequences available in standard public DNA and protein sequences databases (TrEMBL, SWALL, PDB, EnsemblPep, GeneSeqP) by using the program BLASTX 2.0a19MP-WashU [14Jul. 1998] [Build linux-x86 18:51:44 30 Jul. 1998] (Gish, Warren 1994-1997—Unpublished; Gish, Warren and David J. States; *Identification of protein coding regions by database similarity search*; Nat. Genet. 3:266-72; 1993).

The obtained sequences being, the majority of which were functional genes encoding intact and functional polypeptides, by being obtained from ampicillin resistant clones as explained supra, were used as a basis for the manual analysis.

In order to verify that ampicillin resistance of the colonies were from increased beta lactamase activity, beta-lactamase activity was tested in ten different signal trapped clones with different transposon landing sites on the cDNA. Plasmid DNA was re-transformed into One Shot TOP10 chemically competent *E. coli* cells according to the protocol of Invitrogen Life Technologies and the transformation mixture spread on LB agar with kanamycin (50 µg/ml) and chloramphenicol (10 µg/ml). Colonies were replica plated on LB kanamycin, chloramphenicol with 15 (10 µg/ml) ampicillin after 2 days at 28 degrees C. After 3 days at 28 degrees C., the true growers were inoculated into 10 ml LB medium with Kanamycin (50 µg/ml) and chloramphenicol (10 µg/ml), and incubated over night at 37 degrees C., 275 rpm. The overnight culture were diluted 1:100 in fresh LB Kan/CAM medium and grown to OD600=0.5. The cells were harvested by centrifugation and washed once in 0.9% NaCl. Pellet were suspended in sonication buffer (100 mM Tris-HCl, 2 mM EDTA, pH 8.0), the number of cells adjusted to an optical density of OD600=0.5 and sonicated at an of amplitude 1.5 microns using a Soniprep 150, (MSE). The samples were centrifuged at 15.000 rpm for 10 min. and the supernatant used for beta-lactamase assay. The supernatant was mixed with 50 µl nitrocefin chromogenic beta-lactamase substrate. (1 mg/ml in 50% DMSO; 0.05 M $PO_4$ buffer) and 0.1 M $PO_4$ buffer, pH 7.0 up to 1 ml in a plastic cuvette and the change in $Abs_{482}$ was measured in an Ultrospec 3300 pro spectrophotometer (O'Callahan, 1972). The results were as follows:

TABLE IX

β-lactamase activity of clones with different distances between the Shine Dalgarno (SD) sequence and the ATG translation initiation codon and transposon landing site.

| Clones | Transposon landing site on the cDNA (bp) | Distances between SD sequence and the ATG initiation codon (bp) | β-lactamase activity (Normalized to trappant ZY063807) |
|---|---|---|---|
| ZY063832 | 806 | 102 | 5.5 |
| ZY063832 | 650 | 102 | 11.5 |
| ZY063836 | 991 | 35 | 35.5 |
| ZY063836 | 991 | 35 | 4.0 |
| ZY063807 | 851 | 256 | 1.0 |
| ZY063827 | 568 | 8 | 202.0 |
| ZY063816 | 476 | 126 | 16.0 |
| ZY063816 | 634 | 126 | 3.0 |
| ZY065171 | 469 | 9 | 106.5 |
| ZY065171 | 684 | 9 | 52.0 |

The table above illustrates three main points:
1) Beta-lactamase activity can be detected in all ten clones. It should be emphasized that corresponding plasmid containing *E. coli* transformants are resistant to 50 mg/liter ampicillin selection. Combining these two facts, indicates that all ten clones produce an hybrid protein consisting of part of the transposon tagged cDNA fused to the beta lactamase gene in such a manner as to provide an peptide with beta lactamase activity.
2) Because the cDNA of the ten clones were completely sequenced, the landing site of the SigA2 transposon in each clone was established. The 10 clones all had a SigA2 transposon in the correct orientation and in the correct reading frame to promote a hybrid fusion between the N terminal of the native encoded protein and the transposon encoded beta lactamase.
3) In Eukaryotic cDNAs, untranslated upstream (5' UTR) leaders can vary in length from 1 bp to several hundred base pairs. For the cDNA to be optimally translated from the *E. coli* translation elements such as the Shine-Dalgarno region, an optimal distance of between 4 and 11 base pairs before the ATG start codon is optimal. In the table, we can see that 5'UTRs much longer than optimal still allow for some expression of the cDNA hybrid-beta lactamase fusion protein because beta lactamase activity is observed from the transformed *E. coli* in the example.

The obtained nucleotide sequences of the invention are functional genes which encode intact and functional polypeptides, not only for the reasons above, but because they were obtained from ampicillin resistant clone. The clones obtained herein were ampicillin resistant, because after transposon tagging, the genes were fused with the signalless beta-lactamase gene, which is only expressed when fused to a gene with an intact promoter and ribosome-binding site, which can be recognized in the host strain, and translated and transported across the cytoplasm membrane and folded correctly.

Therefore is could be concluded that the genes of the invention actually do encode active secreted polypeptides. For the 16 genes sequence analysis revealed, that in-frame fusion with the signalless beta-lactamase gene was obtained. In addition, the intactness of the genes' open reading frame was confirmed by determining the entire nucleotide sequence.

Example 2

Determining Enzyme Function by Homology

The function of a gene or the encoded polypeptide can be predicted by sequences comparison with genes or polypeptides of known function. Similarities between group $A_{DNA}$ and group $B_{polypeptide}$ sequences and sequences from public and internal databases were analysed, to determine the functionality of the group $A_{DNA}$ and group $B_{polypeptide}$ sequences. The sequence comparison was carried out using the program BLASTX 2.0a19MP-WashU [14 Jul. 1998]. A careful manual analysis of sequence alignments of group $A_{DNA}$ and group $B_{polypeptide}$ sequences to their closest related sequences with known function made it possible to predict the function of these genes and the encoded polypeptides. Even when the overall amino acid identity was below 40%, which can make it difficult to make reliable predictions, it was possible to predict the function of group $A_{DNA}$ and group $B_{polypeptide}$ sequences by carefully analysing and interpreting the amino acid residues in the catalytic sites and/or in important regions of the polypeptide sequences. If the amino acids of the catalytic site of known sequences were also present in the polypeptide of the invention, combined with a sufficient overall amino acid identity, it was concluded that the polypeptide from *Botryosphaeria rhodina* CBS 274.96 had the same function as the known sequence.

Example 3

Preparing Group $B_{polypeptide}$ Polypeptides

To prepare polypeptides from cDNA sequences of a filamentous fungus such as *Botryosphaeria rhodina* CBS 274.96, it was feasible to express the cDNA in yeast or another filamentous fungus. A good choice, serving as a non-exhaustive example, is expression in *Aspergillus oryzae*. The example given below is how a cDNA encoding a xylanase (SEQ ID No: 3) was expressed in *A. oryzae*.

An expression plasmid pDaU71 was used. This plasmid contained (1) the *A. nidulans* amdS gene as selection marker in *Aspergillus*, (2) the yeast URA3 gene, interrupted by the ampicillin resistance gene for selection in *E. coli*, (3) a duplication of the *A. niger* NA2 promoter (neutral amylase) with 3 extra amyR-sites+ the 5' untranslated part of the *A. nidulans* TPI promoter for heterologous expression and (4) the *A. niger* AMG terminator. As template for amplication of the relevant portion of the *Botryosphaeria rhodina* cDNA library pool, the following primers were used in the PCR reaction:

```
Primer #166:
CGCGGATCCACCATGGTCTCCTTCAAGTCGATTC    (SEQ ID NO: 47)

Primer #167:
CCGCTCGAGTTACTGCACGGTAATCGTAGC        (SEQ ID NO: 47)
```

The following conditions were used:
Extensor Hi Fidelity Reddy Load DNA polymerase PCR mix was used according to the manufacturer's instructions (ABGene, Great Britain).

| | |
|---|---|
| cDNA plasmid pool (1 nanogram/microlitre): | 5 microlitre |
| Primer #166 | 1 microlitre |
| Primer #167 | 1 microlitre |
| PCR master mix | 12.5 microlitre |
| Deionised water | 7.5 microlitre |
| Total volume | 25 microlitre |

The reaction was transferred to an MJ Research DNA engine prewarmed to 94° C. and the following cycle was performed:

| | |
|---|---|
| 94° C. | 2 minutes |
| then 25 cycles of | |
| 94° C. | 30 seconds |
| 53° C. | 30 seconds |
| 72° C. | 1 minute |
| then | |
| 72° C. | 10 minutes. |

Five microlitre of product was analyzed on a 1% agarose gel to confirm the correct size and quantify the amount of PCR product produced. The remaining 20 microlitre mixture was GFX purified according to the manufacturer's instructions (AP Pharma). 20 microlitre of the 40 microlitre purified product was used for a standard BamHI-XhoI restriction digest in a 30 microlitre standard overnight digestion reaction. The restricted product was once again purified by GFX and used in a standard ligation recation with BamHI-XhoI restricted and purifed pDau71. The ligation product was transformed into DH10B *E. coli* cells (*E. coli* DH10B or TOP10 (available from Invitrogen) could be used as cloning hosts in construction of the expression vector) and plated on LB ampicillin media. Ten transformants were selected for plasmid DNA purification and were sequenced to confirm the sequence integrity of the insert. One PCR error free clone pPFJo147 was selected for further studies.

*Aspergillus oryzae* strain BECh2, which was constructed as described in WO 00/39322 (BECh2 is derived from strain Aspergillus oryzae JaL228, which is constructed on the basis of the deposited strain *Aspergillus oryzae* IFO 4177 as described in WO 98/12300). Transformation and culture conditions were performed according to Christiansen et al., 1988, Biotechnology 6, 1419-1422 and as described in WO 01/12794-A page 63. After one round of reisolation, 10 ml YPglucose or YPmaltose medium in Nunc tubes were inoculated with spores from the transformants and the cultures were inoculated for 3 days at 30° C.

10 microlitre supernatant samples from the above described 10 ml cultures were subjected to SDS-gel electrophoresis. The gel was stained with SYPRO Orange Protein Gel Stain (Molecular Probes). Several *Aspergillus* transformants had a prominent band on the SDS gel. These positives were further analyzed for xylanase activity by performing an AZCL-wheat arabinoxylan assay at pH 6.0. The substrate, AZCL-Arabinoxylan from wheat (Megazyme), was prepared as a 0.2% w/v suspension in 0.2 M Na-phosphate buffer pH 6.0 +0.01% Triton-X 100. 900 microlitre substrate was preheated to 37° C. in an Eppendorf thermomixer. 100 microlitre crude culture fluid supernatant from the recombinant host strain Bech2 or the different samples was added to the substrate and incubated for 15 min at 37° C. at maximum speed. The reaction mixture was then placed on ice for 2 minutes and then centrifuged for 1 min 20.000×G. 2×200 microlitre supernatant was transferred to a microtitter plate and measured at OD 590. Activity was determined as an increase in absorbance.

Example 4

Determining Xylanase Activity

The culture fluid or a cell lysate of a host strain synthesising and secreting a xylanase in a suitable buffer is used for measuring the activity. A suitable volume of such a sample is spotted on agarose plates which contain the insoluble chromogenic substrate AZCL-Birch xylan (Megazyme™) and a suitable buffer at pH, e.g. pH is 4.5-7.5. The plate is incubated for an appropriate time, e.g. one day, at an appropriate temperature, e.g. 37°C. The activity is visible as blue halos around the spots.

Example 5

Determining Peroxidase Activity

Peroxidase can be determined spectrophotmetricly using the 2,4 dichlorophenol method of Ishida et al., 1987: Ishida, A., N. Futamura, and T. Matsusaka. 1987. Detection of peroxidase activity and its localisation in the forespore envelopes of *Bacillus cereus*. J. Gen. Appl. Microbiol. 33:27-32. As indicator a mixture of 1.0 mM 2.4 Dichlorophenol and 82 mM 4-aminoantipyrene in 100mM potassium phosphate buffer (pH 7.0) can be used while a substrate of hydrogen peroxide (Sigma), 50 mM in 100 mM potassium phosphate buffer (pH7.0) is suitable.

200 microlitre of appropriately diluted culture fluid supernatant is added to a 1 ml plastic cuvette. 200 microlitre of the indicator mixture is added. Reactions are initiated by the addition of 200 microlitre hydrogen peroxide substrate. Changes in absorbance are observed in a standard spectorophotometer measuring at a wavelength of 510 nm.

Example 6

Determining Cellulose Degradation Boosting Effect on Cellulose Degrading Enzymes or Enzyme Mixtures Some secreted proteins demonstrate synergistic action in degradation of cellose in the presence of cellulose degrading enzymes or mixtures thereof. Such secreted proteins may or may not have, in themselves, hydrolase activity. Examples of such secreted proteins and how one detects their cellulose degradation boosting effect can be found in patent application no. U.S. Pat. No. 11/046,124 and corresponding PCT application PCT/US2005/003525 published 30 Jun. 2005, in particular using the examples 24 and anyone from examples 25 to 28, hereby incorporated by reference.

One way of determining this boosting effect is as follows: Culture fluid or a cell lysate of a host strain synthesising and secreting a cellulase boosting polypeptide are concentrated using an Amicon stirred cell equipped with a PM10 membrane, 10 kDa cutoff (Millipore, Billerica, Mass.), and desalted using an Econo-Pac 10DG column (BioRad Laboratories, Hercules, Calif.). After assay of the protein concentration by BCA (bicinchoninic acid, P. K. Smith et al., 1985, *Anal. Biochem.* 150: 76) Protein Assay Kit (Pierce, Rockford, Ill.) using BSA as standard these polypeptide stocks are stored at −20° C. The polypeptides are not further purified, and stocks are added to reaction mixtures based on total protein measured.

Corn stover is pretreated at the U.S. Department of Energy National Renewable Energy Laboratory (NREL) using dilute sulfuric acid. The following conditions are used for the pretreatment: 1.4 wt % sulfuric acid at 165° C. and 107 psi for 8 minutes. According to NREL, the water-insoluble solids in the pretreated corn stover (PCS) contain 56.5% cellulose, 4.6% hemicellulose and 28.4% lignin. Cellulose and hemicellulose are determined by a two-stage sulfuric acid hydrolysis with subsequent analysis of sugars by high performance liquid chromatography using NREL Standard Analytical Procedure #002. Lignin is determined gravimetrically after hydrolyzing the cellulose and hemicellulose fractions with sulfuric acid using NREL Standard Analytical Procedure #003. Prior to enzymatic hydrolysis, the PCS is ished with a large volume of DDI water on a glass filter; finding the dry weight of the water-ished PCS. Milled PCS is prepared from the water-ished PCS by milling in a coffee-grinder and subsequent ishing with deionized water on a 22 µm Millipore Filter (6P Express Membrane, Stericup, Millipore, Bedford, Mass.).

Hydrolysis of PCS is conducted using 1.1 ml Immunoware microtubes (Pierce, Rockford, Ill.) using a total reaction volume of 1.0 ml. In this protocol hydrolysis of PCS (10 mg/ml in 50 mM sodium acetate pH 5.0 buffer) is performed using different protein loadings (expressed as mg of enzyme per gram of PCS) of a test polypeptide of the invention or Celluclast® 1.5 L sample (Novozymes A/S, Bagsvaerd, Denmark) in the presence of 3% *Aspergillus oryzae* beta-glucosidase (recombinantly produced in *Aspergillus oryzae* according to WO 02/095014) of the cellulase protein loading. Screening of polypeptides of the invention for PCS hydrolyzing capability is performed at 50° C. (Isotemp 102S water baths or TS Autoflow $CO_2$ Jacketed Incubator). Typically, reactions are run in quadruplicate and aliquots taken during the course of hydrolysis. PCS hydrolysis reactions are stopped by mixing a 20 µl aliquot of each hydrolyzate with 180 µl of 0.11 M NaOH (stop reagent). Appropriate serial dilutions are generated for each sample and the reducing sugar content determined using a para-hydroxybenzoic acid hydrazide (PHBAH, Sigma, St. Louis, Mo.) assay adapted to a 96 well microplate format as described below. Briefly, a 90 µl aliquot of an appropriately diluted sample is placed in a 96 well conical bottomed microplate. Reactions are initiated by adding 60 µl of 1.5% (w/v) PHBAH in 2% NaOH to each well. Plates are heated uncovered at 95° C. for 10 minutes. Plates are allowed to cool to room temperature (RT) and 50 µl of distilled $H_2O$ added to each well. A 100 µl aliquot from each well is transferred to a flat bottomed 96 well plate and the absorbance at $A_{510nm}$ measured using a SpectraMax Microplate Reader (Molecular Devices, Sunnyvale, Calif.). Glucose standards (0.1-0.0125 mg/ml diluted with 0.4% sodium hydroxide) are used to prepare a standard curve to translate the obtained $A_{410nm}$ values into glucose equivalents. The resultant equivalents are used to calculate the percentage of PCS cellulose conversion for each reaction.

The degree of cellulose conversion to reducing sugar (conversion, %) is calculated using the following equation:

$$\text{Conversion}_{(\%)} = RS_{(mg/ml)} * 100 * 162 / (\text{Cellulose}_{(mg.ml)} * 180) = RS_{(mg/ml)} * 100 / (\text{Cellulose}_{(mg/ml)} * 1.111)$$

In this equation, RS is the concentration of reducing sugar in solution measured in glucose equivalents (mg/ml), and the factor 1.111 reflects the weight gain in converting cellulose to glucose.

To screen for polypeptides of the invention which can enhance Celluclast® 1.5 L performance, PCS hydrolysis reactions (1.0 ml protocol, 10 g of PCS per liter, 50° C., supplemented by addition of 3% of total loading of *Aspergillus oryzae* beta-glucosidase) are performed in which 2.5 mg enzyme loading Celluclast® 1.5L is mixed with 2.5 mg polypeptide loading of each sample (5 mg enzyme loading Total protein per reaction). Celluclast® 1.5 L control reactions consisting of 10 mg enzyme loading, 5 mg enzyme loading and 2.5 mg enzyme loading are measured and their PCS cellulose conversion values recorded for comparison.

Example 7

Determining Lipase Activity

The culture fluid or a cell lysate of a host strain synthesising and secreting a lipase in a suitable buffer is used for measuring the activity.

Lipase assay (PNV assay): 20 microlitres of dilution buffer is pipetted into each well of a 96 well microtiter plate. 5 microlitres of sample (supernatant) is added to the dilution buffer. At the start of the assay 200 microlitres of substrate is added to each well and the plate is mounted into an ELISA reader (a programmable spectrophotometer that can read 96 well plates). Absorbance is measured at 405 nm every 30 seconds for 10 minutes. The slope of the time vs. $abs_{405}$ curve is used as an arbitrary activity unit.

Dilution buffer: 25 ml 2M Tris/HCl pH 7.5, 0.50 ml 2M CaCl2, 2.5 ml 15% Brij 35, H2O ad 500 ml.

Substrate stock solution: 0.1295 g (117 microlitres) p-Nitrophenyl valerate SIGMA N 4377 (density 1.11 g/ml) is dissolved in 10 ml methanol. Store in freezer Substrate: 100 microlitres substrate stock solution is mixed with 10 ml dilution buffer.

Example 8

Determining Protease and Peptidase Activity

The culture fluid or a cell lysate of a host strain synthesising and secreting a peptidase and/or protease, in a suitable buffer having a pH chosen for optimal activity of the peptidase, may be assayed for that activity by spotting a suitable sample volume (for example 20 microliter) on an agarose plate which contain the insoluble chromogenic substrate AZCL-casein (Megazyme™) or AZCL-collagen (Megazyme™) OR Azocoll (Sigma-Aldrich)—e.g at a level of 0.1% w/w. The plate is incubated for an appropriate time, e.g. one day, at a temperature suitable for the function of the peptidase, e.g. 37° C. The activity is visible as blue halos around the spots. As an alternative to AZCL-casein and AZCL-collagen (Megazyme™) non-labelled casein or non-labelled collagene can be used. On non-labelled collagen or non-labelled casein spotted on agarose plates, clearing zones form in the presence of peptidase and/or protease.

Example 9

Determining Endo-arabinase Activity

The culture fluid or a cell lysate of a host strain synthesising and secreting an arabinase in a suitable buffer having a pH chosen for optimal activity of the arabinase, may be assayed for that activity by spotting a suitable sample volume (for example 20 microliter) on an agarose plate which contain the insoluble chromogenic substrate AZCL-arabinan—e.g at a level of 0.1% w/w. The plate is incubated for an appropriate time, e.g. one day, at a temperature suitable for the function of the arabinase, e.g. 37° C. The activity is visible as blue halos around the spots.

The assay may be performed at different pH. At acidic pH the AZCL-arabinan may be prepared by dissolving 0.1 g of AZCL arabinan (Mazurine dyed and cross-linked substrate, Megazyme, Ireland) in 100 ml 0.2M Succinic acid pH3+10 microlitres TritonX-100 (0.01%), to give a final concentration of 0.1% AZCL. At neutral pH the AZCL-arabinan may be prepared by dissolving 0.1 g of AZCL arabinan (Mazurine dyed and cross-linked substrate, Megazyme, Ireland) in 50 ml sterile H₂O plus 10 microlitres TritonX-100 (0.01%). 50 ml 0.4M MOPS pH 7 is then added to the 50 ml AZCL substrate, to give a final volume of 100 ml and a final concentration of 0.2M buffer, 0.1% AZCL.

Example 10

Determining Beta-glucosidase Activity

Many betaglucosidases are likely to have at least some activity on 4-nitrophenyl β-D-glucopyranoside or cellobiose even though that may not be their natural substrates. Activity may also be found using methyl-umbiliferyl beta-D-glucoside which is very sensitive. Generally any (1,4)-β- and (1,3)-β-oligoglucosides can be used as substrate to assess activity of beta-glucosidase by measuring released glucose by using the Trinder assay (The Sigma Diagnostic Glucose (Trinder) Assay, Sigma, St. Louis, Mo.).

One way of determining beta-glucosidase activity is to make a preparation of the culture fluid or a cell lysate of a host strain synthesising and secreting a beta-glucosidase so that the preparation contains approximately $6.9 \times 10^{-6}$ mg/ml of total protein, 100 mM sodium citrate pH 5.0, 0.01% Tween-20 and 4 mM p-nitrophenyl-beta-D-glucopyranoside. The preparation is incubated at 50° C. and aliquots are taken at 0.5, 1, 2, 3, 3.75, and 24 hours. To each aliquot is added 1 M sodium carbonate pH 10.0, and the p-nitrophenyl anion concentration is determined from the absorbance at 405 nm.

Another way of determining beta-glucosidase is make a preparation of the culture fluid or a cell lysate of a host strain synthesising and secreting a beta-glucosidase by first desalting (BioRad Econo-Pac 10DG column) and then concentrating (Centricon Plus-20, Biomax-5, 5 kD cut-off), to a concentration of 0.92 mg/ml (BCA assay). Then the preparation is incubated at 0.037 and 0.0092 pg/ml total protein with 10 mM cellobiose in 100 mM sodium citrate pH 5.0 plus 0.01% Tween-20 at 65° C. Aliquots are taken at 0.5, 1, 2, 3, 4, 6, and 19 hours. Aliquots are boiled 6 minutes to terminate the reaction, and the glucose concentration is determined using the Trinder assay (Sigma Chemical Co., St. Louis, Mo.) and external glucose standards.

Example 11

Determining Esterase Activity

The culture fluid or a cell lysate of a host strain synthesising and secreting an esterase in a suitable buffer is used for measuring the activity. When choosing a substrate for detecting activity of the serine esterase one should preferably choose one which does not form micelles at the concentrations at which the esterase is saturated with substrate, to gain optimal conversion of substrate.

One way of testing esterase activity is to measure the hydrolysis of triacetin in a concentration below CMC for triacetin by the enzyme, by the alkali consumption registered as a function of time under standard conditions such as 30.0° C.; pH 7.0. Hydrolysis of triacetin by esterase will liberate acetic acid which will requires addition of alkali to maintain a a constant pH of 7.0 (pH-stat method) thus the amount of alkali (usually in the form of sodium hydroxide) required to maintain the pH at 7.0 is a measure of triacetin ester bonds hydrolysed.

Another way of testing esterase activity is to measure the hydrolysis by the esterase of PNP-acetat (para-nitrophenyl-acetate) releasing the coloured PNP. 20 microlitres of dilution buffer is pipetted into each well of a 96 well microtiter plate. 5 microlitres of sample (culture fluid supernatant or filtered cell lysate) is added to the dilution buffer. At the start of the assay 200 microlitres of substrate is added to each well and the plate is mounted into an ELISA reader (a programmable spectrophotometer that can read 96 well plates). Absorbance is measured at 405 nm every 30 seconds for 10 minutes. The slope of the time vs. $abs_{405}$ curve is used as an arbitrary activity unit.

Dilution buffer: 25 ml 2M Tris/HCl pH 7.5, 0.50 ml 2M $CaCl_2$, 2.5 ml 15% Brij 35, $H_2O$ 13 500 ml.

Substrate stock solution: a suitable amount of p-Nitrophenyl acetate (analytical grade) is dissolved in 10 ml methanol and stored in a freezer Substrate: 100 microlitres substrate stock solution is mixed with 10 ml dilution buffer.

---

The invention claimed is:

1. An isolated xylanase enzyme comprising an amino acid sequence which has at least 90% identity with a sequence of the mature polypeptide comprised in SEQ ID NO: 4.

2. The xylanase of claim 1, comprising an amino acid sequence which has at least 90% identity with amino acids 1-202 of SEQ ID NO: 4.

3. The xylanase of claim 1, comprising an amino acid sequence which has at least 95% identity with amino acids 1-202 of SEQ ID NO: 4.

4. The xylanase of claim 1, comprising an amino acid sequence which has at least 96% identity with amino acids 1-202 of SEQ ID NO:4.

5. The xylanase of claim 1, comprising an amino acid sequence which has at least 97% identity with amino acids 1-202 of SEQ ID NO:4.

6. The xylanase of claim 1, comprising an amino acid sequence which has at least 98% identity with amino acids 1-202 of SEQ ID NO:4.

7. The xylanase of claim 1, comprising an amino acid sequence which has at least 99% identity with amino acids 1-202 of SEQ ID NO:4.

8. The xylanase of claim 1, comprising amino acids 1-202 of SEQ ID NO:4.

9. The xylanase of claim 1, which consists of amino acids 1-202 of SEQ ID NO:4.

10. A composition comprising the xylanase of claim 1 and an excipient.

11. An isolated polynucleotide comprising a nucleotide sequence which encodes for the xylanase of claim 1.

12. A nucleic acid construct comprising the polynucleotide of claim 11 operably linked to one or more control sequences that direct the production of the xylanase in a host cell.

13. A recombinant expression vector comprising the nucleic acid construct of claim 12.

14. An isolated recombinant host cell comprising the nucleic acid construct of claim 12.

15. A method for producing a xylanase comprising:

a) cultivating the isolated recombinant host cell of claim 14 under conditions conducive for production of the xylanase; and b) recovering the xylanase.

\* \* \* \* \*